United States Patent
Fujii et al.

(10) Patent No.: US 11,696,893 B2
(45) Date of Patent: Jul. 11, 2023

(54) PREPARATION COMPRISING VONOPRAZAN

(71) Applicant: Takeda Pharmaceutical Company Limited, Osaka (JP)

(72) Inventors: Hiroyuki Fujii, Osaka (JP); Akira Suzuki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 150 days.

(21) Appl. No.: 16/629,096

(22) PCT Filed: Jul. 9, 2018

(86) PCT No.: PCT/JP2018/026416
§ 371 (c)(1),
(2) Date: Jan. 7, 2020

(87) PCT Pub. No.: WO2019/013310
PCT Pub. Date: Jan. 17, 2019

(65) Prior Publication Data
US 2020/0163881 A1   May 28, 2020

(30) Foreign Application Priority Data

Jul. 10, 2017  (JP) ................ 2017-135046

(51) Int. Cl.
| | | |
|---|---|---|
| A61K 9/14 | (2006.01) | |
| A61K 9/00 | (2006.01) | |
| A61K 9/20 | (2006.01) | |
| A61K 31/4439 | (2006.01) | |
| A61K 47/12 | (2006.01) | |

(52) U.S. Cl.
CPC .............. *A61K 9/14* (2013.01); *A61K 9/0056* (2013.01); *A61K 9/2018* (2013.01); *A61K 9/2027* (2013.01); *A61K 9/2054* (2013.01); *A61K 31/4439* (2013.01); *A61K 47/12* (2013.01)

(58) Field of Classification Search
None
See application file for complete search history.

(56) References Cited

U.S. PATENT DOCUMENTS

| | | |
|---|---|---|
| 2005/0287211 A1 | 12/2005 | Yoshida et al. |
| 2008/0139639 A1 | 6/2008 | Kajino et al. |
| 2008/0311195 A1* | 12/2008 | Sakuragi .............. A61K 9/0056 424/490 |
| 2009/0155360 A1 | 6/2009 | Venkatesh et al. |
| 2016/0009646 A1 | 1/2016 | Majima |
| 2018/0214460 A1 | 8/2018 | Maeda et al. |

FOREIGN PATENT DOCUMENTS

| | | | |
|---|---|---|---|
| CA | 2994073 A1 | 2/2017 | |
| CN | 103402500 A | 11/2013 | |
| CN | 105030720 A | 11/2015 | |
| CN | 105030725 A | 11/2015 | |
| CN | 105663096 A | 6/2016 | |
| EC | SP11010855 A | 3/2011 | |
| EC | SP11010912 A | 4/2011 | |
| EC | SP17072984 A | 2/2018 | |
| EC | SP18015616 A | 7/2018 | |
| JP | 2008-522952 A | 7/2008 | |
| JP | 2008-260712 A | 10/2008 | |
| JP | 2011-529445 A | 12/2011 | |
| WO | 2006036024 A1 | 4/2006 | |
| WO | 2007026916 A1 | 3/2007 | |
| WO | WO-2007026916 A1 * | 3/2007 | ............ A61K 31/40 |
| WO | 2010013823 A2 | 2/2010 | |
| WO | 2010024451 A1 | 3/2010 | |
| WO | 2012/091153 A2 | 7/2012 | |
| WO | 2014/133059 A1 | 9/2014 | |
| WO | 2016159386 A1 | 10/2016 | |
| WO | 2016193860 A1 | 12/2016 | |
| WO | 2017/018473 A1 | 2/2017 | |

OTHER PUBLICATIONS

International Search Report dated Nov. 15, 2018 in corresponding International Application No. PCT/JP2018/026416.
Formacion Continuada, Para Farmaceuticos De Hospital 3.2 (<http://www.ub.es/legmh/capitols/sunyenegre.pdf>).
Medicamento, Wikipedia (<http://es.wikipedia.org/wiki/Forma_gal%C3%A9nica>).
SCP/15/3, Annex IV (http://www.wipo.int/ edocs/ mdocs/ scp/ es/ scp_15/ scp_15_3-annex4.pdf).
Registro Oficial, article 268.
Proceso 12-IP-98, pp. 10-11 (<http://intranet.comunidadan.dina.org/Documentos/Procesos/12-ip-98.doc>).
Letter from Russian associate dated Nov. 19, 2021 regarding the Russian office action of Russian Application No. 2020105670, which cited the publication of WO2016193860A1.
Opposition of corresponding Ecuadorian Application No. 2020-9533 (PCT/JP2018/026416) in Spanish and English translation.
Formacion Continuada, Para Farmaceuticos De Hospital 3.2 (<http://www.ub.es/legmh/capitols/sunyenegre.pdf>), 2002.
Medicamento, Wikipedia (<http://es.wikipedia.org/wiki/Forma_gal%C3%A9nica>), 2021.

(Continued)

*Primary Examiner* — Robert A Wax
*Assistant Examiner* — William Craigo
(74) *Attorney, Agent, or Firm* — McCarter & English, LLP; David G. Conlin

(57) ABSTRACT

The present invention aims to provide a preparation expected to improve the bitter taste of an organic acid salt of vonoprazan and permit rapid dissolution of the organic acid salt of vonoprazan after administration.
The present invention provides a preparation containing fine granules or granules containing (1) a core granule containing an organic acid salt of vonoprazan, (2) an intermediate layer containing the same organic acid as the organic acid forming the salt of vonoprazan in (1), or a salt thereof, and (3) a coating layer containing a water-insoluble polymer.

16 Claims, 16 Drawing Sheets

(56) References Cited

OTHER PUBLICATIONS

Gaceta Oficial, Process 89-AI-2000, p. 30, paragraph 4.1.2.1. (http://intranet.comunidadandina.org/documentos/ Gacetas/ gace722.pdf).
Goodman & Gilman's text: The pharmacological basis of therapeutics. 9th Ed. Interamerican. 1996. Mexico, p. 47.
Moscoso A. Raul., Propiedad intelectual e innovaci0n tecnologica en el Ecuador. (Intellectual property and technological innovation in Ecuador) Abya Yala. Quito. 2000. pp. 37-38.
Quito, 2000, p. 31.
Frónesis. [online]. Dec. 2006, vol. 13, No. 3 [quoted Dec. 7, 2011], pp. 9-31; available on the WWW at: <http://www.scielo.org.ve/scielo.php?script=sci_arttext&pid=S1315-62682006000300002&lng>.
SCP/15/3, Annex IV (http://www.wipo.int/ edocs/ mdocs/ scp/ es/ scp_15/ scp_15_3-annex4.pdf), 2011.
WIPO/IP/CCS/1/03/1. 2004, p. 76.
Registro Oficial, article 268, 2016.
Proceso 12-IP-98, pp. 10-11 (<http://intranet.comunidadan.dina.org/Documentos/Procesos/12-ip-98.doc)>, 1998.
Japanese Office Action for Application No. 2019-571547, dated Jun. 28, 2022, 8 pages.

\* cited by examiner

PREPARATION COMPRISING VONOPRAZAN

TECHNICAL FIELD

The present invention relates to a preparation with a possibly improved bitter taste of an organic acid salt of vonoprazan.

BACKGROUND OF THE INVENTION

Along with the aging of the population and changes in the living environment, there is a demand for the development of an orally disintegrating tablet that can be easily taken at any time anywhere without water and that can maintain the convenience of handling as a characteristic of tablet.

When a pharmaceutically active ingredient or other additive is a substance having an uncomfortable taste such as bitter taste and the like, it is preferable from the aspect of medication compliance to mask such uncomfortable taste by coating same. On the other hand, the pharmaceutically active ingredient is desired to be rapidly dissolved to express pharmacological effects after administration. When the pharmaceutically active ingredient has a strong bitter taste, however, a thick coating for masking same prevents rapid dissolution, and these two are difficult to achieve at the same time.

1-[5-(2-Fluorophenyl)-1-(pyridin-3-ylsulfonyl)-1H-pyrrol-3-yl]-N-methylmethanamine monofumarate (vonoprazan fumarate) is known to have a superior proton pump inhibitory action (patent document 1) and may be useful as a medicament. Organic acid salts of vonoprazan such as vonoprazan fumarate and the like are known to have a bitter taste.

DOCUMENT LIST

Patent Documents

[patent document 1] WO 2007/026916
[patent document 2] WO 2010/013823

SUMMARY OF THE INVENTION

Problems to be Solved by the Invention

The present invention aims to provide a preparation expected to improve the bitter taste of an organic acid salt of vonoprazan and permit rapid dissolution of an organic acid salt of vonoprazan after administration.

Means of Solving the Problems

The present inventors have conducted intensive studies in an attempt to solve the aforementioned problems and found that a preparation comprising fine granules or granules comprising (1) a core granule containing an organic acid salt of vonoprazan, (2) an intermediate layer containing the same organic acid as the organic acid forming the salt of vonoprazan in (1), or a salt thereof, and (3) a coating layer containing a water-insoluble polymer may ensure a given time during which the organic acid salt of vonoprazan is not dissolved after administration (i.e., lag time). The lag time prevents dissolution of the pharmaceutically active ingredient until passage through the throat, whereby the bitter taste is expected to be improved.

The present inventors have further found that the above-mentioned constitution may achieve rapid dissolution as well as improvement of bitter taste after lapse of the lag time.

The present inventors conducted further studies based on the above-mentioned finding and completed the present invention.

That is, the present invention provides the following.

[1] A preparation comprising fine granules or granules comprising (1) a core granule containing an organic acid salt of vonoprazan,
(2) an intermediate layer containing the same organic acid as the organic acid forming the salt of vonoprazan in (1), or a salt thereof, and
(3) a coating layer containing a water-insoluble polymer.
[2] The preparation of the above-mentioned [1], wherein the organic acid salt of vonoprazan is vonoprazan fumarate, the organic acid or a salt thereof in the aforementioned (2) is fumaric acid or a salt of fumaric acid.
[3] The preparation of the above-mentioned [1] or [2], wherein the water-insoluble polymer is a pH-independent water-insoluble polymer.
[4] The preparation of the above-mentioned [3], wherein the pH-independent water-insoluble polymer is an ammonioalkylmethacrylate copolymer.
[5] The preparation of any of the above-mentioned [1]-[4], wherein the organic acid or a salt thereof in the aforementioned (2) is not less than about 0.5 parts by weight per 100 parts by weight of vonoprazan in the aforementioned (1).
[6] The preparation of any of the above-mentioned [1]-[5], wherein the water-insoluble polymer (solid content) in the coating layer in the aforementioned (3) is about 0.5 parts by weight-about 15 parts by weight per 100 parts by weight of the particles comprising the core granule in the aforementioned (1) and the intermediate layer of the aforementioned (2).
[7] The preparation of any of the above-mentioned [1]-[6], wherein the aforementioned fine granules or granules have an average particle size of about 75 μm-about 750 μm.
[8] The preparation of [1], wherein the intermediate layer of (2) contains the same organic acid as the organic acid forming the salt of vonoprazan in (1), or a salt thereof, and a dissolution controlling substance in a single layer or separate layers.
[9] The preparation of the above-mentioned [8], wherein the dissolution controlling substance has solubility in water (100 g) at 20° C. of 0.01-500.
[10] The preparation of the above-mentioned [8], wherein the dissolution controlling substance has pH 2-4 when dissolved in water.
[11] The preparation of the above-mentioned [8], wherein the dissolution controlling substance is a salt of an organic acid or organic acid.
[12] The preparation of the above-mentioned [8], wherein the dissolution controlling substance is a divalent carboxylic acid or a salt thereof.
[13] The preparation of the above-mentioned [8], wherein the dissolution controlling substance is succinic acid or a salt of succinic acid.
[14] The preparation of any of the above-mentioned [1]-[13], wherein the aforementioned fine granules or granules are further coated with a coagulation inhibiting substance.
[15] The preparation of the above-mentioned [14], wherein the aforementioned coagulation inhibiting substance is an inorganic substance, sugar alcohol or saccharide.
[16] The preparation of any of the above-mentioned [1]-[15], further comprising a polymer binder.

[17] The preparation of any of the above-mentioned [1]-[16] as an orally disintegrating tablet.

Effect of the Invention

The preparation of the present invention is a preparation expected to achieve both improvement of a bitter taste of an organic acid salt of vonoprazan and rapid dissolution thereof.

DETAILED DESCRIPTION OF THE INVENTION

Figure 1:
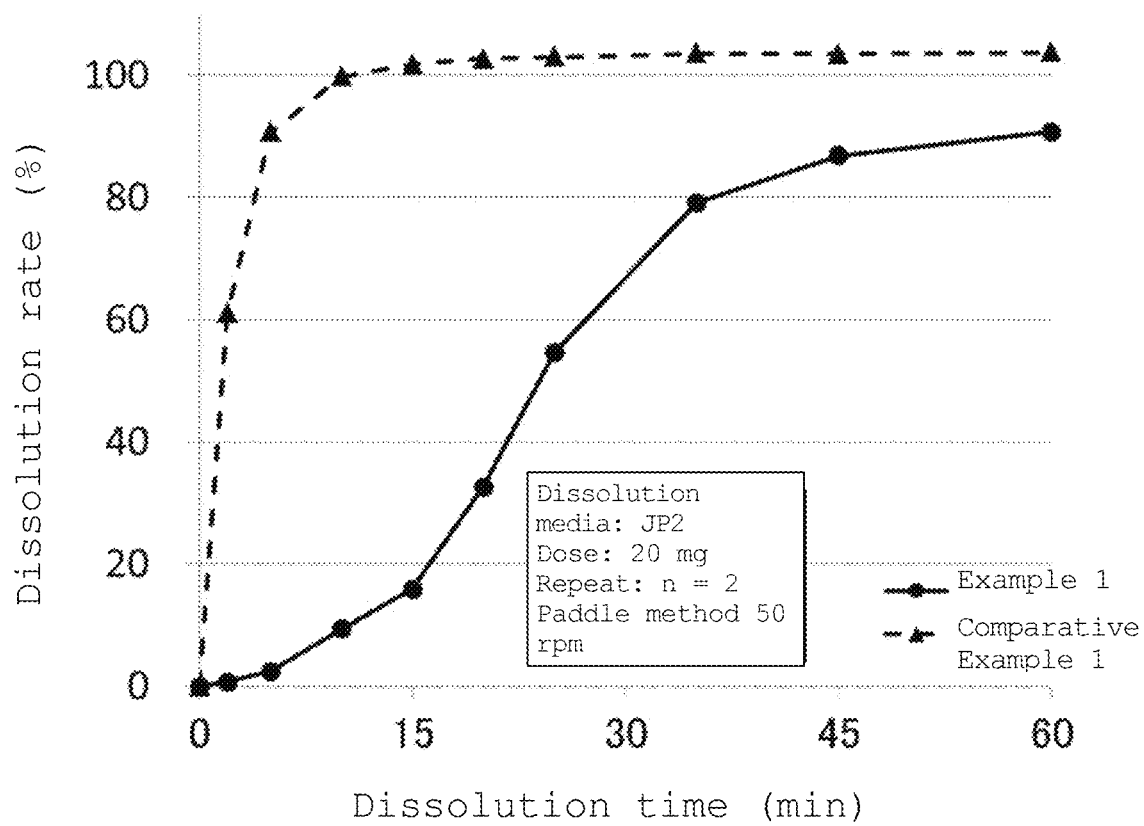
FIG. 1 is a graph showing the results of the dissolution test of the tablet containing the water-insoluble polymer-coated particles obtained in Example 1 and the tablet containing the organic acid-coated particles obtained in Comparative Example 1. In the figure legend, JP2 shows the second solution of the Japanese Pharmacopoeia dissolution test. The same is true for the following Figures.
Figure 2:
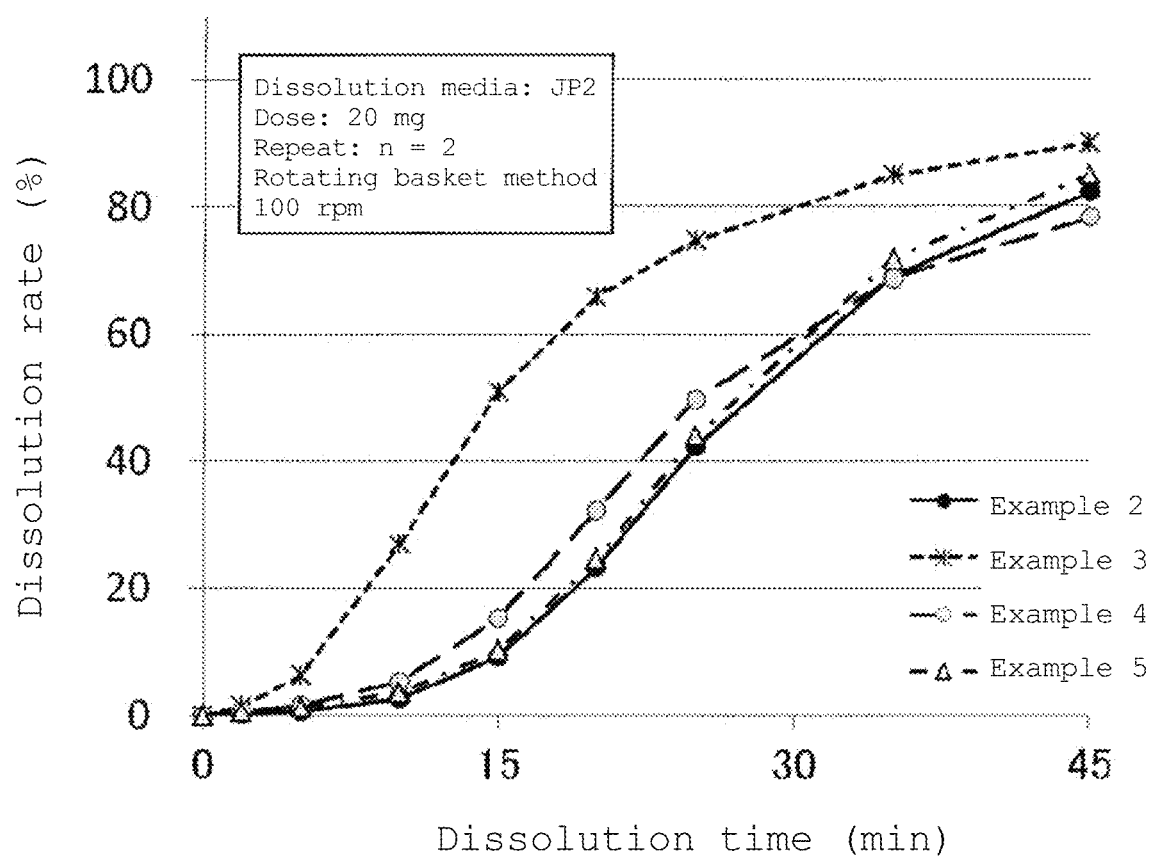
FIG. 2 is a graph showing the results of the dissolution test of the tablets containing the water-insoluble polymer-coated particles obtained in Examples 2-5.
Figure 3:
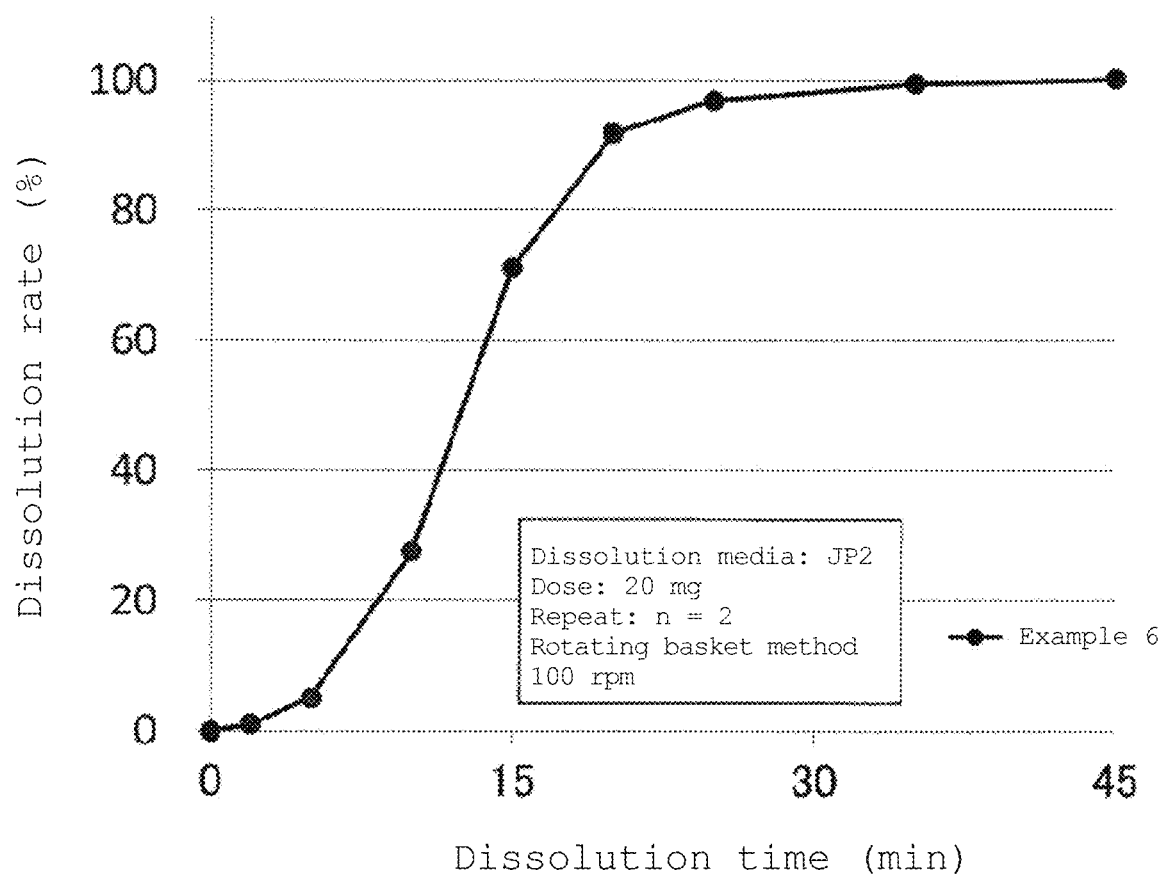
FIG. 3 is a graph showing the results of the dissolution test of the tablet containing the water-insoluble polymer-coated particles obtained in Example 6.
Figure 4:
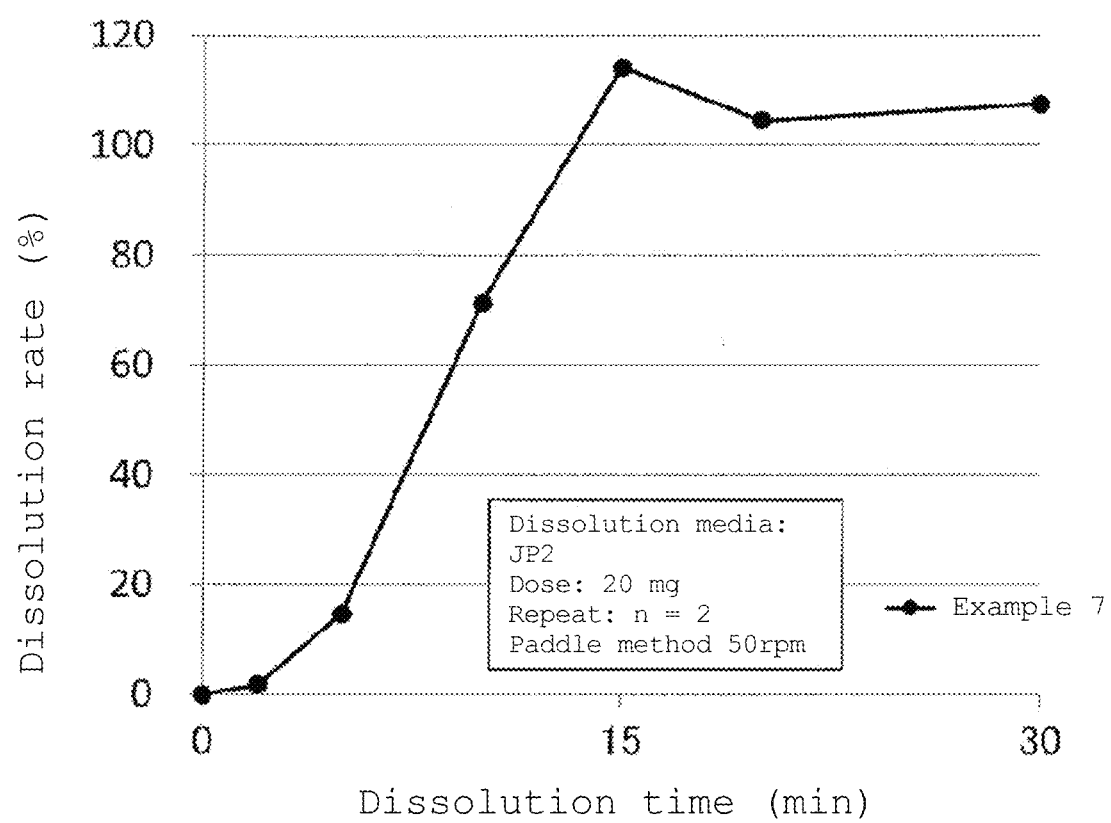
FIG. 4 is a graph showing the results of the dissolution test of the tablet containing the water-insoluble polymer-coated particles obtained in Example 7.
Figure 5:
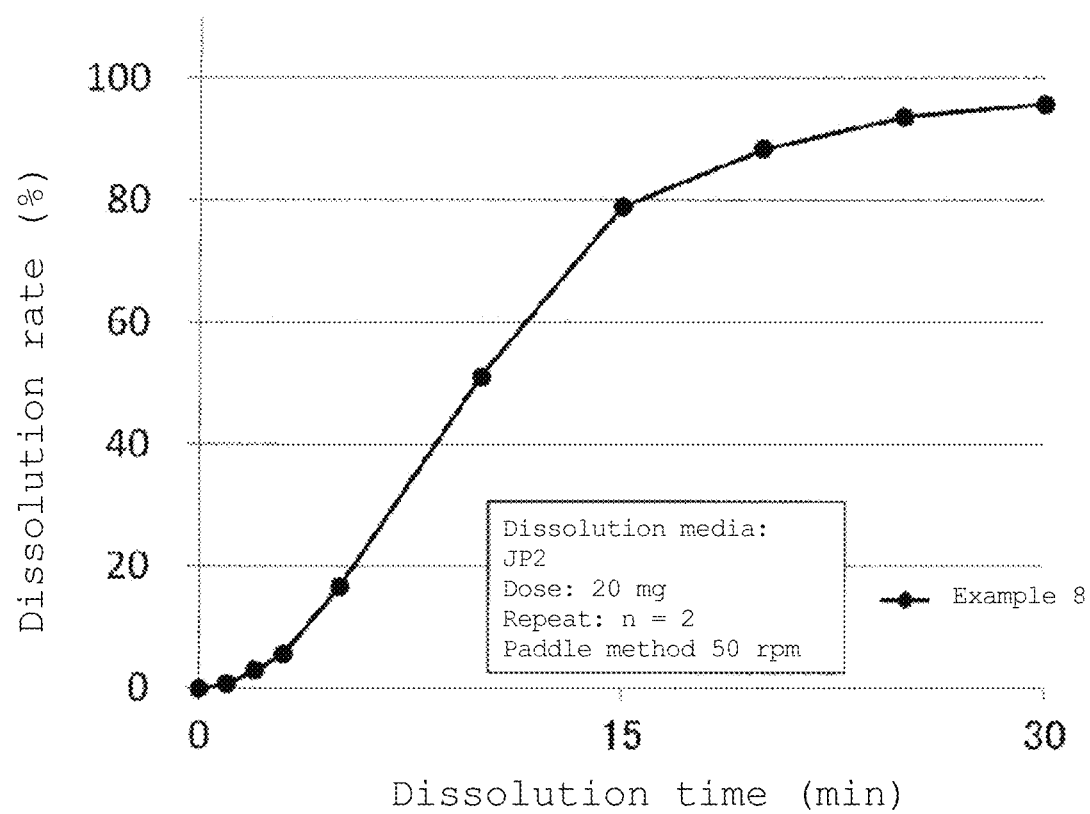
FIG. 5 is a graph showing the results of the dissolution test of the tablet containing the water-insoluble polymer-coated particles-obtained in Example 8.
Figure 6:
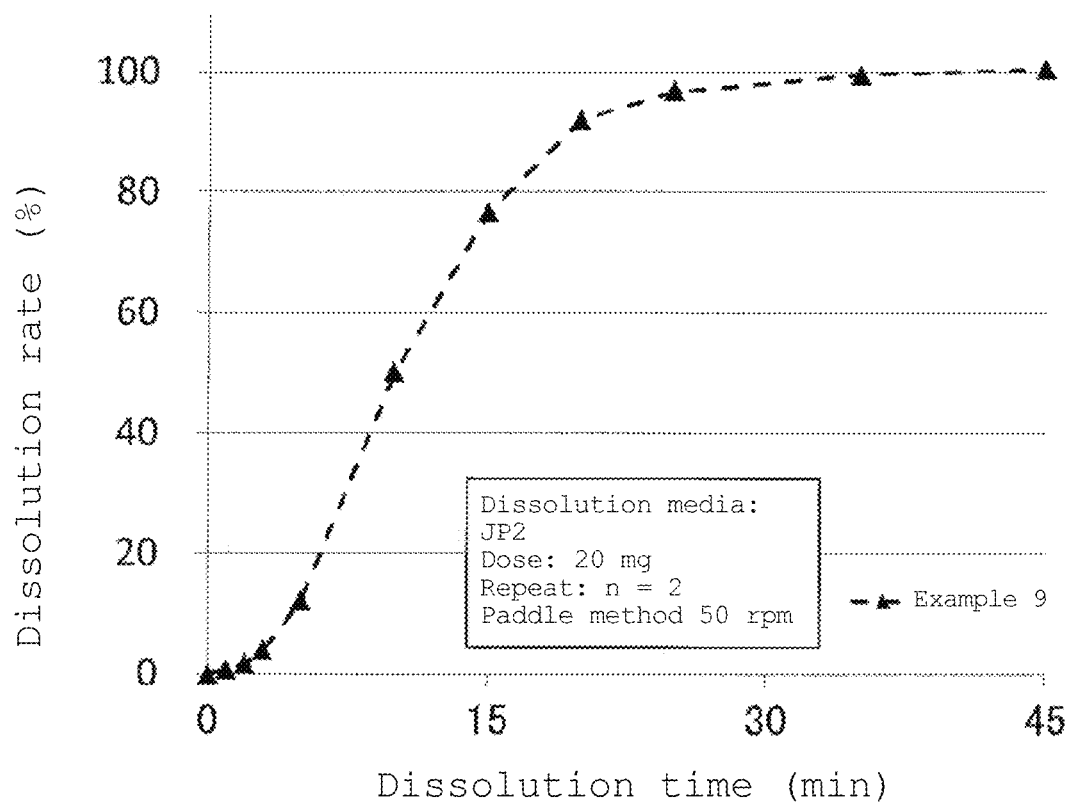
FIG. 6 is a graph showing the results of the dissolution test of the tablet containing the water-insoluble polymer-coated particles obtained in Example 9.
Figure 7:
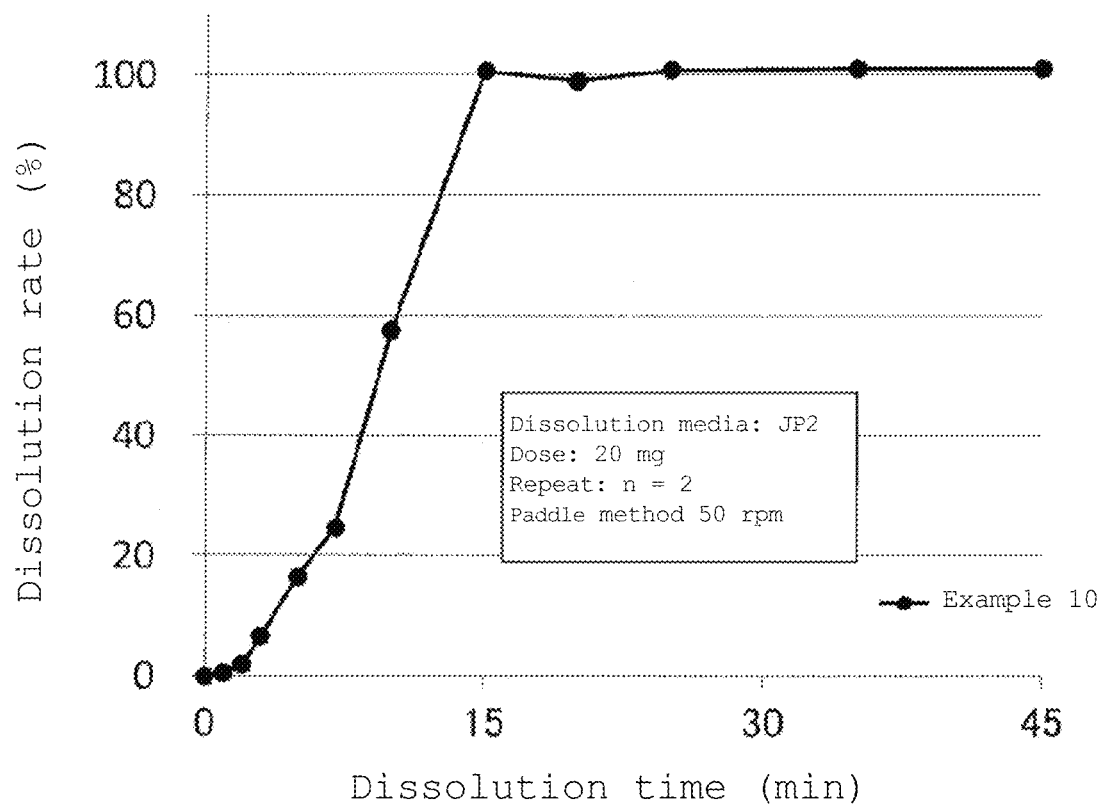
FIG. 7 is a graph showing the results of the dissolution test of the tablet containing the water-insoluble polymer-coated particles obtained in Example 10.
Figure 8:
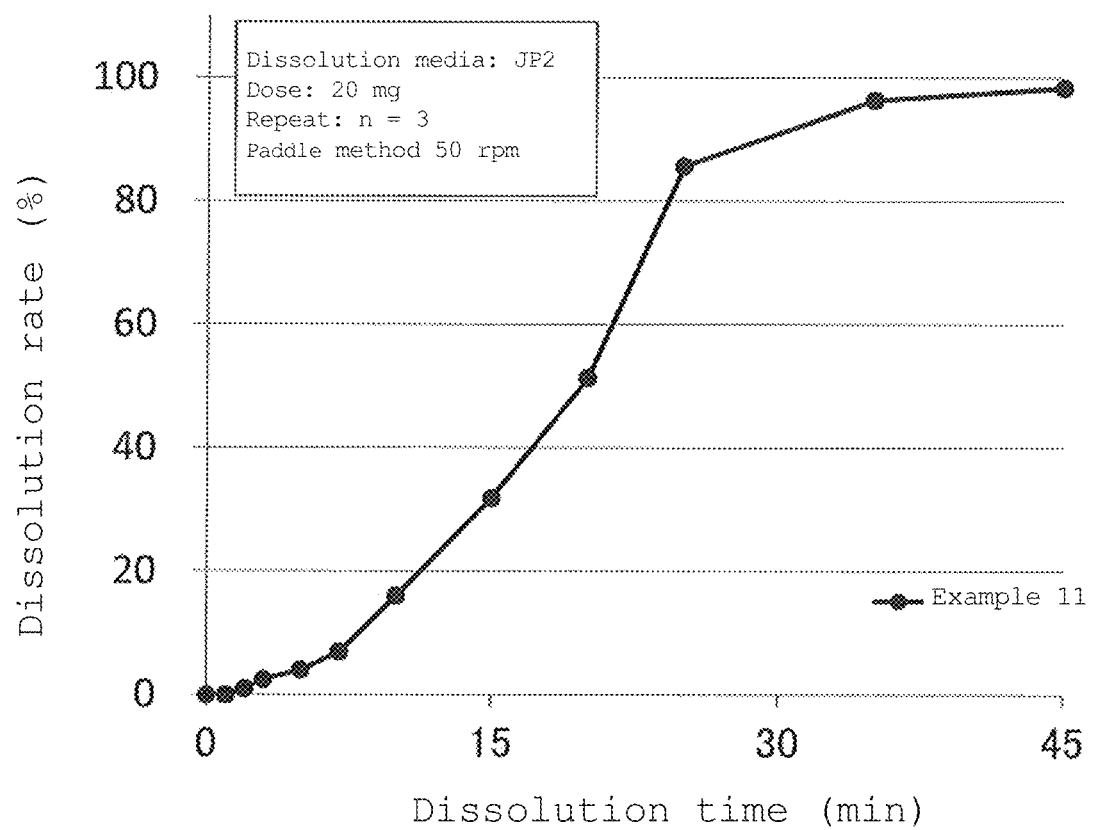
FIG. 8 is a graph showing the results of the dissolution test of the tablet containing the water-insoluble polymer-coated particles obtained in Example 11.
Figure 9:
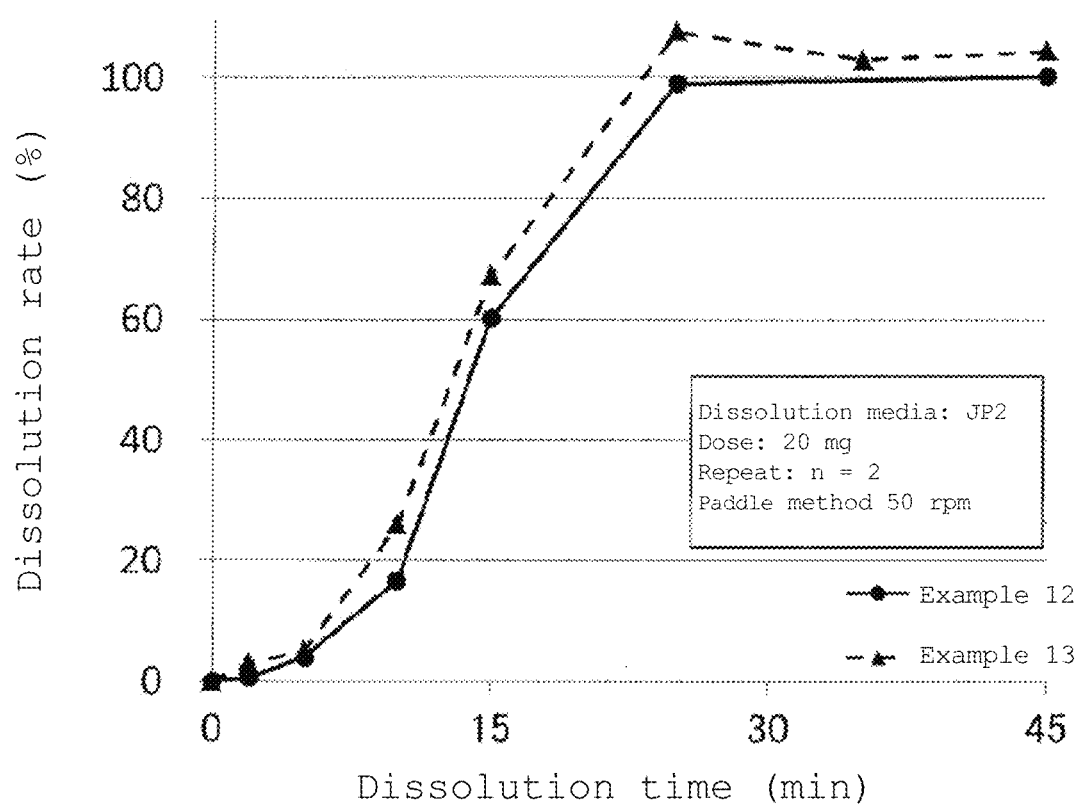
FIG. 9 is a graph showing the results of the dissolution test of the tablets containing the water-insoluble polymer-coated particles obtained in Examples 12-13.
Figure 10:
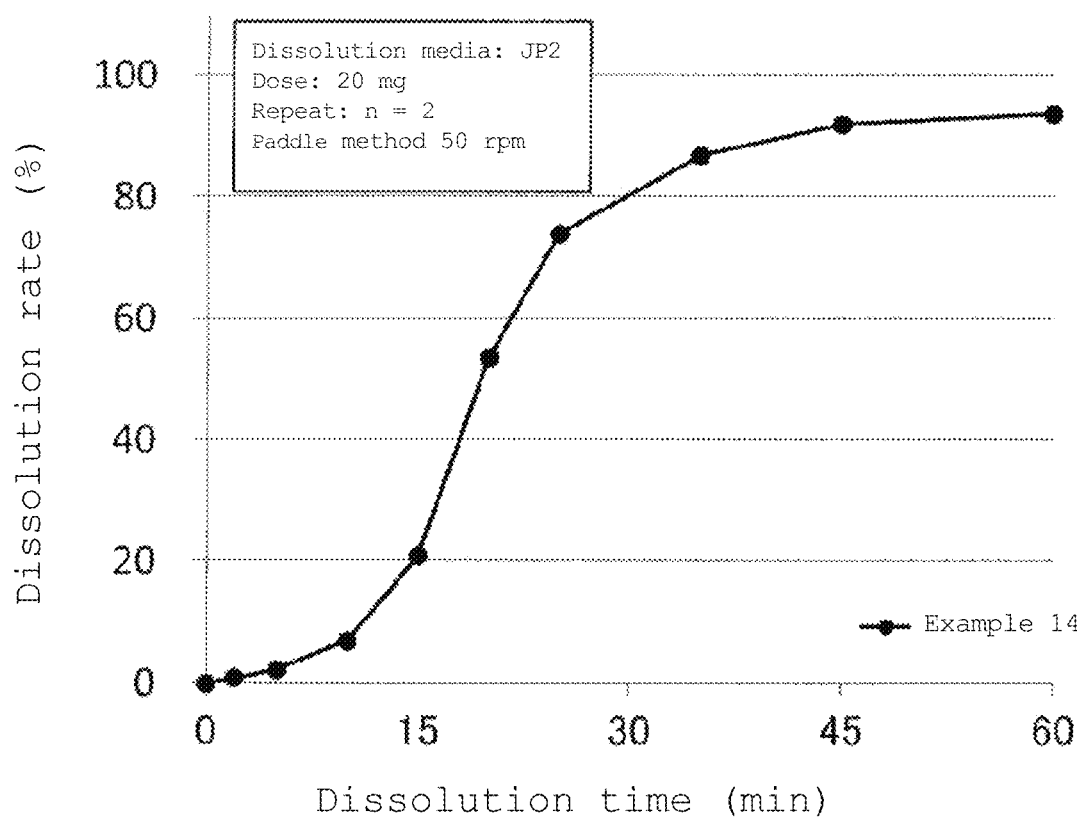
FIG. 10 is a graph showing the results of the dissolution test of the tablet containing the water-insoluble polymer-coated particles obtained in Example 14.

The preparation of the present invention characteristically comprises fine granules or granules comprising (1) a core granule containing an organic acid salt of vonoprazan (sometimes described as core granule (1) in the present specification), (2) an intermediate layer containing the same organic acid as the organic acid forming the salt of vonoprazan in (1), or a salt thereof (sometimes described as intermediate layer (2) in the present specification), and (3) a coating layer containing a water-insoluble polymer (sometimes described as coating layer (3) in the present specification).

In the present invention, the fine granules or granules having core granule (1), intermediate layer (2), and coating layer (3) have an average particle size of generally about 50 μm-about 1 mm, preferably about 75 μm-about 750 μm, more preferably about 80 μm-about 500 μm, further preferably about 100 μm-about 400 μm.

When the fine granules or granules are further coated with the below-mentioned coagulation inhibiting substance (e.g., D-mannitol, light anhydrous silicic acid), the above-mentioned average particle size is that of the particles after coating with the coagulation inhibiting substance.

In the present specification, the "average particle size" shows, unless otherwise specified, a volume standard median size (median size: 50% particle size from cumulative distribution). Examples of the measurement method thereof include a laser diffraction particle size distribution measurement method. Specific examples thereof include a method using a laser diffraction particle size distribution measurement apparatus HEROS RODOS (manufactured by Sympatec (Germany)). The average particle size of the "fine granules or granules" in the present invention may be measured after production of the "fine granules or granules" and before formulation of the final preparation in the production process of the preparation or may be measured by taking out the "fine granules or granules" from the formulated final preparation, or the like. In the measurement of the average particle size by this measurement method, an error is considered to be present at about ±10% including the measurement errors caused by the apparatus and measurement method. "About" attached to the numerical value of the average particle size is used to encompass an error of "±10%". That is, in the present specification, for example, a numerical value range of the average particle size of "about 75 μm-about 750 μm" means 67.5 μm-825 μm.

When an average particle size of the granules or fine granules contained in the preparation of the present invention is measured, a part of the granules or fine granules may be bonded to form aggregates in the production process of the preparation. In this case, it is desirable to separate the above-mentioned aggregate and single granules or fine granules by, for example, a method such as sieving and the like, and then measure the size. Particularly, when the final preparation is a tablet such as orally disintegrating tablet and the like, the tablet after tableting is pulverized and the average particle size of the granules or fine granules contained in the tablet is measured, it is desirable to confirm where necessary, the state of existence and particle size of the aggregate by image analysis, sieve the aggregate, single granules and fine granules with a sieve of a size capable of separating them from the aggregate, and then measure the size.

In the present specification, "coating" is used to mean not only covering the entire surface of the object to be coated (e.g., core) but also covering partly or adsorbing or absorbing.

In the present specification, "granules" mean those granulated into a granular state.

In the present specification, "fine granules" refer to those that completely pass a No. 18 sieve and pass a No. 30 sieve except not more than 10% of the total amount remaining on the No. 30 sieve.

In the present invention, "granule or fine granule" means one granule or fine granule produced by covering one "core granule". When one aggregate having a plurality of "core granule" is formed as a result of bonding of a part of granules or fine granules as mentioned above, such one aggregate is not considered to be one "granule or fine granule" and the "granule or fine granule" means an independent single particle produced by covering individual core granules.

The preparation of the present invention characteristically contains an organic acid salt of vonoprazan (sometimes referred to as component (I) in the present specification) as a pharmaceutically active ingredient in core granule (1).

In the present invention, as an organic acid forming a salt of vonoprazan in the organic acid salt of vonoprazan (component (I)), for example, fumaric acid, succinic acid, benzoic acid, citric acid, mesylic acid, tartaric acid, besylic acid and the like can be mentioned, and fumaric acid is preferable.

In the present invention, as an organic acid salt of vonoprazan, vonoprazan fumarate is preferable.

In the present invention, core granule (1) may be the below-mentioned core of an inactive carrier coated with a layer containing an organic acid salt of vonoprazan.

The preparation of the present invention is characterized in that the intermediate layer (2) contains an organic acid or a salt thereof, and the organic acid of the "organic acid or a salt thereof" is the same as the organic acid forming the salt with vonoprazan in component (I). In the present specification, the "organic acid or a salt thereof" contained in the intermediate layer (2) is sometimes referred to as component (II).

The organic acid of component (II) is the same as the organic acid explained in the above-mentioned component (I).

Examples of the salt of the organic acid of component (II) include alkali metal salt such as sodium salt, potassium salt and the like, alkaline earth metal salt such as calcium salt, magnesium salt and the like, and ammonium salt.

In the present invention, the organic acid salt of vonoprazan (component (I)) contained in core granule (1) is preferably vonoprazan fumarate, and the organic acid or a salt thereof (component (II)) contained in intermediate layer (2) is preferably fumaric acid or a salt of fumaric acid (preferably, fumaric acid or monosodium fumarate).

The content of an organic acid salt of vonoprazan (component (I)) in the preparation of the present invention is generally about 1 wt %-about 80 wt %, preferably about 5 wt %-about 50 wt %, more preferably about 15 wt %-about 35 wt %, relative to "core granule (1)".

The content of organic acid or a salt thereof (component (II)) in intermediate layer (2) in the preparation of the present invention is preferably not less than about 0.5 parts by weight, more preferably not less than about 10 parts by weight, further preferably not less than about 150 parts by weight, per 100 parts by weight of vonoprazan (free form) in core granule (1).

The content of organic acid or a salt thereof (component (II)) in intermediate layer (2) in the preparation of the present invention is generally about 0.5 parts by weight-about 5000 parts by weight, preferably about 1 part by weight-about 5000 parts by weight, more preferably about 10 parts by weight-about 1000 parts by weight, further preferably about 50 parts by weight-about 500 parts by weight, per 100 parts by weight of vonoprazan (free form) in core granule (1).

The weight of the above-mentioned "vonoprazan (free form)" is based on the vonoprazan free form of the organic acid salt of vonoprazan contained in core granule (1).

The preparation of the present invention characteristically has coating layer (3) on the outside of the intermediate layer (2).

In the present invention, examples of the "water-insoluble polymer" contained in the coating layer (3) include pH-independent water-insoluble polymer (e.g., ammonioalkylmethacrylate copolymer (alias, ammonioalkylmethacrylate copolymer RS (e.g., Eudragit RS30D (trade name), Eudragit RSPO (trade name)), alias, ammonioalkylmethacrylate copolymer RL (e.g., Eudragit RL30D (trade name), Eudragit RLPO (trade name))), ethylcellulose, ethylcellulose water dispersion solution, ethyl acrylate-methyl methacrylate copolymer dispersion solution (e.g., Eudragit NE30D (trade name))), vinyl acetate resin (Kollicoat SR (trade name)), gastrosoluble polymer (e.g., aminoalkylmethacrylate copolymer E, polyvinylacetal diethylamino acetate, Kollicoat Smartseal 30D (trade name)), enteric polymer (e.g., methacrylic acid copolymer LD, methacrylic acid copolymer L, methacrylic acid copolymer S, acetyl cellulose, cellulose acetate phthalate, carboxymethylethylcellulose, hydroxypropylmethylcellulose acetate phthalate, hydroxypropylmethylcellulosephthalate), preferably pH-independent water-insoluble polymer (e.g., ammonioalkylmethacrylate copolymer (alias, ammonioalkylmethacrylate copolymer RS, alias, ammonioalkylmethacrylate copolymer RL)), more preferably ammonioalkylmethacrylate copolymer (alias, ammonioalkylmethacrylate copolymer RS, alias, ammonioalkylmethacrylate copolymer RL).

One or more kinds of water-insoluble polymers can be used in combination.

The content of the water-insoluble polymer (solid content) in coating layer (3) in the preparation of the present invention is preferably about 0.5 parts by weight-about 15 parts by weight, more preferably about 1 part by weight-about 10 parts by weight, further preferably about 1 part by weight-about 7 parts by weight, per 100 parts by weight of the particles composed of core granule (1) and intermediate layer (2).

In the present invention, the "particles composed of core granule (1) and intermediate layer (2)" refers to the particles before coated with coating layer (3).

The preparation of the present invention preferably has an intermediate layer containing a dissolution controlling substance between core granule (1) and coating layer (3).

The intermediate layer containing a dissolution controlling substance may be the aforementioned intermediate layer (2) containing a dissolution controlling substance or an "intermediate layer containing a dissolution controlling substance" different from the aforementioned intermediate layer (2).

As an embodiment of the preparation of the present invention, a preparation comprising fine granules or granules comprising (1) a core granule containing an organic acid salt of vonoprazan (component (I)), (2) an intermediate layer containing the same organic acid as the organic acid forming the salt of vonoprazan in (1), or a salt thereof (component (II)), and a dissolution controlling substance in a single layer or separate layers and
(3) a coating layer containing a water-insoluble polymer can be mentioned.

In the preparation of the present invention, to exert an effect of ensuring a certain time (i.e., lag time) in which the organic acid salt of vonoprazan is not dissolved after administration, an intermediate layer containing component (II) is preferably present near the core granule containing component (I).

Therefore, in the preparation of the present invention, the intermediate layer (2) is an intermediate layer containing component (II) and a dissolution controlling substance in a single layer; or the intermediate layer (2) is an intermediate layer composed of plural layers separately containing component (II) and a dissolution controlling substance, wherein the intermediate layer containing component (II) is preferably present on the side of core granule (1) (on core granule (1)).

In the present invention, the dissolution controlling substance refers to a substance capable of forming a lag time before dissolution of vonoprazan (free form). For example, it is a substance that, when dissolved, temporarily insolubilizes or decreases the solubility of vonoprazan (free form).

In the present invention, the dissolution controlling substance preferably has solubility of 0.01-500 (preferably 0.1-100, more preferably 0.5-40) in 100 g of water at 20° C.

In the present invention, the dissolution controlling substance is preferably a substance having pH 2-4 when dissolved in water.

In the present invention, examples of the dissolution controlling substance include organic acid (including hydrate) (e.g., divalent carboxylic acid (e.g., succinic acid, malic acid, adipic acid, malonic acid and the like), salicylic acid and the like); salt of organic acid (including hydrate) (e.g., salt of divalent carboxylic acid (e.g., salt of succinic acid (e.g., disodium succinate, disodium succinate hexahydrate and the like) and the like), ammonium carbonate, potassium hydrogen carbonate, sodium carbonate decahydrate, sodium hydrogen carbonate, sodium acetate trihydrate and the like); sugar alcohol (e.g., mannitol, erythritol, maltitol and the like); saccharides (e.g., sucrose, lactose, maltose, trehalose and the like); disintegrant (e.g., low-substituted hydroxypropylcellulose, carmellose and the like); water-soluble polymer (e.g., hydroxypropylmethylcellulose and the like); inorganic salt (including hydrate) (e.g., ammonium chloride, ammonium nitrate, potassium chloride, disodium hydrogen phosphate 12-water, sodium thiosulfate pentahydrate, ammonium oxalate monohydrate, sodium pyrrophosphate and the like); amide compound (e.g., urea and the like); amino acid (e.g., glycine and the like); salt of amino acid (e.g., cysteine hydrochloride and the like); phenols (e.g., hydroquinone and the like); water-insoluble polymer (e.g., vinyl polymer (e.g., poly(N-acrylamide) and the like) and the like), and salt of succinic acid or succinic acid is preferable.

One or more kinds of dissolution controlling substances can be used in combination.

The content of the dissolution controlling substance in the preparation of the present invention is generally about 10 parts by weight-about 1000 parts by weight, preferably about 50 parts by weight-about 600 parts by weight, more preferably about 200 parts by weight-about 500 parts by weight, per 100 parts by weight of the water-insoluble polymer (solid content) in coating layer (3).

In the present invention, when succinic acid is contained as the dissolution controlling substance, ammonioalkylmethacrylate copolymer (alias, ammonioalkylmethacrylate copolymer RS) is preferably used as the aforementioned water-insoluble polymer since rapid dissolution of an organic acid salt of vonoprazan after lapse of the lag time can be expected.

In the present invention, when succinic acid or a salt thereof is used as component (II) in intermediate layer (2) and the amount of the succinic acid or a salt thereof is within the above-mentioned range, the above-mentioned effect is expected to be afforded.

In the present invention, when succinic acid is contained as the dissolution controlling substance, it is expected to contribute to the stabilization of vonoprazan and a preparation superior in long-term stability is expected to be provided.

In the preparation of the present invention, the "fine granules or granules containing core granule (1), intermediate layer (2), and coating layer (3)" are preferably further coated with a coagulation inhibiting substance.

Examples of the coagulation inhibiting substance include inorganic substance, sugar alcohol and saccharides.

Examples of the inorganic substance include light anhydrous silicic acid (e.g., Sylysia 320 (trade name), AEROSIL 200 (trade name)), hydrated silicon dioxide, talc, titanium oxide, bentonite, kaolin and magnesium alumino metasilicate, and light anhydrous silicic acid is preferable.

Examples of the sugar alcohol include D-mannitol, sorbitol, maltitol, reduced starch saccharides, xylitol, reduced paratinose, erythritol, lactitol and isomalt.

Examples of the saccharides include monosaccharides (e.g., glucose, fructose) and disaccharides (e.g., lactose, sucrose, maltose, white sugar, trehalose).

The amount of the coagulation inhibiting substance to be used for coating fine granules or granules when saccharide or sugar alcohol is used as the coagulation inhibiting substance is generally about 1 part by weight-about 30 parts by weight, preferably about 3 parts by weight-about 20 parts by weight, more preferably about 4 parts by weight-about 15 parts by weight, per 100 parts by weight of the "fine granules or granules containing core granule (1), intermediate layer (2), and coating layer (3)" (fine granules or granules before applying a coagulation inhibiting substance).

The amount of the coagulation inhibiting substance to be used for coating fine granules or granules when an inorganic substance is used as the coagulation inhibiting substance is generally about 0.01 part by weight-about 10 parts by weight, preferably about 0.05 parts by weight-about 5 parts by weight, more preferably about 0.1 part by weight-about 1 part by weigh, per 100 parts by weight of the "fine granules or granules containing core granule (1), intermediate layer (2), and coating layer (3)" (fine granules or granules before applying a coagulation inhibiting substance).

In the present invention, a coating film of a coagulation inhibiting substance is expected to provide effects of improved handling property (reduced attaching due to static electricity) and suppressed delay in the dissolution of the preparation after storage.

The preparation of the present invention preferably further contains a polymer binder.

The polymer binder may be any as long as it has property causing sufficiently strong binding of each additive to granules or fine granules from the viewpoint of abrasion resistance. Examples thereof include water-soluble polymer (hydroxypropylmethylcellulose (HPMC) (e.g., hydroxypropylmethylcellulose 2910), hydroxypropylcellulose, carmellose sodium, methylcellulose (e.g., Metolose SM-4 (trade name)), poly(vinyl alcohol), sodium alginate, poly(vinyl alcohol)-acrylic acid-methyl methacrylate copolymer, polyethylene oxide, povidone, copolyvidone, polyethylene glycol), gastrosoluble polymer (Eudragit E (trade name), Eudragit EPO (trade name)), pH-independent water-insoluble polymer (Eudragit NE (trade name), Eudragit RL (trade name) (e.g., Eudragit RLPO (trade name), Eudragit RL30D (trade name)), Eudragit RS (trade name), ethylcellulose), preferably, hydroxypropylmethylcellulose (HPMC), Eudragit E (trade name), Eudragit EPO (trade name), Eudragit NE (trade name), Eudragit RL (trade name) and methylcellulose (e.g., Metolose SM-4 (trade name)).

The content of the polymer binder in the preparation of the present invention is generally 0.1 part by weight-100 parts by weight, preferably 0.5 parts by weight-90 parts by weight, more preferably 1 part by weight-80 parts by weight, per 100 parts by weight of the organic acid contained in the preparation.

In the present invention, the polymer binder is used as, though not limited to, for example, a binder of the organic acid-containing layer.

The preparation of the present invention can further contain cyclodextrin.

As cyclodextrin, α-cyclodextrin, β-cyclodextrin, 2-hydroxypropyl-β-cyclodextrin can be mentioned, and β-cyclodextrin is preferable.

In the present invention, masking of the sour taste of the organic acid component (e.g., fumaric acid, succinic acid) can be expected by containing cyclodextrin (particularly β-cyclodextrin).

In the present invention, cyclodextrin may be contained in any part of the preparation of the present invention. It is preferably contained in the below-mentioned outer layer granules or component outside the granules, and more preferably contained in the outer layer granules.

The content of the cyclodextrin in the preparation of the present invention is generally 1 part by weight-1000 parts by weight, preferably 10 parts by weight-500 parts by weight, more preferably 25 parts by weight-100 parts by weight, per 100 parts by weight of the organic acid contained in the preparation.

The preparation of the present invention can be formulated as an orally disintegrating tablet containing the aforementioned fine granules or granules or the like. This is explained in detail in the following.

Examples of the preparation of the present invention include solid preparations such as tablet, granule, fine granule, capsule, foam formulation and the like, liquids such as suspension and the like, and the like. In view of the easiness of handling and the like, tablet is preferable, and orally disintegrating tablet is particularly preferable.

In the present specification, the "orally disintegrating tablet" is a tablet characterized by appropriate disintegration property, which can be ingested by dissolving or disintegrating rapidly in the oral cavity.

The preparation of the present invention can be produced using the above-mentioned components and according to a method known in the field of pharmaceutical preparation.

For example, when the preparation of the present invention is an orally disintegrating tablet, it can be produced as follows.

In the following production method, coating of component (c) is optional.

The core of an inactive carrier is successively sprayed with coating liquids of the following (a), (b), (c) prepared in advance, dried, and sieved as necessary to give component (I)-containing particles. Alternatively, the core of an inactive carrier is successively sprayed with coating liquids of the following (a), (d) prepared in advance, dried, and sieved as necessary to give component (I)-containing particles.

(a) A binder is suspended or dissolved in water or a solvent (e.g., ethanol, methanol, acetone, ethyl acetate, propylene glycol, isopropyl alcohol), component (I) (e.g., vonoprazan fumarate) is added, and suspended or dissolved therein to give a component (I) coating liquid.

(b) A binder is suspended or dissolved in water or a solvent (e.g., ethanol, methanol, acetone, ethyl acetate, propylene glycol, isopropyl alcohol), component (II) (e.g., fumaric acid, monosodium fumarate) is added, and suspended or dissolved therein to give a component (II) coating liquid.

(c) A binder is suspended or dissolved in water or a solvent (e.g., ethanol, methanol, acetone, ethyl acetate, propylene glycol, isopropyl alcohol), a dissolution controlling substance (e.g., succinic acid) is added, and suspended or dissolved therein to give a dissolution controlling substance coating liquid.

(d) A binder is suspended or dissolved in water or a solvent (e.g., ethanol, methanol, acetone, ethyl acetate, propylene glycol, isopropyl alcohol), a dissolution controlling substance (e.g., succinic acid) is added, and suspended or dissolved therein, then component (II) (e.g., fumaric acid, monosodium fumarate) is added, and suspended or dissolved therein to give a component (II)/dissolution controlling substance coating liquid.

Examples of the binder include the above-mentioned polymer binders.

The coating layers may be applied in any order and may be applied plural times. For example, (a), (b), (c) may be applied to the core in this order, (a), (b), (c), (b) may be applied to the core in this order, (a), (b), (b), (c) may be applied to the core in this order, or (a), (d) may be applied to the core in this order.

The component (I)-containing particles may further has a coating layer not containing component (I), component (II) or the dissolution controlling substance but containing a binder (e.g., HPMC). Such layer may be formed between the active pharmaceutical ingredient layer (layer (a)) and an organic acid layer (layer (b), layer (c), or layer (d)).

Each layer may further contain the below-mentioned additive (e.g., corrigent (e.g., sodium glutamate), surfactant (e.g., polysorbate 80), coagulation inhibitor (e.g., talc)) used for general preparations. These components may be used by adding to the above-mentioned coating liquids.

A coating liquid containing a water-insoluble polymer (e.g., ammonioalkylmethacrylate copolymer (e.g., Eudragit RS30D (trade name), Eudragit RSPO (trade name), Eudragit RLPO (trade name))) is sprayed on the obtained component (I)-containing particles and they are dried and sieved where necessary to give fine granules or granules.

A coating layer containing a water-insoluble polymer may further contain the below-mentioned additives used for general preparations (e.g., plasticizer (e.g., triacetin), coagulation inhibitor (e.g., talc), colorant (e.g., red ferric oxide, yellow ferric oxide, titanium oxide), plasticizer (e.g., polysorbate 80), pH adjuster (e.g., citric anhydride), shading agent (e.g., titanium oxide)). These components may be used by adding to the above-mentioned coating liquids.

The obtained fine granules or granules may be further coated with a coagulation inhibiting substance. In this case, a coagulation inhibiting substance (e.g., D-mannitol, light anhydrous silicic acid) is suspended or dissolved in a solvent such as water and the like to give a coagulation inhibiting substance coating liquid, and the coating liquid is sprayed on the fine granules or granules, dried and sieved as necessary to give coagulation inhibiting substance-coated particles. The coagulation inhibiting substance (e.g., D-mannitol, light anhydrous silicic acid) is mixed with fine granules or granules, whereby coagulation inhibiting substance-coated particles can also be obtained.

The obtained fine granules or granules (or coagulation inhibiting substance-coated particles) are formed (tableted) together with optionally-added outer layer granules and/or component outside granules to give the orally disintegrating tablet of the present invention.

The outer layer granules can be obtained by, for example, granulating excipient (e.g., D-mannitol, crystalline cellulose), corrigent (e.g., citric anhydride), disintegrant (e.g., low-substituted hydroxypropylcellulose, crospovidone) and, where necessary, β-cyclodextrin.

Examples of the component outside granules include sweetening agent (e.g., aspartame, acesulfame potassium, thaumatin), corrigent (e.g., l-menthol, monosodium fumarate), lubricant (e.g., sodium stearyl fumarate, magnesium stearate), excipient (e.g., crystalline cellulose), disintegrant (e.g., crospovidone, partly pregelatinized starch), flavor (e.g., lime flavor, orange flavor, strawberry flavor, strawberry D, peppermint cortone), fluidizer (e.g., Neusilin FL2 (trade name), Neusilin UFL2 (trade name), AEROSIL 200 (trade name), Sylysia 320 (trade name)) and β-cyclodextrin.

As the outer layer granules, a commercially available premix preparation for direct tableting can also be used. For example, SmartEX (trade name), Parteck ODT (trade name), Granutol F (trade name), Rudy flash (trade name), GRANFILLER-D (trade name) SWELLWiCK (trade name) can be mentioned. A processing starting material suitable for direct tableting such as a spray dry product or granulated product of mannitol, lactose and the like, and the like may also be used.

The content of the outer layer granules as a total amount is generally 10 wt %-95 wt %, preferably 30 wt %-90 wt %, more preferably 35 wt %-80 wt %, relative to the weight of the whole preparation.

The content of the component outside granules as a total amount is generally 0.5 wt %-40 wt %, preferably 0.75 wt %-35 wt %, more preferably 1 wt %-30 wt %, relative to the weight of the whole preparation.

Examples of the core of the inactive carrier include (1) a spherical granulated product of crystalline cellulose and lactose, (2) a spherical granulated product of mannitol, (3) 75-300 μm spherical crystalline cellulose (CELPHERE manufactured by Asahi Kasei Chemicals Co., Ltd.), (4) a 50-250 μm stirring granulated product of lactose (9 parts) and a starch (1 part), (5) a micro particle of 250 μm or below obtained by classification of microcrystalline cellulose spherical granules described in JP-A-61-213201, (6) a processed product of waxes and the like formed spherically by spray chilling or melt granulation, (7) processed product such as gelatin bead product of oil component and the like, (8) calcium silicate, (9) starch, (10) partly pregelatinized starch, (11) porous particles of chitin, cellulose, chitosan and the like, (12) bulk product of mannitol, granulated sugar, crystalline lactose, crystalline cellulose or sodium chloride and the like and preparation processed products thereof. Furthermore, these cores may be produced by a pulverization method or granulation method known per se and screened to prepare particles of desired particle size.

Examples of the of the "spherical granulated product of crystalline cellulose and lactose" include (i) 100-200 μm spherical granulated product of crystalline cellulose (3 parts) and lactose (7 parts) (e.g., NONPAREIL 105 (70-140) (particle size 100-200 μm), manufactured by Freund Corporation), (ii) 150-250 μm spherical granulated product of crystalline cellulose (3 parts) and lactose (7 parts) (e.g., NONPAREIL NP-7:3, manufactured by Freund Corporation), (iii) 100-200 μm spherical granulated product of crystalline cellulose (4.5 parts) and lactose (5.5 parts) (e.g., NONPAREIL 105T (70-140) (particle size 100-200 μm), manufactured by Freund Corporation) and the like, (iv) 150-250 μm spherical granulated product of crystalline cellulose (5 parts) and lactose (5 parts) [e.g., NONPAREIL NP-5:5, manufactured by Freund Corporation].

"Mixing" is carried out by a mixing method generally used such as mixing, kneading, granulation. The "mixing" is carried out using an apparatus such as vertical granulator (VG10 (manufactured by POWREX CORPORATION)), universal kneader (manufactured by HATA TEKKOSHO CO., LTD.), fluid bed granulator (LAB-1, FD-3S, FD-WSG-60, FD-WSG-60TW, FD-GPCG-120SPC, FD-MP-01 (SPC/SFP/FD), MP-10 toku-2 type (manufactured by POWREX CORPORATION)), V-TYPE MIXER, tumbler mixer, container type blending machine.

"Forming" is carried out by a single punch tableting machine (manufactured by Kikusui Seisakusho Ltd.), rotary tableting machine (manufactured by Kikusui Seisakusho Ltd.) and the like by punching at a pressure of about 1-about 30 kN/cm$^2$, preferably about 2-about 20 kN/cm$^2$.

"Drying" may be performed by any method used for general drying of preparation such as vacuum drying, fluidized bed drying and the like.

The "spraying", "coating", "granulation", "sieving" are performed by methods known per se.

The tabletting method of the orally disintegrating tablet may be performed at room temperature or at a temperature exceeding room temperature. The "Room temperature" generally refers to about 10° C.-about 30° C. The temperature can be changed according to the quality of the desired tablet.

The orally disintegrating tablet may be an uncoated tablet, a film-coated agent or a sugar-coated tablet, and desirably an uncoated tablet. In the present specification, the "uncoated tablet" means a tablet not subjected to a coating treatment such as film coating, sugar coating and the like of the surface of the orally disintegrating tablet obtained by the tableting step.

The preparation of the present invention may further contain, as ingredients other than those mentioned above, additives used for the production of general preparations. The amount thereof to be added is that used for the production of general preparations.

As the additive, water-soluble sugar alcohol, crystalline cellulose, low-substituted hydroxypropylcellulose (L-HPC) are used, and binder, souring agent, foaming agent, sweetener, flavor, lubricant, colorant, excipient, disintegrant, corrigent, plasticizer, surfactant, coagulation inhibitor, fluidizer, pH adjuster, and the like are further added, mixed and compression molded to give an orally disintegrating tablet.

The water-soluble sugar alcohol means a sugar alcohol that requires less than 30 ml of water when sugar alcohol (1 g) is added to water, and dissolved within about 30 min by vigorously shaking for 30 sec at 20° C. every 5 min.

Examples of the water-soluble sugar alcohol include mannitol, sorbitol, maltitol, reduced starch saccharides, xylitol, reduced paratinose, erythritol, lactitol, preferred are mannitol, sorbitol, maltitol, xylitol, erythritol, more preferred are mannitol, sorbitol, maltitol, erythritol, further preferred are mannitol, erythritol. Two or more kinds thereof may be used in a mixture at an appropriate ratio. Erythritol is generally produced from glucose as a starting material and by fermentation by yeast and the like. One with a particle size of 50 mesh or below is used. The erythritol is obtained as a commercially available product [Nikken Chem. Co., Ltd. etc.]. The water-soluble sugar alcohol is generally used at about 3-about 60 parts by weight, preferably about 5-about 50 parts by weight, per 100 parts by weight of the whole preparation.

Crystalline cellulose may be any as long as it is obtained by partial depolymerization of α-cellulose and purification thereof. It also includes cellulose called microcrystalline cellulose. As crystalline cellulose, for example, CEOLUS KG-1000, CEOLUS KG-802, CEOLUS PH-101, CEOLUS PH-102, CEOLUS PH-301, CEOLUS PH-302, CEOLUS UF-702, CEOLUS UF-711 can be specifically mentioned. Preferably, CEOLUS KG-802 or CEOLUS UF-711 can be mentioned. These crystalline celluloses may be used singly or two or more kinds thereof may be used in combination. These crystalline celluloses can be obtained as commercially available products [manufactured by Asahi Kasei Chemicals Co., Ltd.]. Crystalline cellulose can be added at about 1-about 50 parts by weight, preferably about 3-about 40 parts by weight, most preferably about 5-about 20 parts by weight, per 100 parts by weight of the whole preparation.

Examples of the low-substituted hydroxypropylcellulose include LH-11, LH-21, LH-22, LH-B1, LH-31, LH-32, LH-33. These LHPCs can be obtained as commercially available products [manufactured by Shin-Etsu Chemical Co., Ltd.]. The low-substituted hydroxypropylcellulose may be added at about 1-about 50 parts by weight, preferably about 3-about 40 parts by weight, most preferably about 3-about 20 parts by weight, per 100 parts by weight of the whole preparation.

Examples of the binder include hydroxypropylcellulose, hydroxypropylmethylcellulose, crystalline cellulose, pregelatinized starch, polyvinylpyrrolidone, gum arabic powder, gelatin, pullulan, pectin, xanthan gum, carrageenan, guar gum, gellan gum, poly(vinyl alcohol), poly(vinyl alcohol)-polyethylene glycol-graft copolymer, copolyvidone, methylcellulose, low-substituted hydroxypropylcellulose, poly(vinyl alcohol)-acrylic acid-methyl methacrylate copolymer. Two or more kinds of these binders may be used in a mixture at an appropriate ratio.

Examples of the souring agent include citric acid, tartaric acid, malic acid, succinic acid, fumaric acid, lactic acid, acetic acid, adipic acid, glucono-delta-lactone, phytic acid, and salts of these.

Examples of the foaming agent include sodium bicarbonate.

Examples of the sweetener include xylose, starch syrup, hydrogenated maltose starch syrup, maltose, glucose, fructose, simple syrup, dextrin, cyclodextrin, maltose, lactose, trehalose, malt oligosaccharide, isomalt oligosaccharide, gentiooligosaccharide, saccharine sodium, glycyrrhizin, aspartame, sucralose, acesulfame potassium, stevia, thaumatin, advantame, neotame.

The flavor may be any of synthetic substance and naturally occurring substance. For example, lemon, lime, orange, menthol, strawberry, peppermint, banana, ginger, Japanese apricot, grapefruit, yogurt, vanilla, Chinese lemon, blueberry, green tea, cole, grape, sugar can be mentioned.

Examples of the corrigent include sodium glutamate, citric anhydride, 1-menthol, monosodium fumarate.

Examples of the lubricant include magnesium stearate, calcium stearate, stearic acid, sucrose fatty acid ester, polyethylene glycol, talc, sodium stearyl fumarate, glycerol, stearic acid monoglyceride, castor oil, hydrogenated castor oil.

Examples of the colorant include food colors such as Food Color Yellow No. 5, Food Color Red No. 2, Food Color Blue No. 2; food lake colors, red iron oxide, red ferric oxide, yellow ferric oxide, black iron oxide, carbon black and the like.

Examples of the excipient include lactose, sucrose, isomalto, D-mannitol, sorbitol, anhydrous calcium phosphate, starch, cornstarch, partly pregelatinized starch, crystalline cellulose, light anhydrous silicic acid, titanium oxide.

Examples of the disintegrant include crospovidone [manufactured by ISP Inc. (USA), BASF (Germany)], croscarmellose sodium (FMC-Asahi Kasei Corporation), carmellose calcium (GOTOKU CHEMICAL CO., LTD.), low-substituted hydroxypropylcellulose, sodium carboxymethyl starch (Matsutani Chemical Industry Co., Ltd.), cornstarch, pregelatinized starch, crystalline cellulose. Of these, crospovidone is preferably used. Two or more kinds of these disintegrants may be used in a mixture at an appropriate ratio. For example, crospovidone may be used alone, or crospovidone may be used in combination with other disintegrant. Crospovidone may be any as long as it is a crosslinked polymer substance called 1-ethenyl-2-pyrrolidinone homopolymer including polyvinyl polypyrrolidone (PVPP), 1-vinyl-2-pyrrolidinone homopolymer. Generally, crospovidone having a molecular weight of not less than 1,000,000 is used. Specific examples of commercially available products of crospovidone include cross-linked (cross-linking) povidone, Kollidon CL, Kollidon CL-F, Kollidon CL-SF [manufactured by BASF (Germany)], Polyplasdone XL, Polyplasdone XL-10, INF-10 [manufactured by ISP Inc. (USA)], polyvinylpyrrolidone, PVPP, 1-vinyl-2-pyrrolidinone homopolymer. Such disintegrant is used at, for example, about 0.1-about 30 parts by weight, preferably about 1-about 25 parts by weight, further preferably about 1.5-about 20 parts by weight, per 100 parts by weight of the whole preparation.

Examples of the plasticizer include polyethylene glycol, propylene glycol, ethanol, triethyl citrate, triacetin, polysorbate 80.

Examples of the surfactant include sodium lauryl sulfate, cetyltrimethylammonium bromide, docusate sodium, polyoxyethylene hydrogenated castor oil, polysorbate 80, polysorbate 20.

Examples of the coagulation inhibitor include talc, titanium oxide, light anhydrous silicic acid, kaolin, bentonite, hydrated silicon dioxide, stearic acid monoglyceride, mannitol, trehalose, erythritol, lactose, maltose.

Examples of the fluidizer include magnesium alumino metasilicate, light anhydrous silicic acid, hydrated silicon dioxide, talc.

Examples of the pH adjuster include citric anhydride, hydrochloric acid, sodium hydroxide.

As an embodiment of the fine granules or granules included in the preparation of the present invention, they may have the core of an inert carrier, a layer containing component (I) on the outside of the core of the inactive carrier, a layer containing component (II) on the outside of the layer containing component (I), and a layer containing a water-insoluble polymer on the outside of the layer containing component (II).

As an embodiment of the fine granules or granules included in the preparation of the present invention, they may have the core of an inert carrier, a layer containing component (I) on the outside of the core of the inactive carrier, a layer containing component (II) on the outside of the layer containing component (I), a layer containing a dissolution controlling substance on the outside of the layer containing component (II), and a coating layer containing a water-insoluble polymer on the outside of the layer containing the dissolution controlling substance.

As an embodiment of the fine granules or granules included in the preparation of the present invention, they may have the core of an inert carrier, a layer containing component (I) on the outside of the core of the inactive carrier, a layer containing component (II) and a dissolution controlling substance on the outside of the layer containing component (I), and a layer containing a water-insoluble polymer on the outside of the layer containing component (II) and the dissolution controlling substance.

As an embodiment of the fine granules or granules included in the preparation of the present invention, they may have the core of an inert carrier, a layer containing component (I) on the outside of the core of the inactive carrier, a layer containing a polymer binder on the outside of the layer containing component (I), a layer containing component (II) on the outside of the layer containing the polymer binder, and a coating layer containing a water-insoluble polymer on the outside of the layer containing component (II).

As an embodiment of the fine granules or granules included in the preparation of the present invention, they may have the core of an inert carrier, a layer containing component (I) on the outside of the core of the inactive carrier, a layer containing a polymer binder on the outside of the layer containing component (I), a layer containing component (II) on the outside of the layer containing the polymer binder, a layer containing a dissolution controlling substance on the outside of the layer containing component (II), and a coating layer containing a water-insoluble polymer on the outside of the layer containing the dissolution controlling substance.

As an embodiment of the fine granules or granules included in the preparation of the present invention, they may have the core of an inert carrier, a layer containing component (I) on the outside of the core of the inactive carrier, a layer containing a polymer binder on the outside of the layer containing component (I), a layer containing component (II) and a dissolution controlling substance on the outside of the layer containing the polymer binder, and a layer containing a water-insoluble polymer on the outside of the layer containing component (II) and the dissolution controlling substance.

The orally disintegrating tablet of the present invention shows rapid disintegration property or solubility in the oral cavity.

The orally disintegrating tablet of the present invention can be easily taken while maintaining the convenience of handling. In addition, it can be taken at any time anywhere without water, and the oral disintegration time (time before complete disintegration of an orally disintegrating tablet with saliva in the oral cavity of healthy male and female adults) is within 1 min, generally not more than about 50 sec, preferably not more than about 40 sec, further preferably not more than about 30 sec.

The preparation of the present invention is expected to ensure a certain lag time before dissolution of a pharmaceutically active ingredient (an organic acid salt of vonoprazan).

Specifically, the preparation of the present invention preferably has the dissolution property of the following (1) or (2).

(1) In a dissolution test according to the Japanese Pharmacopoeia Paddle Method (rotating speed 50 rpm, 37° C.) or the Japanese Pharmacopoeia Rotatory basket method (rotating speed 100 rpm, 37° C.) using the Japanese Pharmacopoeia dissolution test 2nd fluid (900 mL), the time from the start of the test until dissolution of 5% of the pharmaceutically active ingredient is not less than 2 min and not more than 15 min.

(2) In a dissolution test using the Japanese Pharmacopoeia dissolution test 2nd fluid (10 mL), the dissolution rate of the pharmaceutically active ingredient in 1 min from the start of the test is not more than 5%.

The preparation of the present invention more preferably has the dissolution property of the above-mentioned (2).

While the preparation of the present invention (particularly orally disintegrating tablet) is designed to ensure a certain time (lag time) in which the organic acid salt of vonoprazan is not dissolved after administration to prevent dissolution of the pharmaceutically active ingredient until after passage through the throat, it is desirable that the ingredient is dissolved rapidly after the lag time and there is no need to form an enteric coating layer that inhibits dissolution until the preparation reaches the small intestine.

The preparation of the present invention can be safely administered orally to mammals (e.g., mouse, rat, rabbit, cat, dog, bovine, horse, monkey, human etc.). While the dose of the preparation of the present invention varies, for example, depending on the subject of administration, the kind of disease and the like, it can be appropriately selected from the range in which the dose of the pharmaceutically active ingredient is effective.

The preparation of the present invention contains an organic acid salt of vonoprazan (particularly, vonoprazan fumarate) as a pharmaceutically active ingredient. It has lower toxicity, is a safe preparation, and is useful for gastric ulcer, duodenal ulcer, reflux esophagitis, non-erosive reflux disease, suppression of recurrence of gastric ulcer or duodenal ulcer in administration of a low dose of acetylsalicylic acid, suppression of recurrence of gastric ulcer or duodenal ulcer in administration of non-steroidal antiinflammatory agents; adjunct to *Helicobacter pylori* eradication in the following settings: gastric ulcer, duodenal ulcer, gastric MALT lymphoma, idiopathic thrombocytopenic purpura, the stomach after endoscopic resection of early stage gastric cancer, or *Helicobacter pylori* gastritis, and the like. The dose thereof as vonoprazan is about 10-about 40 mg/day for one adult (60 kg body weight). The preparation may be administered once per day or in 2-3 portions per day.

The preparation of the present invention may be used in combination with low dose acetylsalicylic acid and/or non-steroidal antiinflammatory agents (NSAIDs). Examples of the non-steroidal antiinflammatory agent include acetylsalicylic acid, indomethacin, ibuprofen, mefenamic acid, diclofenac, etodolac, piroxicam, celecoxib, loxoprofen sodium, naproxen and the like.

It may also be used in combination with anti-*Helicobacter pylori* active substance, imidazole compound, bismuth salt, quinolone compound and the like for aiding *Helicobacter pylori* eradication or eradication.

Examples of the "anti-*Helicobacter pylori* active substance" include penicillin antibiotics (e.g., amoxicillin, benzylpenicillin, piperacillin, mecillinam, ampicillin, temocillin, bacampicillin, aspoxicillin, sultamicillin, lenampicillin etc.), cephem antibiotics (e.g., cefixime, cefaclor etc.), macrolide antibiotics (e.g., erythromycin, clarithromycin, roxithromycin, rokitamycin, flurithromycin, telithromycin etc.), tetracycline antibiotics (e.g., tetracycline, minocycline, streptomycin etc.), aminoglycoside antibiotics (e.g., gentamicin, amikacin etc.), imipenem and the like. Of these, penicillin antibiotic, macrolide antibiotic and the like are preferable.

Examples of the "imidazole compound" include metronidazole, miconazole and the like.

Examples of the "bismuth salt" include bismuth acetate, bismuth citrate, bithmuth subsalicylate and the like.

Examples of the "quinolone compound" include ofloxacin, ciploxacin and the like.

Among others, for *Helicobacter pylori* eradication, penicillin antibiotics (e.g., amoxicillin etc.), erythromycin antibiotics (e.g., clarithromycin etc.) and/or imidazole compounds (e.g., metronidazole etc.) are preferably used.

EXAMPLES

While the present invention is explained more specifically in the following by referring to Examples and Experimental Examples, the present invention is not limited thereby.

In the Examples, Comparative Examples, Reference Examples and Experimental Examples, compound A is vonoprazan fumarate.

In the following Examples and the like, the "organic acid coating liquid" refers to a coating liquid containing an organic acid or a salt of the organic acid, and the "organic acid-coated particles" refers to particles coated with a coating liquid containing an organic acid or a salt of the organic acid.

Example 1

[Preparation of Compound a Coating Liquid]

To purified water (399.8 g) were added hydroxypropylmethylcellulose 2910 (alias hypromellose (2910), TC-5E, manufactured by Shin-Etsu Chemical Co., Ltd., hereinafter the same) (24.3 g), compound A (180.3 g) was added and the mixture was stirred well to give a compound A coating liquid.

[Preparation of Compound A-Coated Particles]

Lactose/crystalline cellulose spherical granules (NONPAREIL 105T, manufactured by Freund Corporation, hereinafter the same) (300.5 g) were placed and fluidized in a fine particle coater granulator/Wurster (FD-MP-01(SPC/SFP/FD), manufactured by POWREX, hereinafter the same), the compound A coating liquid (570.0 g) was sprayed at spray air pressure 0.5 MPa, spray air flow rate 60 NL/min, inlet air temperature 65-75° C., inlet air flow rate 0.4-0.5 m$^3$/min, spray liquid feed rate 5 g/min, and the particles were dried to give particles after drying (445.5 g). The total amount of the particles after drying was sieved to give compound A-coated particles (300 μm-105 μm) (413.6 g).

[Preparation of Organic Acid Coating Liquid]

To purified water (480.5 g) were added hydroxypropylmethylcellulose 2910 (24.3 g) and fumaric acid jet milled in advance (manufactured by POLYNT, hereinafter the same) (120.5 g) and the mixture was stirred well to give an organic acid coating liquid.

[Preparation of Organic Acid-Coated Particles]

The compound A-coated particles (300 μm-105 μm) (400.0 g) were placed and fluidized in a fine particle coater granulator/Wurster, the organic acid coating liquid (561.5 g) was sprayed at spray air pressure 0.4-0.5 MPa, spray air flow rate 50-70 NL/min, inlet air temperature 73° C., inlet air flow rate 0.5 m$^3$/min, spray liquid feed rate 3-9 g/min and the particles were dried to give particles after drying (499.3 g). The total amount of the particles after drying was sieved to give organic acid-coated particles (355 μm-105 μm) (374.6 g).

[Preparation of Water-Insoluble Polymer Coating Liquid]

In purified water (350.3 g) were suspended and dissolved triacetin (manufactured by Merck, hereinafter the same) (6.05 g), talc (manufactured by matsumura sangyo Co., Ltd., hereinafter the same) (30.3 g), and red ferric oxide (LCW, hereinafter the same) (0.1321 g), and the mixture was added to stirring aminoalkylmethacrylate copolymer RS (alias ammonioalkylmethacrylate copolymer, Eudragit RS30D, manufactured by Evonik) (199.8 g) to give a water-insoluble polymer coating liquid.

[Preparation of Water-Insoluble Polymer-Coated Particles]

The organic acid-coated particles (355 μm-105 μm) (299.8 g) were placed and fluidized in a fine particle coater granulator/Wurster, the water-insoluble polymer coating liquid (330.0 g) was sprayed at spray air pressure 0.4 MPa, spray air flow rate 60 NL/min, inlet air temperature 43° C., inlet air flow rate 0.5 m$^3$/min, spray liquid feed rate 2-3 g/min to give particles after spraying (316.7 g). To 228.0 g of the particles after spraying were added talc (1.2 g), and they were mixed well in a plastic bag, and dried and cured in Forced Convection Constant Temperature Oven (DNF400, manufactured by Yamato Scientific co., ltd., hereinafter the same) at 60° C. for 12 hr. The particles after drying and curing were screened with an aperture 300 μm sieve to give sieved particles, water-insoluble polymer-coated particles (220.9 g).

[Preparation of Orally Disintegrating Tablet Containing Water-Insoluble Polymer-Coated Particles]

In the following, unless particularly described, the content of compound A in the particles obtained in advance in a preliminary step before preparation of a mixture for tableting was measured by HPLC, the amount of the particles prepared in the preliminary step which is required for 20 mg of compound A as a free base to be contained per tablet was calculated and used in the blending step.

The water-insoluble polymer-coated particles (650.9 mg), excipient for direct compression of ODT (SmartEX QD-100, manufactured by Shin-Etsu Chemical Co., Ltd., hereinafter the same) (416.1 mg), aspartame (manufactured by Ajinomoto Co., Inc., hereinafter the same) (11 mg), l-menthol (manufactured by THE SUZUKI MENTHOL CO., LTD., hereinafter the same) (2.75 mg), acesulfame potassium (Sunett manufactured by MC Food Specialties Inc, hereinafter the same) (2.75 mg), sodium stearyl fumarate (PRUV, manufactured by JRS Pharma, hereinafter the same) (16.5 mg), and crystalline cellulose (CEOLUS KG-802, manufactured by Asahi Kasei Corporation) (275 mg) were blended by shaking 100 times in a glass bottle to give a blended product containing the water-insoluble polymer-coated particles. The blended product containing the water-insoluble polymer-coated particles (250 mg) was weighed, tableted using φ8.5 mm flat punch and a single punch tableting machine (HANDTAB-200, manufactured by ICHIHASHI SEIKI, hereinafter the same) at 3 kN to give an orally disintegrating tablet containing the water-insoluble polymer-coated particles (corresponding to 20 mg of compound A as a free base per tablet).

Example 2

[Preparation of Compound a Coating Liquid]

In purified water (399.8 g) was dissolved hydroxypropylmethylcellulose 2910 (24.21 g) to give a hydroxypropylmethylcellulose solution. Successively, compound A (180.0 g)

was uniformly dispersed in the hydroxypropylmethylcellulose solution to give a compound A coating liquid.
[Preparation of Organic Acid Coating Liquid]
In purified water (673.9 g) was dissolved hydroxypropylmethylcellulose 2910 (33.59 g) to give a hydroxypropylmethylcellulose solution. Successively, fumaric acid (100.8 g) jet milled in advance was suspended in the hydroxypropylmethylcellulose solution to give an organic acid coating liquid.
[Preparation of Organic Acid-Coated Particles]
Lactose/crystalline cellulose spherical granules (300.0 g) were placed and fluidized in a fine particle coater granulator/Wurster, and the compound A coating liquid (555.0 g) was sprayed at spray air pressure 0.5 MPa, spray air flow rate 60 NL/min, inlet air temperature 74° C., inlet air flow rate 0.5 m$^3$/min, spray liquid feed rate 6-7 g/min. Successively, the organic acid coating liquid (620.0 g) was sprayed at spray air pressure 0.50 MPa, spray air flow rate 60 NL/min, inlet air temperature 74-85° C., inlet air flow rate 0.5 m$^3$/min, spray liquid feed rate 5-6 g/min and the particles were dried to give particles after drying (542.5 g). The total amount of the particles after drying was sieved to give organic acid-coated particles (300 μm-105 μm) (505.3 g).
[Preparation of Water-Insoluble Polymer Coating Liquid]
In purified water (363.8 g) were suspended and dissolved triacetin (5.98 g), talc (30.2 g), and red ferric oxide (0.2000 g), and the mixture was added to stirring aminoalkylmethacrylate copolymer RS (Eudragit RS30D, manufactured by Evonik) (200.0 g) to give a water-insoluble polymer coating liquid.
[Preparation of Water-Insoluble Polymer-Coated Particles]
The organic acid-coated particles (300 μm-105 μm) (300.3 g) were placed and fluidized in a fine particle coater granulator/Wurster, and the water-insoluble polymer coating liquid (375.0 g) was sprayed at spray air pressure 0.5 MPa, spray air flow rate 60 NL/min, inlet air temperature 40° C., inlet air flow rate 0.5 m$^3$/min, spray liquid feed rate 2-4 g/min to give particles after spraying (331.7 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles (325.0 g).
[Preparation of Outer Layer Granules]
In purified water (315.0 g) was dissolved D-mannitol (14.99 g) to give a binder. D-mannitol (394.8 g), crystalline cellulose (CEOLUS KG-802, manufactured by Asahi Kasei Corporation) (60.28 g), low-substituted hydroxypropylcellulose (L-HPC LH-33, manufactured by Shin-Etsu Chemical Co., Ltd., hereinafter the same) (59.95 g), and crospovidone (Polyplasdone XL-10, manufactured by ISP) (30.22 g) were fed and fluidized in a fluid bed dryer granulator, and the binder (198.0 g) was sprayed at spray air pressure 0.1 MPa, spray air flow rate 60 NL/min, inlet air temperature 85° C., inlet air flow rate 0.2 m$^3$/min, spray liquid feed rate 6 g/min, and the granules were dried. The dried granules were screened with an aperture 850 μm sieve to give sieved particles, outer layer granules (519.8 g).
[Preparation of Orally Disintegrating Tablet Containing Water-Insoluble Polymer-Coated Particles]
The water-insoluble polymer-coated particles (1153.8 mg), the outer layer granules (2446.1 mg), aspartame (21.0 mg), l-menthol (13.1 mg), acesulfame potassium (5.3 mg), sodium stearyl fumarate (31.5 mg), strawberry flavor (4.2 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, and tableted using φ10.0 mm flat punch, a single punch tableting machine at 6 kN to give an orally disintegrating tablet containing the water-insoluble polymer-coated particles (corresponding to 20 mg of compound A as a free base per tablet).

Example 3

[Preparation of Water-Insoluble Polymer-Coated Particles]
In the preparation step of the water-insoluble polymer-coated particles of Example 2, sampling was performed at the time point of spraying the water-insoluble polymer coating liquid (225.0 g) to give particles after spraying (3.4 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.
[Preparation of Orally Disintegrating Tablet Containing Water-Insoluble Polymer-Coated Particles]
The water-insoluble polymer-coated particles (1076.9 mg), the outer layer granules (2523.0 mg) obtained in Example 2, aspartame (21.0 mg), l-menthol (13.1 mg), acesulfame potassium (5.3 mg), sodium stearyl fumarate (31.5 mg), strawberry flavor (4.2 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, tableted with a φ10.0 mm flat punch and a single punch tableting machine at 6 kN to give an orally disintegrating tablet containing the water-insoluble polymer-coated particles (corresponding to 20 mg of compound A as a free base per tablet).

Example 4

[Preparation of Water-Insoluble Polymer-Coated Particles]
In the preparation step of the water-insoluble polymer-coated particles Example 2, sampling was performed at the time point of spraying the water-insoluble polymer coating liquid (300.0 g) to give particles after spraying (3.0 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.
[Preparation of Orally Disintegrating Tablet Containing Water-Insoluble Polymer-Coated Particles]
The water-insoluble polymer-coated particles (1123.0 mg), the outer layer granules (2476.9 mg) obtained in Example 2, aspartame (21.0 mg), l-menthol (13.1 mg), acesulfame potassium (5.3 mg), sodium stearyl fumarate (31.5 mg), strawberry flavor (4.2 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, tableted using a φ10.0 mm flat punch and a single punch tableting machine at 6 kN to give an orally disintegrating tablet containing the water-insoluble polymer-coated particles (corresponding to 20 mg of compound A as a free base per tablet).

Example 5

[Preparation of Water-Insoluble Polymer-Coated Particles]
In the preparation step of the water-insoluble polymer-coated particles of Example 2, sampling was performed at the time point of spraying the water-insoluble polymer coating liquid (330.0 g) to give particles after spraying (3.5 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.
[Preparation of Orally Disintegrating Tablet Containing Water-Insoluble Polymer-Coated Particles]
The water-insoluble polymer-coated particles (1141.3 mg), the outer layer granules (2458.6 mg) obtained in Example 2, aspartame (21.0 mg), 1-menthol (13.1 mg), acesulfame potassium (5.3 mg), sodium stearyl fumarate (31.5 mg), strawberry flavor (4.2 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, tableted using a ϕ10.0 mm flat punch and a single punch tableting machine at 6 kN to give an orally disintegrating tablet containing the water-insoluble polymer-coated particles (corresponding to 20 mg of compound A as a free base per tablet).

Example 6

[Preparation of Compound a Coating Liquid]
In purified water (479.75 g) was dissolved hydroxypropylmethylcellulose 2910 (28.76 g) to give a hydroxypropylmethylcellulose solution. Successively, compound A (215.6 g) was uniformly dispersed in the hydroxypropylmethylcellulose solution to give a compound A coating liquid.
[Preparation of Organic Acid Coating Liquid]
In purified water (864.70 g) was dissolved hydroxypropylmethylcellulose 2910 (43.24 g) to give a hydroxypropylmethylcellulose solution. Successively, fumaric acid (216.3 g) jet milled in advance was suspended in the hydroxypropylmethylcellulose solution to give an organic acid coating liquid.
[Preparation of Organic Acid-Coated Particles]
Lactose/crystalline cellulose spherical granules (350.8 g) were placed and fluidized in a fine particle coater granulator/Wurster, and the compound A coating liquid (642.0 g) was sprayed at spray air pressure 0.5 MPa, spray air flow rate 60 NL/min, inlet air temperature 65-72° C., inlet air flow rate 0.5 m³/min, spray liquid feed rate 5-8 g/min. Successively, the organic acid coating liquid (925.0 g) was sprayed at spray air pressure 0.5 MPa, spray air flow rate 60 NL/min, inlet air temperature 81-82° C., inlet air flow rate 0.5 m³/min, spray liquid feed rate 6-7 g/min and the particles were dried to give particles after drying (722.4 g). The total amount of the particles after drying was sieved to give organic acid-coated particles (300 μm-105 μm) (664.4 g).
[Preparation of Dissolution Controlling Substance Coating Liquid]
In purified water (1851.3 g) were dissolved hydroxypropylmethylcellulose 2910 (30.4 g), succinic acid (119.98 g) to give a dissolution controlling substance coating liquid.

[Preparation of Dissolution Controlling Substance-Coated Particles]
The organic acid-coated particles (300 μm-105 μm) (340.0 g) were placed and fluidized in a fine particle coater granulator/Wurster, and the dissolution controlling substance coating liquid (1295 g) was sprayed at spray air pressure 0.5 MPa, spray air flow rate 60 NL/min, inlet air temperature 85° C., inlet air flow rate 0.5 m³/min, spray liquid feed rate 4-5 g/min and the particles were dried to give particles after drying (415.2 g). The total amount of the particles after drying was sieved to give dissolution controlling substance-coated particles (355 μm-105 μm) (412.3 g).
[Preparation of Water-Insoluble Polymer Coating Liquid]
In purified water (363.9 g) were suspended and dissolved triacetin (5.98 g), talc (30.15 g), and red ferric oxide (0.2131 g), and the mixture was added to stirring aminoalkylmethacrylate copolymer RS (Eudragit RS30D, manufactured by Evonik) (200.2 g) to give a water-insoluble polymer coating liquid.
[Preparation of Water-Insoluble Polymer-Coated Particles]
The dissolution controlling substance-coated particles (355 μm-105 μm) (400.5 g) were placed and fluidized in a fine particle coater granulator/Wurster, and sampling was performed at a time point when the water-insoluble polymer coating liquid (250.0 g) was sprayed at spray air pressure 0.5 MPa, spray air flow rate 60 NL/min, inlet air temperature 43° C., inlet air flow rate 0.5 m³/min, spray liquid feed rate 5 g/min to give particles after spraying (39.9 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.
[Preparation of Orally Disintegrating Tablet Containing Water-Insoluble Polymer-Coated Particles]
The water-insoluble polymer-coated particles (1478.9 mg), the outer layer granules (2121.1 mg) obtained in Example 2, aspartame (21.0 mg), 1-menthol (13.1 mg), acesulfame potassium (5.3 mg), sodium stearyl fumarate (31.5 mg), strawberry flavor (4.2 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, tableted using a ϕ10.0 mm flat punch and a single punch tableting machine at 6 kN to give an orally disintegrating tablet containing the water-insoluble polymer-coated particles (corresponding to 20 mg of compound A as a free base per tablet).

Example 7

[Preparation of Compound a Coating Liquid]
In purified water (480.0 g) was dissolved hydroxypropylmethylcellulose 2910 (28.8 g) to give a hydroxypropylmethylcellulose solution. Successively, compound A (216.1 g) was uniformly dispersed in the hydroxypropylmethylcellulose solution to give a compound A coating liquid.
[Preparation of Organic Acid Coating Liquid]
In purified water (864.0 g) was dissolved hydroxypropylmethylcellulose 2910 (43.2 g) to give a hydroxypropylmethylcellulose solution. Successively, fumaric acid (216.1 g) jet milled in advance was suspended in the hydroxypropylmethylcellulose solution to give an organic acid coating liquid.

[Preparation of Organic Acid-Coated Particles]

Lactose/crystalline cellulose spherical granules (349.8 g) were placed and fluidized in a fine particle coater granulator/Wurster, and the compound A coating liquid (642.0 g) was sprayed at spray air pressure 0.5 MPa, spray air flow rate 60 NL/min, inlet air temperature 73° C., inlet air flow rate 0.5 m³/min, spray liquid feed rate 6-8 g/min. Successively, the organic acid coating liquid (925.0 g) was sprayed at spray air pressure 0.5 MPa, spray air flow rate 60 NL/min, inlet air temperature 80° C., inlet air flow rate 0.5 m³/min, spray liquid feed rate 5-8 g/min and the particles were dried to give particles after drying (714.8 g). The total amount of the particles after drying was sieved to give organic acid-coated particles (355 μm-105 μm) (686.4 g).

[Preparation of Dissolution Controlling Substance Coating Liquid]

In purified water (1387.5 g) were dissolved hydroxypropylmethylcellulose 2910 (22.5 g), succinic acid (89.96 g) to give a dissolution controlling substance coating liquid.

[Preparation of Dissolution Controlling Substance-Coated Particles]

The organic acid-coated particles (355 μm-105 μm) (329.8 g) were placed and fluidized in a fine particle coater granulator/Wurster, and the dissolution controlling substance coating liquid (1257.0 g) was sprayed at spray air pressure 0.5 MPa, spray air flow rate 60 NL/min, inlet air temperature 85° C., inlet air flow rate 0.5 m³/min, spray liquid feed rate 4-5 g/min and the particles were dried to give particles after drying (401.2 g). The total amount of the particles after drying was sieved to give dissolution controlling substance-coated particles (355 μm sieved granule).

[Preparation of Water-Insoluble Polymer Coating Liquid]

In purified water (499.7 g) was dissolved polysorbate 80 (manufactured by Merck) (0.4071 g), and then talc (25.09 g), red ferric oxide (0.2000 g) were added and the mixture was uniformly dispersed to give a suspension. The suspension was added by small portions to stirring aminoalkylmethacrylate copolymer RS (Eudragit RS30D, manufactured by Evonik) (142.1 g). In separately prepared purified water (500.6 g) was dissolved citric anhydride (0.0779 g) and the solution was added by small portions to ethyl acrylate-methyl methacrylate copolymer dispersion (Eudragit NE30D, manufactured by Evonik) (25.1 g) and the mixture was stirred well. To the former liquid containing aminoalkylmethacrylate copolymer RS (Eudragit RS30D, manufactured by Evonik) was added by small portions a solution containing ethyl acrylate-methyl methacrylate copolymer dispersion and the mixture was stirred well to give a water-insoluble polymer coating liquid.

[Preparation of Water-Insoluble Polymer-Coated Particles]

The dissolution controlling substance-coated particles (355 μm sieved granule) (350.0 g) were placed and fluidized in a fine particle coater granulator/Wurster, and the water-insoluble polymer coating liquid (751.0 g) was sprayed at spray air pressure 0.5 MPa, spray air flow rate 60 NL/min, inlet air temperature 40-46° C., inlet air flow rate 0.5-0.6 m³/min, spray liquid feed rate 2-3 g/min to give particles after spraying (321.7 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.

[Preparation of Orally Disintegrating Tablet Containing Water-Insoluble Polymer-Coated Particles]

The water-insoluble polymer-coated particles (1598.2 mg), the outer layer granules (2013.8 mg) obtained in Example 2, aspartame (21.0 mg), l-menthol (5.3 mg), acesulfame potassium (5.3 mg), sodium stearyl fumarate (31.5 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (400 mg) was weighed, tableted using a ϕ10.0 mm flat punch and a single punch tableting machine at 6 kN to give an orally disintegrating tablet containing the water-insoluble polymer-coated particles (corresponding to 20 mg of compound A as a free base per tablet).

Example 8

[Preparation of Compound a Coating Liquid]

In purified water (399.7 g) was dissolved hydroxypropylmethylcellulose 2910 (23.98 g) to give a hydroxypropylmethylcellulose solution. Successively, compound A (179.7 g) was uniformly dispersed in the hydroxypropylmethylcellulose solution to give a compound A coating liquid.

[Preparation of Organic Acid Coating Liquid (1)]

In purified water (324.8 g) was dissolved hydroxypropylmethylcellulose 2910 (12.53 g) to give a hydroxypropylmethylcellulose solution. Successively, fumaric acid (50.15 g) jet milled in advance was suspended in the hydroxypropylmethylcellulose solution to give an organic acid coating liquid.

[Preparation of Organic Acid-Coated Particles (1)]

Lactose/crystalline cellulose spherical granules (450.4 g) were placed and fluidized in a fine particle coater granulator/Wurster, and the compound A coating liquid (522.0 g) was sprayed at spray air pressure 0.5 MPa, spray air flow rate 60 NL/min, inlet air temperature 75° C., inlet air flow rate 0.5 m³/min, spray liquid feed rate 6 g/min. Successively, the organic acid coating liquid (1) (222.0 g) was sprayed at spray air pressure 0.5 MPa, spray air flow rate 60 NL/min, inlet air temperature 85° C., inlet air flow rate 0.5-0.6 m³/min, spray liquid feed rate 6-7 g/min, and the particles were dried to give particles after drying (631.0 g). The total amount of the particles after drying was sieved to give organic acid-coated particles (1) (355 μm-105 μm) (623.6 g).

[Preparation of Dissolution Controlling Substance Coating Liquid]

In purified water (1540.2 g) were dissolved hydroxypropylmethylcellulose 2910 (33.25 g), succinic acid (84.11 g) to give a dissolution controlling substance coating liquid.

[Preparation of Organic Acid Coating Liquid (2)]

In purified water (416.3 g) was dissolved hydroxypropylmethylcellulose 2910 (16.20 g) to give a hydroxypropylmethylcellulose solution. Successively, fumaric acid (64.15 g) jet milled in advance was suspended in the hydroxypropylmethylcellulose solution to give an organic acid coating liquid (2).

[Preparation of Organic Acid-Coated Particles (2)]

The organic acid-coated particles (1) (355 μm-105 μm) (320.1 g) were placed and fluidized in a fine particle coater granulator/Wurster, and the dissolution controlling substance coating liquid (1375.0 g) was sprayed at spray air pressure 0.5 MPa, spray air flow rate 60 NL/min, inlet air temperature 85° C., inlet air flow rate 0.5-0.6 m³/min, spray liquid feed rate 4-5 g/min. Successively, the organic acid coating liquid (2) (420.0 g) was sprayed at spray air pressure 0.5 MPa, spray air flow rate 60 NL/min, inlet air temperature 80° C., inlet air flow rate 0.6 m³/min, spray liquid feed rate 5-6 g/min and the particles were dried to give particles after drying (446.0 g). The total amount of the particles after drying was sieved to give organic acid-coated particles (2) (355 μm-125 μm) (402.5 g).

[Preparation of Water-Insoluble Polymer Coating Liquid]

In purified water (545.1 g) were suspended and dissolved triacetin (9.0 g), talc (45.10 g), and red ferric oxide (0.9215 g) was added. The mixture was added to stirring aminoalkylmethacrylate copolymer RS (Eudragit RS30D, manufactured by Evonik) (300.1 g) to give a water-insoluble polymer coating liquid.

[Preparation of Water-Insoluble Polymer-Coated Particles]

The organic acid-coated particles (2) (355 μm-125 μm) (399.8 g) were placed and fluidized in a fine particle coater granulator/Wurster, and sampling was performed at a time point when the water-insoluble polymer coating liquid (307.0 g) was sprayed at spray air pressure 0.3-0.5 MPa, spray air flow rate 60 NL/min, inlet air temperature 35-43° C., inlet air flow rate 0.5-0.6 m$^3$/min, spray liquid feed rate of 2-3 g/min to give particles after spraying (20.4 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles.

[Preparation of Orally Disintegrating Tablet Containing Water-Insoluble Polymer-Coated Particles]

The water-insoluble polymer-coated particles (3510.3 mg), the outer layer granules (5550.7 mg) obtained in Example 2, aspartame (82.0 mg), 1-menthol (10.3 mg), acesulfame potassium (10.3 mg), sodium stearyl fumarate (61.5 mg), and crystalline cellulose (CEOLUS KG-802, manufactured by Asahi Kasei Corporation) (1025.0 mg) were blended by shaking 100 times in a glass bottle to give a blended product containing the water-insoluble polymer-coated particles. The blended product containing the water-insoluble polymer-coated particles (500 mg) was weighed, tableted using a ϕ11.0 mm flat punch and a single punch tableting machine at 6 kN to give an orally disintegrating tablet containing the water-insoluble polymer-coated particles (corresponding to 20 mg of compound A as a free base per tablet).

Example 9

[Preparation of Compound a Coating Liquid]

In purified water (700.0 g) was dissolved hydroxypropylmethylcellulose 2910 (18.04 g) to give a hydroxypropylmethylcellulose solution. Successively, compound A (180.0 g) was uniformly dispersed in the hydroxypropylmethylcellulose solution to give a compound A coating liquid.

[Preparation of Organic Acid Coating Liquid (1)]

In purified water (399.7 g) was dissolved hydroxypropylmethylcellulose 2910 (12.49 g) to give a hydroxypropylmethylcellulose solution. Successively, fumaric acid (50.12 g) jet milled in advance was suspended in the hydroxypropylmethylcellulose solution to give an organic acid coating liquid (1).

[Preparation of Organic Acid-Coated Particles (1)]

Partly pregelatinized starch (PCS PC-10, manufactured by Asahi Kasei Corporation, hereinafter the same) (310.1 g) classified (D$_{50}$=116.4 μm) using a 75 μm sieve with aperture 180 were placed and fluidized in a fine particle coater granulator/Wurster, and the compound A coating liquid (830.0 g) was sprayed at spray air pressure 0.3 MPa, spray air flow rate 60 NL/min, inlet air temperature 83° C., inlet air flow rate 0.5-0.6 m$^3$/min, spray liquid feed rate 3-7 g/min. Successively, the organic acid coating liquid (1) (290.0 g) was sprayed at spray air pressure 0.3 MPa, spray air flow rate 60 NL/min, inlet air temperature 73-83° C., inlet air flow rate 0.6 m$^3$/min, spray liquid feed rate 5-6 g/min and the particles were dried to give particles after drying (476.5 g). The total amount of the particles after drying was sieved to give organic acid-coated particles (1) (180 μm-75 μm) (356.8 g).

[Preparation of Dissolution Controlling Substance Coating Liquid]

In purified water (1540.0 g) were dissolved hydroxypropylmethylcellulose 2910 (33.25 g), succinic acid (84.01 g) to give a dissolution controlling substance coating liquid.

[Preparation of Dissolution Controlling Substance-Coated Particles]

The organic acid-coated particles (1) (180 μm-75 μm) (300.0 g) were placed and fluidized in a fine particle coater granulator/Wurster, and the dissolution controlling substance coating liquid (1620.0 g) was sprayed at spray air pressure 0.4 MPa, spray air flow rate 60 NL/min, inlet air temperature 84-85° C., inlet air flow rate 0.5-0.6 m$^3$/min, spray liquid feed rate 4 g/min and the particles were dried to give particles after drying (396.8 g). The total amount of the particles after drying was sieved to give dissolution controlling substance-coated particles (212 μm-75 μm) (357.8 g).

[Preparation of Organic Acid Coating Liquid (2)]

In purified water (640.0 g) was dissolved hydroxypropylmethylcellulose 2910 (17.02 g) to give a hydroxypropylmethylcellulose solution. Successively, fumaric acid (80.1 g) jet milled in advance was suspended in the hydroxypropylmethylcellulose solution to give organic acid coating liquid (2).

[Preparation of Organic Acid-Coated Particles (2)]

The dissolution controlling substance-coated particles (212 μm-75 μm) (349.0 g) were placed and fluidized in a fine particle coater granulator/Wurster, the organic acid coating liquid (2) (540.0 g) was sprayed at spray air pressure 0.4 MPa, spray air flow rate 60 NL/min, inlet air temperature 85° C., inlet air flow rate 0.5 m$^3$/min, spray liquid feed rate 4 g/min and the particles were dried to give particles after drying (396.1 g). The total amount of the particles after drying was sieved to give organic acid-coated particles (2) (250 μm-75 μm) (390.0 g).

[Preparation of Water-Insoluble Polymer Coating Liquid (1)]

In purified water (272.5 g) were suspended and dissolved triacetin (4.5 g), talc (22.5 g), and red ferric oxide (0.4452 g), and the mixture was added to stirring aminoalkylmethacrylate copolymer RS (Eudragit RS30D, manufactured by Evonik) (150.0 g) to give water-insoluble polymer coating liquid (1).

[Preparation of Water-Insoluble Polymer-Coated Particles (1)]

The organic acid-coated particles (2) (250 μm-105 μm) (350.0 g) were placed and fluidized in a fine particle coater granulator/Wurster, and the water-insoluble polymer coating liquid (1) (315.0 g) was sprayed at spray air pressure 0.3 MPa, spray air flow rate 60 NL/min, inlet air temperature 38° C., inlet air flow rate 0.5-0.6 m$^3$/min, spray liquid feed rate 2-3 g/min to give particles after spraying (340.5 g). Successively, the particles after spraying were dried and cured in Forced Convection Constant Temperature Oven at 60° C. for 14 hr. The particles after drying and curing were screened with an aperture 250 μm sieve to give sieved particles, water-insoluble polymer-coated particles (1).

[Preparation of Water-Insoluble Polymer Coating Liquid (2)]

In purified water (361.2 g) were suspended and dissolved triacetin (2.31 g), talc (11.26 g), and red ferric oxide (0.2253 g), and the mixture was added to stirring aminoalkylmethacrylate copolymer RS (Eudragit RS30D, manufactured by Evonik) (75.1 g) to give a water-insoluble polymer coating liquid (2).

[Preparation of Water-Insoluble Polymer-Coated Particles (2)]

The water-insoluble polymer-coated particles (1) (314.8 g) were placed and fluidized in a fine particle coater granulator/Wurster, and the water-insoluble polymer coating liquid (2) (200.0 g) was sprayed at spray air pressure 0.3 MPa, spray air flow rate 60 NL/min, inlet air temperature 35-38° C., inlet air flow rate 0.6 m$^3$/min, spray liquid feed rate 2-3 g/min to give particles after spraying (251.5 g). Successively, the particles after spraying were dried and cured in Forced Convection Constant Temperature Oven at 60° C. for 14 hr. The particles after drying and curing were screened with an aperture 350 μm sieve to give sieved particles, water-insoluble polymer-coated particles (2).

[Preparation of Orally Disintegrating Tablet Containing Water-Insoluble Polymer-Coated Particles]

The water-insoluble polymer-coated particles (2) (1584.9 mg), the outer layer granules (1901.1 mg) obtained in Example 2, aspartame (42.0 mg), sodium stearyl fumarate (42.0 mg), monosodium fumarate (Wako primary, manufactured by Wako Pure Chemical Industries, Ltd.) (105.0 mg), and partly pregelatinized starch (525.0 mg) were blended by shaking 100 times in a glass bottle to give a blended product containing the water-insoluble polymer-coated particles (2). The blended product containing the water-insoluble polymer-coated particles (2) (400 mg) was weighed, and tableted using a ϕ10.0 mm flat punch and a single punch tableting machine at 6 kN to give an orally disintegrating tablet containing the water-insoluble polymer-coated particles (2) (corresponding to 20 mg of compound A as a free base per tablet).

Example 10

[Preparation of Compound a Coating Liquid]

In purified water (449.98 g) was dissolved hydroxypropylmethylcellulose 2910 (16.80 g) to give a hydroxypropylmethylcellulose solution. Successively, compound A (126.1 g) was uniformly dispersed in the hydroxypropylmethylcellulose solution to give a compound A coating liquid.

[Preparation of Organic Acid Coating Liquid]

In purified water (2609.9 g) was dissolved hydroxypropylmethylcellulose 2910 (62.64 g) to give a hydroxypropylmethylcellulose solution. Successively, fumaric acid (313.2 g) jet milled in advance was suspended in the hydroxypropylmethylcellulose solution to give an organic acid coating liquid.

[Preparation of Organic Acid-Coated Particles]

Lactose/crystalline cellulose spherical granules (300.0 g) were placed and fluidized in a fine particle coater granulator/Wurster, and the compound A coating liquid (490.0 g) was sprayed at spray air pressure 0.3 MPa, spray air flow rate 60 NL/min, inlet air temperature 73° C., inlet air flow rate 0.6 m$^3$/min, spray liquid feed rate 5-6 g/min. Successively, the organic acid coating liquid (2750.0 g) was sprayed at spray air pressure 0.3 MPa, spray air flow rate 60-70 NL/min, inlet air temperature 78-80° C., inlet air flow rate 0.6 m$^3$/min, spray liquid feed rate 6-7 g/min and the particles were dried to give particles after drying (659.4 g). The total amount of the particles after drying was sieved to give organic acid-coated particles (355 μm-105 μm) (604.5 g).

[Preparation of Dissolution Controlling Substance Coating liquid]

In purified water (1300.15 g) were dissolved methylcellulose (28.12 g), succinic acid (84.31 g) to give a dissolution controlling substance coating liquid.

[Preparation of Dissolution Controlling Substance-Coated Particles]

The organic acid-coated particles (355 μm-105 μm) (300.4 g) were placed and fluidized in a fine particle coater granulator/Wurster, the dissolution controlling substance coating liquid (1190.0 g) was sprayed at spray air pressure 0.3 MPa, spray air flow rate 60 NL/min, inlet air temperature 83° C., inlet air flow rate 0.6 m$^3$/min, spray liquid feed rate 3-5 g/min and the particles were dried to give particles after drying (384.3 g). The total amount of the particles after drying was sieved to give dissolution controlling substance-coated particles (355 μm-125 μm) (372.9 g).

[Preparation of Water-Insoluble Polymer Coating Liquid]

In purified water (272.5 g) were suspended and dissolved triacetin (4.50 g), talc (22.48 g), and yellow ferric oxide (LCW, hereinafter the same) (0.4532 g), and the mixture was added to stirring aminoalkylmethacrylate copolymer RS (Eudragit RS30D, manufactured by Evonik) (150.1 g) to give a water-insoluble polymer coating liquid.

[Preparation of Water-Insoluble Polymer-Coated Particles]

The dissolution controlling substance-coated particles (355 μm-125 μm) (360.1 g) were placed and fluidized in a fine particle coater granulator/Wurster, and the water-insoluble polymer coating liquid (200.0 g) was sprayed at spray air pressure 0.2 MPa, spray air flow rate 60 NL/min, inlet air temperature 36° C., inlet air flow rate 0.6 m$^3$/min, spray liquid feed rate 2-3 g/min to give particles after spraying (372.2 g). Successively, the particles after spraying were dried and cured in Forced Convection Constant Temperature Oven at 60° C. for 14 hr. The particles after drying and curing were screened with an aperture 355 μm sieve to give sieved particles, water-insoluble polymer-coated particles.

[Preparation of Outer Layer Granules]

In purified water (314.8 g) were dissolved D-mannitol (31.59 g), and citric anhydride (21.35 g) to give a binder. D-mannitol (383.4 g), crystalline cellulose (CEOLUS KG-802, manufactured by Asahi Kasei Corporation) (59.64 g), low-substituted hydroxypropylcellulose (59.96 g), and crospovidone (Polyplasdone XL-10, manufactured by ISP) (30.23 g) were fed and fluidized in a fluid bed dryer granulator, and the binder (210.0 g) was sprayed at spray air pressure 0.1 MPa, spray air flow rate 60 NL/min, inlet air temperature 85° C., inlet air flow rate 0.2-0.3 m$^3$/min, spray liquid feed rate 11 g/min, and the granules were dried. The dried granules were screened with an aperture 850 μm sieve to give sieved granules, outer layer granules (526.6 g).

[Preparation of Orally Disintegrating Tablet Containing Water-Insoluble Polymer-Coated Particles]

The water-insoluble polymer-coated particles (2573.5 mg), the outer layer granules (2566.2 mg), aspartame (63.0 mg), orange flavor (San fix orange, manufactured by San-Ei Gen F.F.I., Inc., hereinafter the same) (5.3 mg), sodium stearyl fumarate (42.0 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (550.0 mg) was weighed, and tableted using a ϕ11.5 mm flat punch and a single punch tableting machine at 6 kN to give an orally disintegrating tablet containing the water-insoluble polymer-coated particles (corresponding to 20 mg of compound A as a free base per tablet).

Example 11

[Preparation of Compound a Coating Liquid]

In purified water (450.21 g) was dissolved hydroxypropylmethylcellulose 2910 (16.83 g) to give a hydroxypropylmethylcellulose solution. Successively, compound A (126.3 g) was uniformly dispersed in the hydroxypropylmethylcellulose solution to give a compound A coating liquid.

[Preparation of Organic Acid Coating Liquid]

In purified water (3330.1 g) was dissolved hydroxypropylmethylcellulose 2910 (79.92 g) to give a hydroxypropylmethylcellulose solution. Successively, fumaric acid (399.6 g) jet milled in advance was suspended in the hydroxypropylmethylcellulose solution to give an organic acid coating liquid.

[Preparation of Dissolution Controlling Substance Coating Liquid]

In purified water (1300.0 g) were dissolved methylcellulose (28.1 g), succinic acid (84.0 g) to give a dissolution controlling substance coating liquid.

[Preparation of Organic Acid-Coated Particles]

Lactose/crystalline cellulose spherical granules (300.0 g) were placed and fluidized in a fine particle coater granulator/Wurster, and the compound A coating liquid (490.0 g) was sprayed at spray air pressure 0.3 MPa, spray air flow rate 80 NL/min, inlet air temperature 83° C., inlet air flow rate 0.6 m$^3$/min, spray liquid feed rate 5-6 g/min. Successively, the organic acid coating liquid (2920.0 g) was sprayed at spray air pressure 0.3 MPa, spray air flow rate 70 NL/min, inlet air temperature 80° C., inlet air flow rate 0.6 m$^3$/min, spray liquid feed rate 5-6 g/min and the particles were dried to give particles after drying (730.9 g). The total amount of the particles after drying was sieved to give organic acid-coated particles (355 μm-105 μm) (726.5 g).

[Preparation of Dissolution Controlling Substance-Coated Particles]

The organic acid-coated particles (355 μm-105 μm) (360.1 g) were placed and fluidized in a fine particle coater granulator/Wurster, and the organic acid coating liquid (357.0 g) was sprayed at spray air pressure 0.3 MPa, spray air flow rate 70 NL/min, inlet air temperature 80° C., inlet air flow rate 0.6 m$^3$/min, spray liquid feed rate 4-5 g/min. Successively, the dissolution controlling substance coating liquid (750.0 g) was sprayed at spray air pressure 0.3 MPa, spray air flow rate 70 NL/min, inlet air temperature 80° C., inlet air flow rate 0.6 m$^3$/min, spray liquid feed rate 2-4 g/min, and the particles were dried to give particles after drying (443.0 g). The total amount of the particles after drying was sieved to give dissolution controlling substance-coated particles (355 μm-125 μm) (433.0 g).

[Preparation of Water-Insoluble Polymer Coating Liquid]

In purified water (272.5 g) were suspended and dissolved in triacetin (4.50 g), talc (22.51 g), and yellow ferric oxide (0.4503 g), and the mixture was added to stirring aminoalkylmethacrylate copolymer RS (Eudragit RS30D, manufactured by Evonik) (150.3 g) to give a water-insoluble polymer coating liquid.

[Preparation of Water-Insoluble Polymer-Coated Particles]

The dissolution controlling substance-coated particles (355 μm-125 μm) (420.3 g) were placed and fluidized in a fine particle coater granulator/Wurster, and the water-insoluble polymer coating liquid (238.0 g) was sprayed at spray air pressure 0.2 MPa, spray air flow rate 70 NL/min, inlet air temperature 36° C., inlet air flow rate 0.6-0.7 m$^3$/min, spray liquid feed rate 2 g/min to give particles after spraying (426.9 g). Successively, the particles after spraying were dried and cured in Forced Convection Constant Temperature Oven at 60° C. for 14 hr. The particles after drying and curing were screened with an aperture 355 μm sieve to give sieved particles, water-insoluble polymer-coated particles.

[Preparation of Orally Disintegrating Tablet Containing Water-Insoluble Polymer-Coated Particles]

The water-insoluble polymer-coated particles (2900.6 mg), the outer layer granules (2449.2 mg) obtained in Example 10, aspartame (63.0 mg), orange flavor (5.3 mg), sodium stearyl fumarate (42.0 mg), and crystalline cellulose (CEOLUS KG-1000, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (570.0 mg) was weighed, and tableted using a φ11.5 mm flat punch and a single punch tableting machine at 6 kN to give an orally disintegrating tablet containing the water-insoluble polymer-coated particles (corresponding to 20 mg of compound A as a free base per tablet).

Example 12 (with Seal Coat)

[Preparation of Compound a Coating Liquid]

In purified water (550.03 g) was dissolved hydroxypropylmethylcellulose 2910 (20.41 g) to give a hydroxypropylmethylcellulose solution. Successively, compound A (153.0 g) was uniformly dispersed in the hydroxypropylmethylcellulose solution to give a compound A coating liquid.

[Preparation of Water-Soluble Polymer Coating Liquid]

In purified water (955.01 g) was dissolved hydroxypropylmethylcellulose 2910 (30.03 g) to give a hydroxypropylmethylcellulose solution. Successively, talc (14.99 g) was suspended to give water-soluble polymer coating liquid.

[Preparation of Organic Acid Coating Liquid]

In purified water (1350.2 g) was dissolved hydroxypropylmethylcellulose 2910 (30.04 g) to give a hydroxypropylmethylcellulose solution. Successively, fumaric acid (162.0 g) jet milled in advance was suspended to give an organic acid coating liquid.

[Preparation of Organic Acid-Coated Particles]

Lactose/crystalline cellulose spherical granules (399.2 g) were placed and fluidized in a fine particle coater granulator/Wurster, and the compound A coating liquid (655.0 g) was sprayed at spray air pressure 0.3 MPa, spray air flow rate 60 NL/min, inlet air temperature 76° C., inlet air flow rate 0.6-0.7 m$^3$/min, spray liquid feed rate 1-7 g/min. The water-soluble polymer coating liquid (400.0 g) was sprayed at spray air pressure 0.3 MPa, spray air flow rate 60 NL/min, inlet air temperature 84° C., inlet air flow rate 0.7 m$^3$/min, spray liquid feed rate 4-6 g/min. The organic acid coating liquid (1233.0 g) was sprayed at spray air pressure 0.3 MPa, spray air flow rate 60 NL/min, inlet air temperature 76° C., inlet air flow rate 0.6-0.7 m$^3$/min, spray liquid feed rate 6 g/min. Successively, the particles were dried to give particles after drying (667.5 g). The total amount of the particles after drying was sieved to give organic acid-coated particles (355 μm-125 μm) (662.5 g).

[Preparation of Dissolution Controlling Substance Coating Liquid]

In purified water (1330.0 g) were dissolved hydroxypropylmethylcellulose 2910 (28.04 g), succinic acid (84.02 g) to give a dissolution controlling substance coating liquid.

[Preparation of Dissolution Controlling Substance-Coated Particles]

The organic acid-coated particles (355 μm-125 μm) (330.0 g) were placed and fluidized in a fine particle coater granulator/Wurster, and the dissolution controlling substance coating liquid (1008.0 g) was sprayed at spray air pressure 0.30 MPa, spray air flow rate 65 NL/min, inlet air temperature 83° C., inlet air flow rate 0.6 m³/min, spray liquid feed rate 4-5 g/min, and the particles were dried to give particles after drying (377.5 g). The total amount of the particles after drying was sieved to give dissolution controlling substance-coated particles (355 μm-125 μm) (376.5 g).

[Preparation of Water-Insoluble Polymer Coating Liquid]

In purified water (273.0 g) were suspended and dissolved triacetin (4.51 g) and talc (22.52 g), and the mixture was added to stirring aminoalkylmethacrylate copolymer RS (Eudragit RS30D, manufactured by Evonik) (150.0 g) to give a water-insoluble polymer coating liquid.

[Preparation of Water-Insoluble Polymer-Coated Particles]

The dissolution controlling substance-coated particles (355 μm-125 μm) (370.0 g) were placed and fluidized in a fine particle coater granulator/Wurster, and the water-insoluble polymer coating liquid (277.0 g) was sprayed at spray air pressure 0.2 MPa, spray air flow rate 65 NL/min, inlet air temperature 36° C., inlet air flow rate 0.6-0.7 m³/min, spray liquid feed rate 2-3 g/min to give particles after spraying (397.1 g). Successively, the particles after spraying were dried and cured in Forced Convection Constant Temperature Oven at 60° C. for 2 hr. The particles after drying and curing were screened with an aperture 355 μm sieve to give sieved particles, water-insoluble polymer-coated particles.

[Preparation of Outer Layer Granules]

In purified water (320.0 g) were dissolved D-mannitol (27.19 g), and citric anhydride (17.24 g) to give a binder. D-mannitol (225.2 g), crystalline cellulose (CEOLUS KG-802, manufactured by Asahi Kasei Corporation) (36.08 g), low-substituted hydroxypropylcellulose (35.18 g), and crospovidone (Polyplasdone XL-10, manufactured by ISP) (17.58 g), β-cyclodextrin (68.80 g) were fed and fluidized in a fluid bed dryer granulator, and the binder (145.6 g) was sprayed at spray air pressure 0.1 MPa, spray air flow rate 60 NL/min, inlet air temperature 85° C., inlet air flow rate 0.2-0.3 m³/min, spray liquid feed rate 6 g/min, and the granules were dried. The dried granules were screened with an aperture 850 μm sieve to give sieved granules, outer layer granules (363.1 g).

[Preparation of Orally Disintegrating Tablet Containing Water-Insoluble Polymer-Coated Particles]

The water-insoluble polymer-coated particles (2042.8 mg), the outer layer granules (3049.7 mg), aspartame (63.0 mg), sodium stearyl fumarate (94.5 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (550.0 mg) was weighed, and tableted using a ϕ11.5 mm flat punch and a single punch tableting machine at 9 kN to give an orally disintegrating tablet containing the water-insoluble polymer-coated particles (corresponding to 20 mg of compound A as a free base per tablet).

Example 13 (with Seal Coat)

[Preparation of Organic Acid Coating Liquid]

In purified water (787.53 g) was dissolved hydroxypropylmethylcellulose 2910 (17.51 g) to give a hydroxypropylmethylcellulose solution. Successively, jet milled in advance fumaric acid (94.5 g) was suspended to give an organic acid coating liquid.

[Preparation of Dissolution Controlling Substance Coating Liquid]

In purified water (1330.0 g) were dissolved hydroxypropylmethylcellulose 2910 (28.03 g), succinic acid (83.98 g) to give a dissolution controlling substance coating liquid.

[Preparation of Dissolution Controlling Substance-Coated Particles]

The organic acid-coated particles (355 μm-125 μm) (330.0 g) obtained in Example 12 were placed and fluidized in a fine particle coater granulator/Wurster, and the organic acid coating liquid (559.4 g) was sprayed at spray air pressure 0.3 MPa, spray air flow rate 65 NL/min, inlet air temperature 76° C., inlet air flow rate 0.6-0.7 m³/min, spray liquid feed rate 3-9 g/min. The dissolution controlling substance coating liquid (1008.0 g) was sprayed at spray air pressure 0.3 MPa, spray air flow rate 65 NL/min, inlet air temperature 76° C., inlet air flow rate 0.6-0.7 m³/min, spray liquid feed rate 4-6 g/min. Successively, the particles were dried to give particles after drying (459.9 g). The total amount of the particles after drying was sieved to give dissolution controlling substance-coated particles (355 μm-125 μm) (451.3 g).

[Preparation of Water-Insoluble Polymer Coating Liquid]

In purified water (273.0 g) were suspended and dissolved triacetin (4.50 g) and talc (22.50 g), and the mixture was added to stirring aminoalkylmethacrylate copolymer RS (Eudragit RS30D, manufactured by Evonik) (150.0 g) to give a water-insoluble polymer coating liquid.

[Preparation of Water-Insoluble Polymer-Coated Particles]

The dissolution controlling substance-coated particles (355 μm-125 μm) (445.0 g) were placed and fluidized in a fine particle coater granulator/Wurster, and the water-insoluble polymer coating liquid (284.5 g) was sprayed at spray air pressure 0.2 MPa, spray air flow rate 70 NL/min, inlet air temperature 34-36° C., inlet air flow rate 0.7 m³/min, spray liquid feed rate 2-3 g/min to give particles after spraying (430.9 g). Successively, the particles after spraying were dried and cured in Forced Convection Constant Temperature Oven at 60° C. for 14 hr. The particles after drying and curing were screened with an aperture 355 μm sieve to give sieved particles, water-insoluble polymer-coated particles.

[Preparation of Coagulation Inhibiting Substance Coating Liquid]

In purified water (450.05 g) was dissolved D-mannitol (50.15 g) to give a coagulation inhibiting substance coating liquid.

[Preparation of Coagulation Inhibiting Substance-Coated Particles]

The water-insoluble polymer-coated particles (415.0 g) were placed and fluidized in a fine particle coater granulator/Wurster, and the coagulation inhibiting substance coating liquid (222.2 g) was sprayed at spray air pressure 0.3 MPa, spray air flow rate 65 NL/min, inlet air temperature 68° C., inlet air flow rate 0.7 m³/min, spray liquid feed rate 4 g/min and the particles were dried to give particles after drying (428.0 g). The total amount of the particles after spraying was screened to give 355 μm-125 μm granules as coagulation inhibiting substance-coated particles (427.5 g).

[Preparation of Orally Disintegrating Tablet Containing Coagulation Inhibiting Substance-Coated Particles]

The coagulation inhibiting substance-coated particles (2545.5 mg), the outer layer granules (2751.8 mg) obtained in Example 12, aspartame (63.0 mg), menthol flavor (menthol cortone HL33855, manufactured by Ogawa & Co., Ltd.) (5.3 mg), sodium stearyl fumarate (94.5 mg), and crystalline cellulose (CEOLUS KG-802, manufactured by Asahi Kasei Corporation) (525.0 mg) were blended by shaking 100 times in a glass bottle to give a blended product containing the coagulation inhibiting substance-coated particles. The blended product containing coagulation inhibiting substance-coated particles (570.0 mg) was weighed, and tableted using a ϕ11.5 mm flat punch and a single punch tableting machine at 9 kN to give an orally disintegrating tablet containing the water-insoluble polymer-coated particles (corresponding to 20 mg of compound A as a free base per tablet).

Example 14

[Preparation of Compound a Coating Liquid]

In purified water (550.0 g) was dissolved hydroxypropylmethylcellulose 2910 (20.41 g) to give a hydroxypropylmethylcellulose solution. Successively, compound A (153.1 g) was uniformly dispersed in the hydroxypropylmethylcellulose solution to give a compound A coating liquid.

[Preparation of Water-Soluble Polymer Coating Liquid]

In purified water (955.0 g) was dissolved hydroxypropylmethylcellulose 2910 (29.70 g) to give a hydroxypropylmethylcellulose solution. Successively, talc (15.00 g) was suspended to give a water-soluble polymer coating liquid.

[Preparation of Water-Soluble Polymer-Coated Particles]

Lactose/crystalline cellulose spherical granules (399.2 g) were placed and fluidized in a fine particle coater granulator/Wurster, and the compound A coating liquid (655.0 g) was sprayed at spray air pressure 0.3 MPa, spray air flow rate 70 NL/min, inlet air temperature 76° C., inlet air flow rate 0.6-0.7 m³/min, spray liquid feed rate 5-7 g/min. A water-soluble polymer coating liquid (520.0 g) was sprayed at spray air pressure 0.3 MPa, spray air flow rate 70 NL/min, inlet air temperature 76° C., inlet air flow rate 0.7 m³/min, spray liquid feed rate 4-5 g/min, the particles were dried to give particles after drying (505.3 g). The total amount of the particles after drying was sieved to give water-soluble polymer-coated particles (355 μm-125 μm) (504.5 g).

[Preparation of Organic Acid Coating Liquid]

To purified water (1530.0 g) were added aminoalkylmethacrylate copolymer E (Eudragit EPO, manufactured by Evonik, hereinafter the same) (19.01 g), and fumaric acid (240.0 g) jet milled in advance was added and the mixture was stirred to give organic acid coating liquid.

[Preparation of Organic Acid-Coated Particles]

The water-soluble polymer-coated particles (355 μm-125 μm) (500.0 g) were placed and fluidized in a fine particle coater granulator/Wurster, and the organic acid coating liquid (1665.5 g) was sprayed at spray air pressure 0.3 MPa, spray air flow rate 65 NL/min, inlet air temperature 76° C., inlet air flow rate 0.7 m³/min, spray liquid feed rate 6 g/min and the particles were dried to give particles after drying (675.8 g). The total amount of the particles after drying was sieved to give organic acid-coated particles (355 μm-125 μm) (674.9 g).

[Preparation of Dissolution Controlling Substance Coating Liquid]

To purified water (1200.0 g) were added aminoalkylmethacrylate copolymer E (5.03 g), succinic acid (76.01 g) and the mixture was stirred to give a dissolution controlling substance coating liquid.

[Preparation of Dissolution Controlling Substance-Coated Particles]

The organic acid-coated particles (355 μm-125 μm) (330.0 g) were placed and fluidized in a fine particle coater granulator/Wurster, the dissolution controlling substance coating liquid (839.0 g) was sprayed at spray air pressure 0.30 MPa, spray air flow rate 65 NL/min, inlet air temperature 70-76° C., inlet air flow rate 0.6-0.7 m³/min, spray liquid feed rate 3-5 g/min, and the particles were dried to give particles after drying (371.5 g). The total amount of the particles after drying was sieved to give dissolution controlling substance-coated particles (355 μm-125 μm) (370.5 g).

[Preparation of Water-Insoluble Polymer Coating Liquid]

In purified water (273.0 g) were suspended and dissolved triacetin (4.53 g) and talc (22.51 g), and the mixture was added to stirring aminoalkylmethacrylate copolymer RS (Eudragit RS30D, manufactured by Evonik) (150.04 g) to give a water-insoluble polymer coating liquid.

[Preparation of Water-Insoluble Polymer-Coated Particles]

The dissolution controlling substance-coated particles (355 μm-125 μm) (365.0 g) were placed and fluidized in a fine particle coater granulator/Wurster, and sampling was performed at a time point when the water-insoluble polymer coating liquid (200.0 g) was sprayed at spray air pressure 0.2 MPa, spray air flow rate 65 NL/min, inlet air temperature 35° C., inlet air flow rate 0.7 m³/min, spray liquid feed rate 1-2 g/min to give particles after spraying (7.23 g). Successively, the particles after spraying were dried and cured in Forced Convection Constant Temperature Oven at 60° C. for 14 hr. The particles after drying and curing were screened with an aperture 355 μm sieve to give sieved particles, water-insoluble polymer-coated particles.

[Preparation of Orally Disintegrating Tablet Containing Water-Insoluble Polymer-Coated Particles]

The water-insoluble polymer-coated particles (1924.8 mg), the outer layer granules (3377.7 mg) obtained in Example 12, aspartame (63.0 mg), sodium stearyl fumarate (94.5 mg), and crystalline cellulose (CEOLUS KG-802, manufactured by Asahi Kasei Corporation) (525.0 mg) were blended by shaking 100 times in a glass bottle to give a blended product containing the water-insoluble polymer-coated particles. The blended product containing the water-insoluble polymer-coated particles (570.0 mg) was weighed, and tableted using a ϕ11.5 mm flat punch and a single punch tableting machine at 7 kN to give an orally disintegrating tablet containing the water-insoluble polymer-coated particles (corresponding to 20 mg of compound A as a free base per tablet).

Comparative Example 1

[Preparation of Orally Disintegrating Tablet Containing Organic Acid-Coated Particles]

The organic acid-coated particles (567.0 mg) obtained in Example 1, excipient for direct compression of ODT (SmartEX, manufactured by Freund Corporation) (500.0 mg), aspartame (11.0 mg), l-menthol (2.8 mg), acesulfame potassium (2.8 mg), sodium stearyl fumarate (16.5 mg), and crystalline cellulose (CEOLUS KG-802, manufactured by Asahi Kasei Corporation) (275.0 mg) were blended by shaking 100 times in a glass bottle to give a blended product containing organic acid-coated particles. The blended product containing the organic acid-coated particles (250 mg) was weighed, and tableted using a ϕ8.5 mm flat punch and a single punch tableting machine at 3 kN to give an orally disintegrating tablet containing the organic acid-coated particles (corresponding to 20 mg of compound A as a free base per tablet).

Reference Example 1

[Preparation of Compound a Coating Liquid]
In purified water (417.9 g) was dissolved hydroxypropylmethylcellulose 2910 (15.62 g) to give a hydroxypropylmethylcellulose solution. Successively, compound A (117.0 g) was uniformly dispersed in the hydroxypropylmethylcellulose solution to give a compound A coating liquid.
[Preparation of Compound A-Coated Particles]
Lactose/crystalline cellulose spherical granules (299.8 g) were placed and fluidized in a fine particle coater granulator/Wurster, the compound A coating liquid (490.0 g) was sprayed at spray air pressure 0.4 MPa, spray air flow rate 60 NL/min, inlet air temperature 75° C., inlet air flow rate 0.7 m$^3$/min, spray liquid feed rate 6 g/min and the particles were dried to give particles after drying (360.4 g). The total amount of the particles after drying was sieved to give compound A-coated particles (355 μm-125 μm) (358.3 g).
[Preparation of Water-Insoluble Polymer Coating Liquid]
In purified water (363.4 g) were suspended and dissolved triacetin (5.96 g), talc (30.01 g), and red ferric oxide (0.6010 g), and the mixture was added to stirring aminoalkylmethacrylate copolymer RS (Eudragit RS30D, manufactured by Evonik) (200.0 g) to give a water-insoluble polymer coating liquid.
[Preparation of Water-Insoluble Polymer-Coated Particles]
The compound A-coated particles (355 μm-125 μm) (330.0 g) were placed and fluidized in a fine particle coater granulator/Wurster, and the water-insoluble polymer coating liquid (461.0 g) was sprayed at spray air pressure 0.4 MPa, spray air flow rate 60 NL/min, inlet air temperature 38° C., inlet air flow rate 0.7 m$^3$/min, spray liquid feed rate 3 g/min to give particles after spraying (347.3 g). Successively, the particles after spraying were dried and cured in Forced Convection Constant Temperature Oven at 60° C. for 14 hr. The particles after drying and curing were screened with an aperture 355 μm sieve to give sieved particles, water-insoluble polymer-coated particles.

Reference Example 2

[Preparation of Compound a Coating Liquid]
In purified water (320.1 g) was dissolved hydroxypropylmethylcellulose 2910 (12.01 g) to give a hydroxypropylmethylcellulose solution. Successively, compound A (90.15 g) was uniformly dispersed in the hydroxypropylmethylcellulose solution to give a compound A coating liquid.
[Preparation of Compound A-Coated Particles]
Crystalline cellulose (particle) (CELPHERE CP203, manufactured by Asahi Kasei Corporation) (450.4 g) were placed and fluidized in a fine particle coater granulator/Wurster, the compound A coating liquid (380.0 g) was sprayed at spray air pressure 0.3 MPa, spray air flow rate 60-70 NL/min, inlet air temperature 74-78° C., inlet air flow rate 0.6 m$^3$/min, spray liquid feed rate 4-5 g/min and the particles were dried to give particles after drying (500.1 g). The total amount of the particles after drying was sieved to give compound A-coated particles (355 μm-125 μm) (493.1 g).

[Preparation of Water-Soluble Polymer Coating Liquid (1)]
In purified water (4000.0 g) was dissolved HPMC (120.1 g) and talc (60.05 g) was suspended to give a water-soluble polymer coating liquid (1).
[Preparation of Water-Soluble Polymer-Coated Particles (1)]
The compound A-coated particles (355 μm-125 μm) (480.1 g) were placed and fluidized in a fine particle coater granulator/Wurster, the water-soluble polymer coating liquid (1) (4020.0 g) was sprayed at spray air pressure 0.3 MPa, spray air flow rate 70 NL/min, inlet air temperature 84° C., inlet air flow rate 0.7 m$^3$/min, spray liquid feed rate 4-8 g/min and the particles were dried to give particles after drying (611.5 g). The total amount of the particles after drying was sieved to give water-soluble polymer-coated particles (1) (425 μm-125 μm) (566.6 g).
[Preparation of Water-Soluble Polymer Coating Liquid (2)]
In purified water (4000.0 g) was dissolved HPMC (120.3 g) and talc (60.13 g) was suspended to give water-soluble polymer coating liquid (2).
[Preparation of Water-Soluble Polymer-Coated Particles (2)]
The water-soluble polymer-coated particles (1) (425 μm-125 μm) (566.6 g) were placed and fluidized in a fine particle coater granulator/Wurster, the water-soluble polymer coating liquid (2) (4000.0 g) was sprayed at spray air pressure 0.3 MPa, spray air flow rate 60-75 NL/min, inlet air temperature 81° C., inlet air flow rate 0.7 m$^3$/min, spray liquid feed rate 4-7 g/min and the particles were dried to give particles after drying (722.8 g). The total amount of the particles after drying was sieved to give water-soluble polymer-coated particles (2) (500 μm-150 μm) (714.2 g).
[Preparation of Water-Soluble Polymer Coating Liquid (3)]
In purified water (4000.0 g) was dissolved HPMC (120.3 g) and talc (60.06 g) was suspended to give water-soluble polymer coating liquid (3).
[Preparation of Water-Soluble Polymer-Coated Particles (3)]
The water-soluble polymer-coated particles (2) (500 μm-150 μm) (680.0 g) were placed and fluidized in a fine particle coater granulator/Wurster, the water-soluble polymer coating liquid (3) (4000.0 g) was sprayed at spray air pressure 0.3 MPa, spray air flow rate 70-80 NL/min, inlet air temperature 81-84° C., inlet air flow rate 0.7 m$^3$/min, spray liquid feed rate 5-7 g/min and the particles were dried to give particles after drying (821.0 g). The total amount of the particles after drying was sieved to give water-soluble polymer-coated particles (3) (500 μm-150 μm) (757.6 g).

Reference Example 3

[Preparation of Compound a Coating Liquid]
In purified water (399.92 g) was dissolved hydroxypropylmethylcellulose 2910 (24.01 g) to give a hydroxypropylmethylcellulose solution. Successively, compound A (180.3 g) was uniformly dispersed in the hydroxypropylmethylcellulose solution to give a compound A coating liquid.
[Preparation of Water-Soluble Polymer Coating Liquid]
In purified water (400.30 g) was dissolved hydroxypropylmethylcellulose 2910 (21.88 g) to give a hydroxypropylmethylcellulose solution. Talc (11.21 g) was added and uniformly dispersed to give a water-soluble polymer coating liquid.
[Preparation of Water-Soluble Polymer-Coated Particles]
Lactose/crystalline cellulose spherical granules (300.0 g) were placed and fluidized in a fine particle coater granulator/Wurster, and the compound A coating liquid (600.0 g) was sprayed at spray air pressure 0.5 MPa, spray air flow rate 60 NL/min, inlet air temperature 70° C., inlet air flow rate 0.5-0.6 m$^3$/min, spray liquid feed rate 5-7 g/min. Successively, an HPMC coating liquid (400.0 g) was sprayed at spray air pressure 0.5 MPa, spray air flow rate 60 NL/min, inlet air temperature 85° C., inlet air flow rate 0.5-0.6 m³/min, spray liquid feed rate 3-4 g/min and the particles were dried to give particles after drying (465.3 g). The total amount of the particles after drying was sieved to give water-soluble polymer-coated particles (250 μm-105 μm) (409.3 g).

[Preparation of Dissolution Controlling Substance Coating Liquid]

In purified water (1750.4 g) were dissolved hydroxypropylmethylcellulose 2910 (30.3 g), and polysorbate 80 (manufactured by NOF CORPORATION) (0.1498 g), succinic acid (Wako special grade, manufactured by Wako Pure Chemical Industries, Ltd., hereinafter the same) (119.58 g) to give a dissolution controlling substance coating liquid.

[Preparation of Dissolution Controlling Substance-Coated Particles]

The water-soluble polymer-coated particles (250 μm-105 μm) (399.8 g) were placed and fluidized in a fine particle coater granulator/Wurster, the dissolution controlling substance coating liquid (1870.0 g) was sprayed at spray air pressure 0.5 MPa, spray air flow rate 60 NL/min, inlet air temperature 85° C., inlet air flow rate 0.5 m³/min, spray liquid feed rate 4-5 g/min and the particles were dried to give particles after drying (505.0 g). The total amount of the particles after drying was sieved to give dissolution controlling substance-coated particles (250 μm-105 μm) (497.5 g).

[Preparation of Water-Insoluble Polymer Coating Liquid]

In purified water (546.0 g) were suspended and dissolved triacetin (9.01 g), talc (45.3 g), and red ferric oxide (0.2935 g), and the mixture was added to stirring aminoalkylmethacrylate copolymer RS (Eudragit RS30D, manufactured by Evonik) (300.3 g) to give a water-insoluble polymer coating liquid.

[Preparation of Water-Insoluble Polymer-Coated Particles]

The dissolution controlling substance-coated particles (250 μm-105 μm) (440.3 g) were placed and fluidized in a fine particle coater granulator/Wurster, and the water-insoluble polymer coating liquid (550.0 g) was sprayed at spray air pressure 0.5 MPa, spray air flow rate 60 NL/min, inlet air temperature 44° C., inlet air flow rate 0.4-0.5 m³/min, spray liquid feed rate 3 g/min to give particles after spraying (492.9 g). The total amount of the particles after spraying were screened to give particles after spraying (355 μm-105 μm). Successively, the particles after spraying (355 μm-105 μm) were dried and cured in Forced Convection Constant Temperature Oven at 60° C. for 14 hr. The particles after drying and curing were screened with an aperture 300 μm sieve to give sieved particles, water-insoluble polymer-coated particles.

[Preparation of Outer Layer Granules]

In purified water (316.9 g) were dissolved D-mannitol (PEARLITOL 50C, manufactured by ROQUETTE Japan) (31.56 g), citric anhydride (manufactured by ADM Far East) (41.97 g) to give a binder. D-mannitol (PEARLITOL 50C, manufactured by ROQUETTE Japan) (371.4 g), crystalline cellulose (CEOLUS KG-802, manufactured by Asahi Kasei Corporation) (59.83 g), low-substituted hydroxypropylcellulose (59.94 g), and crospovidone (Polyplasdone XL-10, manufactured by ISP) (29.66 g) were fed and fluidized in a fluid bed dryer granulator (LAB-1, manufactured by POWREX, hereinafter the same), and the binder (210.0 g) was sprayed at spray air pressure 0.1 MPa, spray air flow rate 60 NL/min, inlet air temperature 85° C., inlet air flow rate 0.3 m³/min, spray liquid feed rate 10 g/min, and the granules were dried. The dried granules were screened with an aperture 850 μm sieve to give sieved granules, outer layer granules (533.0 g).

[Preparation of Coagulation Inhibiting Substance Coating Liquid]

In purified water (262.6 g) was dissolved D-mannitol (PEARLITOL 50C, manufactured by ROQUETTE Japan) (37.50 g) to give a coagulation inhibiting substance coating liquid.

[Preparation of Coagulation Inhibiting Substance-Coated Particles]

The water-insoluble polymer-coated particles (250.0 g) were placed and fluidized in a fine particle coater granulator/Wurster, and the coagulation inhibiting substance coating liquid (200.0 g) was sprayed at spray air pressure 0.5 MPa, spray air flow rate 60 NL/min, inlet air temperature 53-60° C., inlet air flow rate 0.5 m³/min, spray liquid feed rate 2-4 g/min and the particles were dried to give particles after drying (263.9 g). The total amount of the particles after spraying was screened to give coagulation inhibiting substance-coated particles within the range of 355 μm-105 μm.

[Preparation of Orally Disintegrating Tablet Containing Coagulation Inhibiting Substance-Coated Particles]

The coagulation inhibiting substance-coated particles (21543.6 mg), the outer layer granules (33483.8 mg), aspartame (321 mg), l-menthol (200.6 mg), acesulfame potassium (80.3 mg), sodium stearyl fumarate (481.5 mg), strawberry flavor (STRAWBERRY DURAROME, manufactured by Nihon Firmenich K. K., hereinafter the same) (64.2 mg), and crystalline cellulose (CEOLUS KG-802, manufactured by Asahi Kasei Corporation) (8025.0 mg) were blended by shaking 100 times in a glass bottle to give a blended product containing the coagulation inhibiting substance-coated particles. The blended product containing the coagulation inhibiting substance-coated particles (400 mg) was weighed, and tableted using a φ10.0 mm flat punch and a single punch tableting machine at 6 kN to give an orally disintegrating tablet containing the coagulation inhibiting substance-coated particles (corresponding to 20 mg of compound A as a free base per tablet).

The formulation (Calculated) of the preparations of Examples 1-14, Comparative Example 1, and Reference Examples 1-3 are shown in Tables 1-1 to 1-4.

Eudragit RS30D (trade name) is sold in the form of a 30% water dispersion. In the Tables, Eudragit RS30D shows a solid content.

TABLE 1-1

|  |  | Example 1 | Example 2 | Example 3 | Example 4 | Example 5 |
| --- | --- | --- | --- | --- | --- | --- |
| compound A- | NONPAREIL 105T | 47.2 | 48.9 | 48.9 | 48.9 | 48.9 |
| containing | compound A | 26.7 | 26.7 | 26.7 | 26.7 | 26.7 |
| particles | HPMC TC-5E | 3.56 | 3.56 | 3.56 | 3.56 | 3.56 |
| organic acid | fumaric acid | 20.9 | 12.6 | 12.6 | 12.6 | 12.6 |
| coating layer | HPMC TC-5E | 4.18 | 4.21 | 4.21 | 4.21 | 4.21 |
| water-insoluble | Eudragit RS30D | 11.5 | 12 | 7.2 | 9.6 | 10.6 |
| polymer coating | triacetin | 1.15 | 1.2 | 0.72 | 0.96 | 1.06 |

TABLE 1-1-continued

|  |  | Example 1 | Example 2 | Example 3 | Example 4 | Example 5 |
|---|---|---|---|---|---|---|
| layer | talc | 5.77 | 6 | 3.6 | 4.8 | 5.28 |
|  | red ferric oxide | 0.0192 | 0.04 | 0.024 | 0.032 | 0.0352 |
| outer layer | D-mannitol | — | 167 | 173 | 170 | 169 |
| granule component | L-HPC LH-33 | — | 24.3 | 25.1 | 24.7 | 24.5 |
|  | crospovidone XL-10 | — | 12.1 | 12.5 | 12.3 | 12.3 |
|  | crystalline cellulose KG-802 | — | 24.3 | 25.1 | 24.7 | 24.5 |
|  | Smart EX QD-100 | 73 | — | — | — | — |
| blended product component | aspartame | 2 | 2 | 2 | 2 | 2 |
|  | l-menthol | 0.5 | 1.25 | 1.25 | 1.25 | 1.25 |
|  | acesulfame potassium | 0.5 | 0.5 | 0.5 | 0.5 | 0.5 |
|  | sodium stearyl fumarate | 3 | 3 | 3 | 3 | 3 |
|  | crystalline cellulose KG-802 | 50 | 50 | 50 | 50 | 50 |
|  | strawberry D | — | 0.4 | 0.4 | 0.4 | 0.4 |
| total (mg/tablet) |  | 250 | 400 | 400 | 400 | 400 |

TABLE 1-2

|  |  | Example 6 | Example 7 | Example 8 | Example 9 |
|---|---|---|---|---|---|
| compound A-containing particles | NONPAREIL 105T | 48.9 | 48.9 | 77.6 | — |
|  | partly pregelatinized starch | — | — | — | 49.8 |
|  | compound A | 26.7 | 26.7 | 26.7 | 26.7 |
|  | HPMC TC-5E | 3.56 | 3.56 | 3.56 | 2.67 |
| organic acid coating layer (1) | fumaric acid | 24.8 | 24.8 | 4.9 | 5.0 |
|  | HPMC TC-5E | 4.97 | 4.97 | 1.22 | 1.26 |
| dissolution controlling substance coating layer | succinic acid | 24.9 | 24.9 | 24.8 | 23.4 |
|  | HPMC TC-5E | 6.23 | 6.23 | 9.83 | 9.26 |
| organic acid coating layer (2) | fumaric acid | — | — | 19.3 | 19.8 |
|  | HPMC TC-5E | — | — | 4.83 | 4.22 |
| water insoluble polymer coating layer | Eudragit RS30D | 8.75 | 10.7 | 13.5 | 18 |
|  | triacetin | 0.88 | — | 1.35 | 1.8 |
|  | talc | 4.38 | 6.30 | 6.75 | 9 |
|  | red ferric oxide | 0.0292 | 0.0504 | 0.135 | 0.18 |
|  | Eudragit NE30D | — | 1.89 | — | — |
|  | polysorbate 80 | — | 0.101 | — | — |
|  | citric anhydride | — | 0.0189 | — | — |
| outer layer granule component | D-mannitol | 138 | 136 | 182 | 118 |
|  | L-HPC LH-33 | 20.1 | 19.7 | 26.4 | 17.1 |
|  | crospovidone XL-10 | 10.1 | 9.9 | 13.2 | 8.57 |
|  | crystalline cellulose KG-802 | 20.1 | 19.7 | 26.4 | 17.1 |
| blended product component | aspartame | 2 | 2 | 4 | 4 |
|  | l-menthol | 1.25 | 0.5 | 0.5 | — |
|  | acesulfame potassium | 0.5 | 0.5 | 0.5 | — |
|  | sodium stearyl fumarate | 3 | 3 | 3 | 4 |
|  | crystalline cellulose KG-802 | 50 | 50 | 50 | — |
|  | partly pregelatinized starch | — | — | — | 50 |
|  | monosodium fumarate | — | — | — | 10 |
|  | strawberry D | 0.400 | — | — | — |
| total (mg/tablet) |  | 400 | 400 | 500 | 400 |

TABLE 1-3

|  |  | Example 10 | Example 11 | Example 12 | Example 13 | Example 14 |
|---|---|---|---|---|---|---|
| compound A-containing particles | NONPAREIL 105T | 77 | 77 | 77 | 77 | 77 |
|  | compound A | 26.7 | 26.7 | 26.7 | 26.7 | 26.7 |
|  | HPMC TC-5E | 3.56 | 3.56 | 3.56 | 3.56 | 3.56 |
| intermediate layer | HPMC | — | — | 2.31 | 2.31 | 3 |
|  | talc | — | — | 1.16 | 1.16 | 1.5 |
| organic acid | fumaric acid | 74 | 99.5 | 25 | 50 | 50 |

TABLE 1-3-continued

|  |  | Example 10 | Example 11 | Example 12 | Example 13 | Example 14 |
|---|---|---|---|---|---|---|
| coating layer | HPMC TC-5E | 14.8 | 19.91 | 4.63 | 9.26 | — |
|  | Eudragit EPO | — | — | — | — | 3.96 |
| dissolution controlling substance coating layer | succinic acid | 46.3 | 25 | 25 | 25 | 25 |
|  | HPMC TC-5E | — | — | 8.33 | 8.33 | — |
|  | methylcellulose SM-4 | 15.4 | 8.33 | — | — | — |
|  | Eudragit EPO | — | — | — | — | 1.64 |
| water-insoluble polymer coating layer | Eudragit RS30D | 14.7 | 14.7 | 13 | 13 | 13 |
|  | triacetin | 1.47 | 1.47 | 1.3 | 1.3 | 1.3 |
|  | talc | 7.36 | 7.37 | 6.5 | 6.5 | 6.5 |
|  | yellow ferric oxide | 0.147 | 0.147 | — | — | — |
| coagulation inhibiting substance coating layer | D-mannitol | — | — | — | 12 | — |
| outer layer granule component | D-mannitol | 148 | 156 | 171 | 158 | 158 |
|  | citric anhydride | 4.44 | 4.66 | 4.94 | 4.56 | 4.55 |
|  | L-HPC LH-33 | 22.2 | 23.3 | 25.6 | 23.6 | 23.6 |
|  | crospovidone XL-10 | 11.1 | 11.6 | 12.8 | 11.8 | 11.8 |
|  | crystalline cellulose KG-802 | 22.2 | 23.3 | 25.9 | 23.9 | 23.8 |
|  | β-cyclodextrin | — | — | 50 | 46.2 | 46.1 |
| blended product component | aspartame | 6 | 6 | 6 | 6 | 6 |
|  | l-menthol flavor | — | — | — | 0.5 | — |
|  | sodium stearyl fumarate | 4 | 4 | 9 | 9 | 9 |
|  | crystalline cellulose KG-802 | 50 | — | 50 | 50 | 50 |
|  | crystalline cellulose KG-1000 | — | 50 | — | — | — |
|  | orange flavor | 0.5 | 0.5 | — | — | — |
| total (mg/unit) |  | 550 | 570 | 550 | 570 | 570 |

TABLE 1-4

|  |  | Comparative Example 1 | Reference Example 1 | Reference Example 2 | Reference Example 3 |
|---|---|---|---|---|---|
| compound A-containing particles | NONPAREIL 105T | 47.2 | 77.0 | — | 44.8 |
|  | CELPHERE CP203 | — | — | 148 | — |
|  | compound A | 26.7 | 26.7 | 26.7 | 26.7 |
|  | HPMC TC-5E | 3.56 | 3.56 | 3.56 | 3.56 |
| water-soluble polymer coating layer | HPMC | — | — | 146 | 3 |
|  | talc | — | — | 72.9 | 1.5 |
| organic acid coating layer | fumaric acid | 20.9 | — | — | — |
|  | HPMC TC-5E | 4.18 | — | — | — |
| dissolution controlling substance coating layer | succinic acid | — | — | — | 23.5 |
|  | HPMC TC-5E | — | — | — | 5.88 |
|  | polysorbate 80 | — | — | — | 0.0294 |
| water-insoluble polymer coating layer | Eudragit RS30D | — | 15.0 | — | 13.6 |
|  | triacetin | — | 1.50 | — | 1.36 |
|  | talc | — | 7.49 | — | 6.82 |
|  | red ferric oxide | — | 0.150 | — | 0.0454 |
| coagulation inhibiting substance coating layer | D-mannitol | — | — | — | 13.1 |
| outer layer granule component | D-mannitol | — | — | — | 137 |
|  | citric anhydride | — | — | — | 8.48 |
|  | L-HPC LH-33 | — | — | — | 21.2 |
|  | crospovidone XL-10 | — | — | — | 10.6 |
|  | crystalline cellulose KG-802 | — | — | — | 21.2 |
|  | SmartEX | 91.5 | — | — | — |
| blended product component | aspartame | 2.00 | — | — | 2 |
|  | l-menthol | 0.500 | — | — | 1.25 |
|  | acesulfame potassium | 0.500 | — | — | 0.5 |
|  | sodium stearyl fumarate | 3.00 | — | — | 3 |
|  | crystalline cellulose KG-802 | 50.0 | — | — | 50 |
|  | strawberry D | — | — | — | 0.4 |
| total (mg/unit) |  | 250 | 131.4 | 397.3 | 400 |

Example 15

[Preparation of Compound a Coating Liquid]

In purified water (1763.0 g) was dissolved hydroxypropylmethylcellulose 2910 (77.08 g) to give a hydroxypropylmethylcellulose 2910 solution. Successively, compound A (627.9 g) was uniformly dispersed in the hydroxypropylmethylcellulose 2910 solution to give a compound A coating liquid.

[Preparation of Compound A-Coated Particles]

Lactose/crystalline cellulose spherical granules (1463.0 g) were placed and fluidized in fine particle coater granulator/Wurster (FD-MP-10, manufactured by POWREX, hereinafter the same), the compound A coating liquid (2294.0 g) was sprayed at spray air pressure 0.21 MPa, spray air flow rate 70 NL/min, inlet air temperature 67-70° C., inlet air flow rate 1.3 m³/min, spray liquid feed rate 15 g/min and the particles were dried to give particles after drying (1939.6 g). The total amount of the particles after drying was sieved to give compound A-coated particles (355 μm-105 μm) (1936.0 g).

[Preparation of Organic Acid Coating Liquid]

In purified water (3675.0 g) and anhydrous ethanol (1575.0 g) were dissolved ammonioalkylmethacrylate copolymer (Eudragit RLPO, manufactured by Evonik) (21.00 g) and succinic acid (350.0 g). Successively, monosodium fumarate (MONOFUMAR, manufactured by NIPPON SHOKUBAI CO., LTD.) (700.0 g) jet milled in advance was uniformly dispersed to give an organic acid coating liquid.

[Preparation of Organic Acid-Coated Particles]

compound A-coated particles (355 μm-105 μm) (1391.0 g) were placed and fluidized in a fine particle coater granulator/Wurster, the organic acid coating liquid (6104.0 g) was sprayed at spray air pressure 0.21 MPa, spray air flow rate 70 NL/min, inlet air temperature 68-73° C., inlet air flow rate 1.3-1.4 m³/min, spray liquid feed rate 18-19 g/min and the particles were dried to give particles after drying (2035.0 g). The total amount of the particles after drying was sieved to give organic acid-coated particles (355 μm-105 μm).

[Preparation of Water-Insoluble Polymer Coating Liquid]

In purified water (99.0 g) and anhydrous ethanol (891.0 g) were suspended triacetin (6.6 g), titanium oxide (6.6 g) and talc (33.0 g), further, ammonioalkylmethacrylate copolymer (Eudragit RSPO, manufactured by Evonik) (52.8 g) and ammonioalkylmethacrylate copolymer (Eudragit RLPO, manufactured by Evonik) (13.20 g) were dissolved to give a water-insoluble polymer coating liquid.

[Preparation of Coagulation Inhibiting Substance Coating Liquid]

In purified water (171.0 g) was dispersed light anhydrous silicic acid (Sylysia 320, manufactured by FUJI SILYSIA CHEMICAL LTD.) (9.0 g) to give a coagulation inhibiting substance coating liquid.

[Preparation of Coagulation Inhibiting Substance-Coated Particles]

The organic acid-coated particles (355 μm-105 μm) (1110.0 g) were placed and fluidized in a fine particle coater granulator/Wurster, the water-insoluble polymer coating liquid (661.3 g) was sprayed at spray air pressure 0.21 MPa, spray air flow rate 70 NL/min, inlet air temperature 27-28° C., inlet air flow rate 1.2-1.3 m³/min, spray liquid feed rate 4 g/min to give water-insoluble polymer-coated particles. Successively, the coagulation inhibiting substance coating liquid (79.2 g) was sprayed at spray air pressure 0.21 MPa, spray air flow rate 70 NL/min, inlet air temperature 28-73° C., inlet air flow rate 1.3 m³/min, spray liquid feed rate 5 g/min and the particles were dried to give particles after drying (1131.0 g). The total amount of the particles after drying was sieved to give coagulation inhibiting substance-coated particles (355 μm-105 μm) (1130.0 g).

[Preparation of Outer Layer Granules]

In purified water (600.0 g) were dissolved and suspended D-mannitol (PEARLITOL 50C, manufactured by ROQUETTE Japan) (30.0 g), citric anhydride (30.0 g) and crospovidone (Kollidon CL-SF, manufactured by BASF) (30.0 g) to give a spray liquid. D-mannitol (PEARLITOL 50C, manufactured by ROQUETTE Japan) (84.0 g), D-mannitol (PEARLITOL 100SD, manufactured by ROQUETTE Japan) (240.0 g), crystalline cellulose (CEOLUS KG-802, manufactured by Asahi Kasei Corporation) (48.0 g), low-substituted hydroxypropylcellulose (48.0 g) and crospovidone (Kollidon CL-F, manufactured by BASF) (24.0 g) were placed and fluidized in a fluid bed dryer granulator (LAB-1, manufactured by POWREX), the spray liquid (230.0 g) was sprayed at spray air pressure 0.14 MPa, spray air flow rate 60 NL/min, inlet air temperature 82-83° C., inlet air flow rate 0.2 m³/min, spray liquid feed rate 6 g/min and the granules were dried to give outer layer granules (443.4 g).

[Preparation of Orally Disintegrating Tablet Containing Coagulation Inhibiting Substance-Coated Particles]

The coagulation inhibiting substance-coated particles (107.4 g), the outer layer granules (142.2 g), crystalline cellulose (CEOLUS KG-802, manufactured by Asahi Kasei Corporation) (14.4 g), crospovidone (Kollidon CL-F, manufactured by BASF) (14.4 g), magnesium alumino metasilicate (Neusilin FL2, manufactured by Fuji Chemical Industries Co., Ltd., hereinafter the same) (0.78 g), acesulfame potassium (2.4 g), aspartame (2.4 g), peppermint cortone (0.48 g) and sodium stearyl fumarate (2.88 g) were mixed in a 10 L plastic bag by hand mixing to give a blended product. The blended product was tableted using a rotary type tableting machine at average 7.5 kN to give an orally disintegrating tablet (weight 478.9 mg and diameter 10.5 mm) containing 20 mg of a free form of compound A.

Example 16

[Preparation of Compound a Coating Liquid]

In purified water (1800.0 g) was dissolved hydroxypropylmethylcellulose 2910 (78.72 g) to give a hydroxypropylmethylcellulose 2910 solution. Successively, compound A (641.3 g) was uniformly dispersed in the hydroxypropylmethylcellulose 2910 solution to give a compound A coating liquid.

[Preparation of Compound A-Coated Particles]

Lactose/crystalline cellulose spherical granules (1463.0 g) were placed and fluidized in a fine particle coater granulator/Wurster (FD-MP-10, manufactured by POWREX, hereinafter the same), the compound A coating liquid (2394.0 g) was sprayed at spray air pressure 0.21 MPa, spray air flow rate 70 NL/min, inlet air temperature 66-68° C., inlet air flow rate 1.3 m³/min, spray liquid feed rate 15 g/min and the particles were dried to give particles after drying (1986.5 g). The total amount of the particles after drying was sieved to give compound A-coated particles (355 μm-105 μm) (1985.5 g).

[Preparation of Organic Acid Coating Liquid]

In purified water (4305.0 g and anhydrous ethanol (1845.0 g) were dissolved ammonioalkylmethacrylate copolymer (Eudragit RLPO, manufactured by Evonik) (24.60 g) and succinic acid (410.0 g). Successively, monosodium fumarate (MONOFUMAR, manufactured by NIPPON SHOKUBAI CO., LTD.) (820.0 g) jet milled in advance was uniformly dispersed to give an organic acid coating liquid.

[Preparation of Organic Acid-Coated Particles]

The compound A-coated particles (355 μm-105 μm) (1605.0 g) were placed and fluidized in a fine particle coater granulator/Wurster, the organic acid coating liquid (7043.0 g) was sprayed at spray air pressure 0.21 MPa, spray air flow rate 70 NL/min, inlet air temperature 66-69° C., inlet air flow rate 1.3-1.4 m$^3$/min, spray liquid feed rate 16-18 g/min and the particles were dried to give particles after drying (2309.6 g). The total amount of the particles after drying was sieved to give organic acid-coated particles (355 μm-105 μm) (2803.6 g).

[Preparation of Water-Insoluble Polymer Coating Liquid]

In purified water (129.6 g) and anhydrous ethanol (1166 g) were suspended triacetin (8.64 g), titanium oxide (8.96 g) and talc (43.2 g), further, ammonioalkylmethacrylate copolymer (Eudragit RSPO, manufactured by Evonik) (60.48 g) and ammonioalkylmethacrylate copolymer (Eudragit RLPO, manufactured by Evonik) (25.92 g) were dissolved to give a water-insoluble polymer coating liquid.

[Preparation of Coagulation Inhibiting Substance Coating Liquid]

In purified water (114.0 g) was dispersed light anhydrous silicic acid (Sylysia 320, manufactured by FUJI SILYSIA CHEMICAL LTD.) (6.0 g) to give a coagulation inhibiting substance coating liquid.

[Preparation of Coagulation Inhibiting Substance-Coated particles]

The organic acid-coated particles (355 μm-105 μm) (1682.0 g) were placed and fluidized in a fine particle coater granulator/Wurster, the water-insoluble polymer coating liquid (902.0 g) was sprayed at spray air pressure 0.21 MPa, spray air flow rate 70 NL/min, inlet air temperature 28-29° C., inlet air flow rate 1.3 m$^3$/min, spray liquid feed rate 4 g/min to give water-insoluble polymer-coated particles. Successively, the coagulation inhibiting substance coating liquid (120.0 g) was sprayed at spray air pressure 0.21 MPa, spray air flow rate 70 NL/min, inlet air temperature 28-73° C., inlet air flow rate 1.3 m$^3$/min, spray liquid feed rate 5 g/min and the particles were dried to give particles after drying (1745.0 g). The total amount of the particles after drying was sieved to give coagulation inhibiting substance-coated particles (355 μm-105 μm) (1743.0 g).

[Preparation of Outer Layer Sieved Granules]

In purified water (4000.0 g) were dissolved and suspended D-mannitol (PEARLITOL 50C, manufactured by ROQUETTE Japan) (200.0 g), citric anhydride (200.0 g) and crospovidone (Kollidon CL-SF, manufactured by BASF) (200.0 g) to give a spray liquid. D-mannitol (PEARLITOL 50C, manufactured by ROQUETTE Japan) (529.1 g), D-mannitol (PEARLITOL 100SD, manufactured by ROQUETTE Japan) (2035.0 g), crystalline cellulose (CEOLUS KG-802, manufactured by Asahi Kasei Corporation) (370.0 g), low-substituted hydroxypropylcellulose (370.0 g) and crospovidone (Kollidon CL-F, manufactured by BASF) (185.0 g) were placed and fluidized in a fluid bed dryer granulator (FD-5S, manufactured by POWREX), the spray liquid (2128.0 g) was sprayed at spray air pressure 0.24 MPa, spray air flow rate 2600 NL/hr, inlet air temperature 70-72° C., inlet air flow rate 1.3 m$^3$/min, spray liquid feed rate 45 g/min and the granules were dried to give outer layer granules (3741.3 g). The outer layer granules (3665.0 g) were placed in a power mill and sieved with a screen with size 1.5 mm to give outer layer sieved granules (3644.6 g).

[Preparation of Orally Disintegrating Tablet Containing Coagulation Inhibiting Substance-Coated Particles]

The coagulation inhibiting substance-coated particles (1629.0 g, the outer layer sieved granules (1424.0 g), crystalline cellulose (CEOLUS KG-802, manufactured by Asahi Kasei Corporation) (176.0 g), crospovidone (Kollidon CL-F, manufactured by BASF) (176.0 g), magnesium alumino metasilicate (Neusilin FL2, manufactured by Fuji Chemical Industries Co., Ltd.) (9.6 g), acesulfame potassium (32.0 g), aspartame (32.0 g), peppermint cortone (6.4 g) and sodium stearyl fumarate (35.2 g) were placed in a tumbler type blending machine, mixed at 30 rpm for 5 min to give a blended product (3509.5 g). The blended product was tableted using a rotary type tableting machine at average 7.8 kN to give an orally disintegrating tablet (weight 440 mg and diameter 10 mm) containing 20 mg of a free form of compound A.

Example 17

[Preparation of Compound a Coating Liquid]

In purified water (2400.0 g) was dissolved hydroxypropylmethylcellulose 2910 (105.0 g) to give a hydroxypropylmethylcellulose 2910 solution. Successively, compound A (855.0 g) was uniformly dispersed in the hydroxypropylmethylcellulose 2910 solution to give a compound A coating liquid.

[Preparation of Compound A-Coated Particles]

Lactose/crystalline cellulose spherical granules (1848.0 g) was placed and fluidized in a fine particle coater granulator/Wurster (FD-MP-10, manufactured by POWREX, hereinafter the same), the compound A coating liquid (3024.0 g) was sprayed at spray air pressure 0.21 MPa, spray air flow rate 70 NL/min, inlet air temperature 65-67° C., inlet air flow rate 1.3 m$^3$/min, spray liquid feed rate 11-14 g/min and the particles were dried to give particles after drying (2539.8 g). The total amount of the particles after drying was sieved to give compound A-coated particles (355 μm-105 μm) (2512.1 g).

[Preparation of Organic Acid Coating Liquid]

In purified water (2100.0 g) and anhydrous ethanol (900.0 g) were dissolved ammonioalkylmethacrylate copolymer (Eudragit RLPO, manufactured by Evonik) (18.00 g) and succinic acid (300.0 g). Successively, monosodium fumarate (MONOFUMAR, manufactured by NIPPON SHOKUBAI CO., LTD.) (300.0 g) jet milled in advance was uniformly dispersed to give an organic acid coating liquid.

[Preparation of Organic Acid-Coated Particles]

The compound A-coated particles (355 μm-105 μm) (1124.0 g) were placed and fluidized in a fine particle coater granulator/Wurster, the organic acid coating liquid (3292.0 g) was sprayed at spray air pressure 0.21 MPa, spray air flow rate 70 NL/min, inlet air temperature 66-68° C., inlet air flow rate 1.3 m$^3$/min, spray liquid feed rate 16-17 g/min and the particles were dried to give particles after drying (1591.0 g). The total amount of the particles after drying was sieved to give organic acid-coated particles (355 μm-105 μm) (1574.0 g).

[Preparation of Water-Insoluble Polymer Coating Liquid]

In purified water (86.4 g) and anhydrous ethanol (777.6 g) were suspended triacetin (5.76 g), titanium oxide (6.72 g), yellow ferric oxide (0.72 g) and talc (28.8 g), further, ammonioalkylmethacrylate copolymer (Eudragit RSPO, manufactured by Evonik) (34.56 g) and ammonioalkylmethacrylate copolymer (Eudragit RLPO, manufactured by Evonik) (23.04 g) were dissolved to give a water-insoluble polymer coating liquid.

[Preparation of Coagulation Inhibiting Substance Coating Liquid]

In purified water (85.5 g) was dispersed light anhydrous silicic acid (Sylysia 320, manufactured by FUJI SILYSIA CHEMICAL LTD.) (4.5 g) to give a coagulation inhibiting substance coating liquid.

[Preparation of Coagulation Inhibiting Substance-Coated Particles]

The organic acid-coated particles (355 μm-105 μm) (1112.0 g) were placed and fluidized in a fine particle coater granulator/Wurster, the water-insoluble polymer coating liquid (602.3 g) was sprayed at spray air pressure 0.20 MPa, spray air flow rate 70 NL/min, inlet air temperature 27-29° C., inlet air flow rate 1.3 m³/min, spray liquid feed rate 4 g/min to give water-insoluble polymer-coated particles. Successively, the coagulation inhibiting substance coating liquid (90.0 g) was sprayed at spray air pressure 0.20 MPa, spray air flow rate 70 NL/min, inlet air temperature 28-73° C., inlet air flow rate 1.3 m³/min, spray liquid feed rate 5-6 g/min and the particles were dried to give particles after drying (1149.0 g). The total amount of the particles after drying was sieved to give coagulation inhibiting substance-coated particles (355 μm-105 μm) (1143.0 g).

[Preparation of Orally Disintegrating Tablet Containing Coagulation Inhibiting Substance-Coated Particles]

The coagulation inhibiting substance-coated particles (94.8 g), the outer layer sieved granules (106.3 g) obtained in Example 16, crystalline cellulose (CEOLUS KG-802, manufactured by Asahi Kasei Corporation) (11.4 g), crospovidone (Kollidon CL-F, manufactured by BASF) (6.84 g), magnesium alumino metasilicate (Neusilin FL2, manufactured by Fuji Chemical Industries Co., Ltd.) (1.14 g), acesulfame potassium (2.4 g), aspartame (2.4 g), peppermint cortone (0.48 g) and sodium stearyl fumarate (2.28 g) were placed in a 10 L plastic bag and mixed 200 times by hand mixing to give a blended product. The blended product was tableted using a rotary type tableting machine at average 7 kN to give an orally disintegrating tablet (weight 380 mg and diameter 9.5 mm) containing 20 mg of a free form of compound A.

Example 18

[Preparation of Compound a Coating Liquid]

In purified water (467.2 g) was dissolved hydroxypropylmethylcellulose 2910 (19.07 g) to give a hydroxypropylmethylcellulose 2910 solution. Successively, compound A (171.0 g) was uniformly dispersed in the hydroxypropylmethylcellulose 2910 solution to give a compound A coating liquid.

[Preparation of Compound A-Coated Particles]

Lactose/crystalline cellulose spherical granules (385.0 g) were placed and fluidized in a fine particle coater granulator/Wurster (FD-MP-01, manufactured by POWREX, hereinafter the same), the compound A coating liquid (590.6 g) was sprayed at spray air pressure 0.3 MPa, spray air flow rate 70 NL/min, inlet air temperature 77° C., inlet air flow rate 0.5-0.6 m³/min, spray liquid feed rate 4-5 g/min and the particles were dried to give particles after drying (509.3 g). The total amount of the particles after drying was sieved to give compound A-coated particles (355 μm-105 μm) (490.7 g).

[Preparation of Organic Acid Coating Liquid]

In purified water (840.0 g) and anhydrous ethanol (1260.0 g) were dissolved ammonioalkylmethacrylate copolymer (Eudragit RLPO, manufactured by Evonik) (6.0 g) and succinic acid (100.0 g). Successively, monosodium fumarate (MONOFUMAR, manufactured by NIPPON SHOKUBAI CO., LTD.) (300.0 g) jet milled in advance was uniformly dispersed to give an organic acid coating liquid.

[Preparation of Organic Acid-Coated Particles]

The compound A-coated particles (355 μm-105 μm) (384.1 g) were placed and fluidized in a fine particle coater granulator/Wurster, the organic acid coating liquid (2165.0 g) was sprayed at spray air pressure 0.3 MPa, spray air flow rate 60 NL/min, inlet air temperature 77° C., inlet air flow rate 0.5-0.6 m³/min, spray liquid feed rate 5-7 g/min and the particles were dried to give particles after drying (608.0 g). The total amount of the particles after drying was sieved to give organic acid-coated particles (355 μm-105 μm) (604.0 g).

[Preparation of Water-Insoluble Polymer Coating Liquid]

In purified water (294.0 g) were suspended triacetin (3.6 g), titanium oxide (1.2 g) and talc (18.0 g), further, aminoalkylmethacrylate copolymer RS (Eudragit RS30D, manufactured by Evonik) (120.0 g) was suspended to give a water-insoluble polymer coating liquid.

[Preparation of Coagulation Inhibiting Substance-Coated Particles]

The organic acid-coated particles (355 μm-105 μm) (300.6 g) were placed and fluidized in a fine particle coater granulator/Wurster, the water-insoluble polymer coating liquid (116.5 g) was sprayed at spray air pressure 0.3 MPa, spray air flow rate 50 NL/min, inlet air temperature 39° C., inlet air flow rate 0.5 m³/min, spray liquid feed rate 2 g/min to give water-insoluble polymer-coated particles (299.2 g). To the total amount of the particles were added light anhydrous silicic acid (Sylysia 320, manufactured by FUJI SILYSIA CHEMICAL LTD.) (0.89 g), mixed in a 10 L plastic bag by hand mixing and cured by shelf drying at 60° C. for 13 hr. The total amount of the particles were sieved to give coagulation inhibiting substance-coated particles (355 μm-105 μm) (298.9 g).

[Preparation of Outer Layer Granules]

In purified water (800.0 g) were dissolved D-mannitol (PEARLITOL 50C, manufactured by ROQUETTE Japan) (80.0 g) and citric anhydride (48.0 g) to give a spray liquid. D-mannitol (PEARLITOL 50C, manufactured by ROQUETTE Japan) (357.2 g), crystalline cellulose (CEOLUS KG-802, manufactured by Asahi Kasei Corporation) (50.0 g), low-substituted hydroxypropylcellulose (50.0 g) and crospovidone (Polyplasdone XL-10, manufactured by ISP) (25.0 g) were placed and fluidized in a fluid bed dryer granulator (LAB-1, manufactured by POWREX), the spray liquid (232.0 g) was sprayed at spray air pressure 0.13 MPa, spray air flow rate 60 NL/min, inlet air temperature 85° C., inlet air flow rate 0.2-0.3 m³/min, spray liquid feed rate 6 g/min and the granules were dried to give outer layer granules (472.2 g).

[Preparation of Orally Disintegrating Tablet Containing Coagulation Inhibiting Substance-Coated Particles]

The coagulation inhibiting substance-coated particles (138.8 g), the outer layer granules (180.0 g), crystalline cellulose (CEOLUS KG-802, manufactured by Asahi Kasei Corporation) (37.1 g), acesulfame potassium (3.5 g), aspartame (3.5 g), peppermint cortone (0.7 g) and sodium stearyl fumarate (3.5 g) were mixed 200 times in a 10 L plastic bag by hand mixing to give a blended product. The blended product was tableted using a rotary type tableting machine at average 7 kN to give an orally disintegrating tablet (weight 524.4 mg and diameter 10.5 mm) containing 20 mg of a free form of compound A.

Example 19

[Preparation of Outer Layer Granules]

In purified water (600.0 g) were dissolved and suspended D-mannitol (PEARLITOL 50C, manufactured by ROQUETTE Japan) (30.0 g), citric anhydride (30.0 g) and crospovidone (Kollidon CL-SF, manufactured by BASF) (30.0 g) to give a spray liquid. D-mannitol (PEARLITOL 50C, manufactured by ROQUETTE Japan) (66.24 g), D-mannitol (PEARLITOL 100SD, manufactured by ROQUETTE Japan) (264.0 g), crystalline cellulose (CEOLUS KG-802, manufactured by Asahi Kasei Corporation) (48.0 g), low-substituted hydroxypropylcellulose (48.0 g) and crospovidone (Kollidon CL-F, manufactured by BASF) (24.0 g) were placed and fluidized in a fluid bed dryer granulator (LAB-1, manufactured by POWREX), the spray liquid (276.0 g) was sprayed at spray air pressure 0.14 MPa, spray air flow rate 60 NL/min, inlet air temperature 83-85° C., inlet air flow rate 0.2 m³/min, spray liquid feed rate 6 g/min and the granules were dried to give an outer layer granules (444.7 g).

[Preparation of Orally Disintegrating Tablet Containing coagulation Inhibiting Substance-Coated Particles]

The coagulation inhibiting substance-coated particles (107.4 g) obtained in Example 15, the outer layer granules (121.6 g), crystalline cellulose (CEOLUS KG-802, manufactured by Asahi Kasei Corporation) (13.2 g), crospovidone (Polyplasdone XL-10, manufactured by ISP) (13.2 g), magnesium alumino metasilicate (Neusilin FL2, manufactured by Fuji Chemical Industries Co., Ltd.) (0.72 g), acesulfame potassium (2.4 g), aspartame (2.4 g), peppermint cortone (0.48 g) and sodium stearyl fumarate (2.64 g) were mixed in a 10 L plastic bag by hand mixing to give a blended product. The blended product was tableted using a rotary type tableting machine at average 6.7 kN to give an orally disintegrating tablet (weight 440 mg and diameter 10.0 mm) containing 20 mg of a free form of compound A.

Example 20

[Preparation of Orally Disintegrating Tablet Containing Coagulation Inhibiting Substance-Coated Particles]

The blended product obtained in Example 19 was tableted using a rotary type tableting machine at average 4.0 kN to give an orally disintegrating tablet (weight 220 mg and diameter 8.0 mm) containing 10 mg of a free form of compound A.

The formulation (Calculated) of Examples 15-20 are shown in Table 1-5.

Eudragit RS30D (trade name) is sold in the form of a 30% water dispersion. In the Table, Eudragit RS30D shows a solid content.

TABLE 1-5

| | | Example 15 | Example 16 | Example 17 | Example 18 | Example 19 | Example 20 |
|---|---|---|---|---|---|---|---|
| compound A-containing particles | NONPAREIL 105T | 77 | 77 | 77 | 77 | 77 | 38.5 |
| | compound A | 26.72 | 26.72 | 26.72 | 26.72 | 26.72 | 13.36 |
| | HPMC TC-5E | 3.28 | 3.28 | 3.28 | 2.98 | 3.28 | 1.64 |
| organic acid coating layer | monosodium fumarate | 40 | 40 | 20 | 60 | 40 | 20 |
| | succinic acid | 20 | 20 | 20 | 20 | 20 | 10 |
| | Eudragit RLPO | 1.2 | 1.2 | 1.2 | 1.2 | 1.2 | 0.6 |
| water-insoluble polymer coating layer | Eudragit RS30D | — | — | — | 6 | — | — |
| | Eudragit RSPO | 4.8 | 3.78 | 2.88 | — | 4.8 | 2.4 |
| | Eudragit RLPO | 1.2 | 1.62 | 1.92 | — | 1.2 | 0.6 |
| | triacetin | 0.6 | 0.54 | 0.48 | 0.6 | 0.6 | 0.3 |
| | talc | 3 | 2.7 | 2.4 | 3 | 3 | 1.5 |
| | titanium oxide | 0.6 | 0.56 | 0.56 | 0.2 | 0.6 | 0.3 |
| | yellow ferric oxide | — | — | 0.06 | — | — | — |
| coagulation inhibiting substance coating layer | Sylysia 320 | 0.6 | 0.6 | 0.6 | 0.6 | 0.6 | 0.3 |
| outer layer granule component | D-mannitol | 167 | 143.6 | 143.6 | 188.6 | 142.6 | 71.3 |
| | citric anhydride | 5 | 5 | 5 | 6 | 5 | 2.5 |
| | crystalline cellulose KG-802 | 24 | 20 | 20 | 25 | 20 | 10 |
| | crospovidone | 17 | 15 | 15 | 12.5 | 20 | 10 |
| | L-HPC LH-33 | 24 | 10 | 10 | 25 | 15 | 7.5 |
| blended product component | crystalline cellulose KG-802 | 24 | 22 | 19 | 53 | 22 | 11 |
| | crospovidone | 24 | 22 | 11.4 | — | 22 | 11 |
| | Neusilin FL2 | 1.3 | 1.2 | 1.9 | — | 1.2 | 0.6 |
| | acesulfame potassium | 4 | 4 | 4 | 5 | 4 | 2 |
| | aspartame | 4 | 4 | 4 | 5 | 4 | 2 |
| | peppermint cortone | 0.8 | 0.8 | 0.8 | 1 | 0.8 | 0.4 |
| | sodium stearyl fumarate | 4.4 | 4.4 | 3.8 | 5 | 4.4 | 2.2 |
| total (mg/tablet) | | 478.9 | 440 | 380 | 524.4 | 440 | 220 |

Example 21

[Preparation of Compound a Coating Liquid]

In purified water (27.056 kg) was dissolved hydroxypropylmethylcellulose 2910 (1.153 kg) to give a hydroxypropylmethylcellulose 2910 solution. Successively, compound A (9.639 kg) was uniformly dispersed in the hydroxypropylmethylcellulose 2910 solution to give a compound A coating liquid.

[Preparation of Compound A-Coated Particles]

Lactose/crystalline cellulose spherical granules (25.025 kg) were placed and fluidized in a fine particle coater granulator/Wurster (FD-GPCG-120SPC, manufactured by POWREX, hereinafter the same), the compound A coating liquid was sprayed at spray air flow rate 400-500 NL/min, inlet air temperature 71° C., inlet air flow rate 13-14 m$^3$/min, spray liquid feed rate 100-135 g/min and the particles were dried to give particles after drying. The total amount of the particles after drying was sieved to give compound A-coated particles (300 μm-132 μm).

[Preparation of Organic Acid Coating Liquid]

In purified water (84.630 kg) and anhydrous ethanol (46.270 kg) were dissolved ammonioalkylmethacrylate copolymer (Eudragit RLPO, manufactured by Evonik) (0.484 kg) and succinic acid (8.060 kg). Successively, monosodium fumarate (MONOFUMAR, manufactured by NIPPON SHOKUBAI CO., LTD.) (16.120 kg) jet milled in advance was uniformly dispersed to give an organic acid coating liquid.

[Preparation of Organic Acid-Coated Particles]

The compound A-coated particles (300 μm-132 μm) (33.170 kg) were placed and fluidized in a fine particle coater granulator/Wurster, the organic acid coating liquid was sprayed at spray air flow rate 550-700 NL/min, inlet air temperature 71-73° C., inlet air flow rate 14-17 m$^3$/min, spray liquid feed rate 160-240 g/min and the particles were dried to give particles after drying. The total amount of the particles after drying was sieved to give organic acid-coated particles (355 μm-132 μm).

[Preparation of Water-Insoluble Polymer Coating Liquid]

In purified water (3.329 kg) and anhydrous ethanol (29.962 kg) were suspended triacetin (0.222 kg), titanium oxide (0.230 kg) and talc (1.110 kg), further, ammonioalkylmethacrylate copolymer (Eudragit RSPO, manufactured by Evonik) (1.776 kg) and ammonioalkylmethacrylate copolymer (Eudragit RLPO, manufactured by Evonik) (0.444 kg) were dissolved to give a water-insoluble polymer coating liquid.

[Preparation of Coagulation Inhibiting Substance Coating Liquid]

In purified water (3.124 kg) was dispersed light anhydrous silicic acid (0.164 kg) to give a coagulation inhibiting substance coating liquid.

[Preparation of Coagulation Inhibiting Substance-Coated Particles]

The organic acid-coated particles (355 μm-132 μm) (46.087 kg) were placed and fluidized in a fine particle coater granulator/Wurster, the water-insoluble polymer coating liquid was sprayed at spray air flow rate 400-500 NL/min, inlet air temperature 31-32° C., inlet air flow rate 17 m$^3$/min, spray liquid feed rate 80-100 g/min to give water-insoluble polymer-coated particles. Successively, the coagulation inhibiting substance coating liquid was sprayed at spray air flow rate 500 NL/min, inlet air temperature 32-68° C., inlet air flow rate 17 m$^3$/min, spray liquid feed rate 112 g/min and the particles were dried to give particles after drying. The total amount of the particles after drying was sieved to give coagulation inhibiting substance-coated particles (355 μm-132 μm).

[Preparation of Outer Layer Granules]

In purified water (27.000 kg) were dissolved and suspended D-mannitol (PEARLITOL 50C, manufactured by ROQUETTE Japan) (2.160 kg), citric anhydride (0.810 kg) and crospovidone (Kollidon CL-SF, manufactured by BASF) (1.350 kg) to give a spray liquid. D-mannitol (PEARLITOL 100SD, manufactured by ROQUETTE Japan) (37.395 kg), crystalline cellulose (CEOLUS KG-802, manufactured by Asahi Kasei Corporation) (5.400 kg), low-substituted hydroxypropylcellulose (L-HPC LH-33, manufactured by Shin-Etsu Chemical Co., Ltd.) (5.400 kg) and crospovidone (Kollidon CL-F, manufactured by BASF) (2.700 kg) were placed and fluidized in a fluid bed dryer granulator (FD-WSG-60TW, manufactured by POWREX), the spray liquid was sprayed at spray air flow rate 750-850 NL/min, inlet air temperature 73-77° C., inlet air flow rate 17-19 m$^3$/min, spray liquid feed rate 350-400 g/min and the granules were dried to give outer layer granules.

[Preparation of Orally Disintegrating Tablet Containing Coagulation Inhibiting Substance-Coated Particles]

The coagulation inhibiting substance-coated particles (146.1 g), outer layer granules (163.6 g), crystalline cellulose (CEOLUS KG-802, manufactured by Asahi Kasei Corporation) (17.60 g), crospovidone (Kollidon CL-F, manufactured by BASF) (14.08 g), magnesium alumino metasilicate (Neusilin FL2, manufactured by Fuji Chemical Industries Co., Ltd.) (1.760 g), acesulfame potassium (2.4 g), aspartame (2.4 g), strawberry flavor (0.56 g) and sodium stearyl fumarate (3.52 g) were placed in a 10 L plastic bag and mixed 200 times by hand mixing to give a blended product. The blended product was tableted using a rotary type tableting machine at average 10 kN to give an orally disintegrating tablet (weight 440 mg and diameter 10.0 mm) containing 20 mg of a free form of compound A.

Example 22

[Preparation of Orally Disintegrating Tablet Containing Coagulation Inhibiting Substance-Coated Particles]

The coagulation inhibiting substance-coated particles (146.1 g) obtained in Example 21, the outer layer granules (163.6 g) obtained in Example 21, crystalline cellulose (CEOLUS KG-802, manufactured by Asahi Kasei Corporation) (17.60 g), crospovidone (Kollidon CL-F, manufactured by BASF) (14.08 g), magnesium alumino metasilicate (Neusilin UFL2, manufactured by Fuji Chemical Industries Co., Ltd.) (1.760 g), acesulfame potassium (2.4 g), aspartame (2.4 g), strawberry flavor (0.56 g) and sodium stearyl fumarate (3.52 g) were placed in a 10 L plastic bag and mixed 200 times by hand mixing to give a blended product. The blended product was tableted using a rotary type tableting machine at average 10 kN to give an orally disintegrating tablet (weight 440 mg and diameter 10.0 mm) containing 20 mg of a free form of compound A.

Example 23

[Preparation of Compound a Coating Liquid]

In purified water (25.840 kg) was dissolved hydroxypropylmethylcellulose 2910 (1.130 kg) to give a hydroxypropylmethylcellulose 2910 solution. Successively, compound A (9.639 kg) was uniformly dispersed in the hydroxypropylmethylcellulose 2910 solution to give a compound A coating liquid.

[Preparation of Compound A-Coated Particles]

Lactose/crystalline cellulose spherical granules (25.025 kg) were placed and fluidized in a fine particle coater granulator/Wurster (FD-GPCG-120SPC, manufactured by POWREX, hereinafter the same), the compound A coating liquid was sprayed at spray air flow rate 400-500 NL/min, inlet air temperature 71° C., inlet air flow rate 13-14 m$^3$/min, spray liquid feed rate 100-135 g/min and the particles were dried to give particles after drying. The total amount of the particles after drying was sieved to give compound A-coated particles (300 μm-132 μm).

[Preparation of Organic Acid Coating Liquid]

In purified water (84.630 kg) and anhydrous ethanol (46.270 kg) were dissolved ammonioalkylmethacrylate copolymer (Eudragit RLPO, manufactured by Evonik) (0.484 kg) and succinic acid (8.060 kg). Successively, monosodium fumarate (MONOFUMAR, manufactured by NIPPON SHOKUBAI CO., LTD.) (16.120 kg) jet milled in advance was uniformly dispersed to give an organic acid coating liquid.

[Preparation of Organic Acid-Coated Particles]

The compound A-coated particles (300 μm-132 μm) (33.170 kg) were placed and fluidized in a fine particle coater granulator/Wurster, the organic acid coating liquid was sprayed at spray air flow rate 550-700 NL/min, inlet air temperature 71-73° C., inlet air flow rate 14-17 m$^3$/min, spray liquid feed rate 160-240 g/min and the particles were dried to give particles after drying. The total amount of the particles after drying was sieved to give organic acid-coated particles (355 μm-132 μm).

[Preparation of Water-Insoluble Polymer Coating Liquid]

In purified water (2.312 kg) and anhydrous ethanol (20.806 kg) were suspended triacetin (0.154 kg), titanium oxide (0.160 kg) and talc (0.771 kg), further, ammonioalkylmethacrylate copolymer (Eudragit RSPO, manufactured by Evonik) (1.541 kg) was dissolved to give a water-insoluble polymer coating liquid.

[Preparation of Coagulation Inhibiting Substance Coating Liquid]

In purified water (1.627 kg) was dispersed light anhydrous silicic acid (0.086 kg) to give a coagulation inhibiting substance coating liquid.

[Preparation of Coagulation Inhibiting Substance-Coated Particles]

The organic acid-coated particles (355 μm-132 μm) (24.002 kg) were placed and fluidized in a fine particle coater granulator/Wurster, the water-insoluble polymer coating liquid was sprayed at spray air flow rate 300 NL/min, inlet air temperature 32° C., inlet air flow rate 14 m$^3$/min, spray liquid feed rate 75 g/min to give water-insoluble polymer-coated particles. Successively, the coagulation inhibiting substance coating liquid was sprayed at spray air flow rate 400 NL/min, inlet air temperature 32-71° C., inlet air flow rate 14 m$^3$/min, spray liquid feed rate 85 g/min and the particles were dried to give particles after drying. The total amount of the particles after drying was sieved to give coagulation inhibiting substance-coated particles (355 μm-132 μm).

[Preparation of Outer Layer Granules]

In purified water (27.500 kg) were dissolved and suspended D-mannitol (PEARLITOL 50C, manufactured by ROQUETTE Japan) (1.375 kg), citric anhydride (1.375 kg) and crospovidone (Kollidon CL-SF, manufactured by BASF) (1.375 kg) to give a spray liquid. D-mannitol (PEARLITOL 50C, manufactured by ROQUETTE Japan) (7.865 kg), D-mannitol (PEARLITOL 100SD, manufactured by ROQUETTE Japan) (30.250 kg), crystalline cellulose (CEOLUS KG-802, manufactured by Asahi Kasei Corporation) (5.500 kg), low-substituted hydroxypropylcellulose (L-HPC LH-33, manufactured by Shin-Etsu Chemical Co., Ltd.) (5.500 kg) and crospovidone (Kollidon CL-F, manufactured by BASF) (2.750 kg) were placed and fluidized in a fluid bed dryer granulator (FD-WSG-60TW, manufactured by POWREX), the spray liquid was sprayed at spray air flow rate 750-850 NL/min, inlet air temperature 70° C., inlet air flow rate 18-20 m$^3$/min, spray liquid feed rate 350-400 g/min and the granules were dried to give outer layer granules.

[Preparation of Orally Disintegrating Tablet Containing Coagulation Inhibiting Substance-Coated Particles]

The coagulation inhibiting substance-coated particles (28.50 g), the outer layer granules (28.50 g), crystalline cellulose (CEOLUS KG-802, manufactured by Asahi Kasei Corporation) (3.08 g), crospovidone CL-F (Kollidon CL-F, manufactured by BASF) (3.08 g), magnesium alumino metasilicate (Neusilin FL2, manufactured by Fuji Chemical Industries Co., Ltd.) (0.308 g), acesulfame potassium (0.56 g), aspartame (0.56 g), peppermint flavor (0.112 g) and sodium stearyl fumarate (0.616 g) were placed in a glass bottle and mixed 100 times by hand mixing to give a blended product. The blended product was tableted using a single punch tableting machine to give an orally disintegrating tablet (weight 450 mg and diameter 10.0 mm) containing 20 mg of a free form of compound A.

Example 24

[Preparation of Water-Insoluble Polymer Coating Liquid]

In purified water (2.312 kg) and anhydrous ethanol (20.806 kg) were suspended triacetin (0.154 kg), titanium oxide (0.160 kg) and talc (0.771 kg), further, ammonioalkylmethacrylate copolymer (Eudragit RSPO, manufactured by Evonik) (1.233 kg) and ammonioalkylmethacrylate copolymer (Eudragit RLPO, manufactured by Evonik) (0.308 kg) were dissolved to give a water-insoluble polymer coating liquid.

[Preparation of Coagulation Inhibiting Substance Coating liquid]

In purified water (1.627 kg) was dispersed light anhydrous silicic acid (0.086 kg) to give a coagulation inhibiting substance coating liquid.

[Preparation of Coagulation Inhibiting Substance-Coated Particles]

The organic acid-coated particles (355 μm-132 μm) (24.002 kg) obtained in Example 23 were placed and fluidized in a fine particle coater granulator/Wurster, the water-insoluble polymer coating liquid was sprayed at spray air flow rate 400 NL/min, inlet air temperature 30° C., inlet air flow rate 14 m$^3$/min, spray liquid feed rate 75 g/min to give water-insoluble polymer-coated particles. Successively, the coagulation inhibiting substance coating liquid was sprayed at spray air flow rate 500 NL/min, inlet air temperature 30-71° C., inlet air flow rate 14 m$^3$/min, spray liquid feed rate 85 g/min and the particles were dried to give particles after drying. The total amount of the particles after drying was sieved to give coagulation inhibiting substance-coated particles (355 μm-132 μm).

[Preparation of Orally Disintegrating Tablet Containing Coagulation Inhibiting Substance-Coated Particles]

The coagulation inhibiting substance-coated particles (28.50 g), the outer layer granules (28.50 g) obtained in Example 23, crystalline cellulose (CEOLUS KG-802, manufactured by Asahi Kasei Corporation) (3.08 g), crospovidone (Kollidon CL-F, manufactured by BASF) (3.08 g), magnesium alumino metasilicate (Neusilin FL2, manufactured by Fuji Chemical Industries Co., Ltd.) (0.308 g), acesulfame potassium (0.56 g), aspartame (0.56 g), peppermint flavor (0.112 g) and sodium stearyl fumarate (0.616 g) were placed in a glass bottle and mixed 100 times by hand mixing to give a blended product. The blended product was tableted using a single punch tableting machine to give an orally disintegrating tablet (weight 450 mg and diameter 10.0 mm) containing 20 mg of a free form of compound A.

Example 25

[Preparation of Compound a Coating Liquid]

In purified water (25.840 kg) was dissolved hydroxypropylmethylcellulose 2910 (1.100 kg) to give a hydroxypropylmethylcellulose 2910 solution. Successively, compound A (9.205 kg) was uniformly dispersed in the hydroxypropylmethylcellulose 2910 solution to give a compound A coating liquid.

[Preparation of Compound A-Coated Particles]

Lactose/crystalline cellulose spherical granules (25.025 kg) were placed and fluidized in a fine particle coater granulator/Wurster (FD-GPCG-120SPC, manufactured by POWREX, hereinafter the same), the compound A coating liquid was sprayed at spray air flow rate 400-500 NL/min, inlet air temperature 71° C., inlet air flow rate 13-14 m$^3$/min, spray liquid feed rate 100-135 g/min and the particles were dried to give particles after drying. The total amount of the particles after drying was sieved to give compound A-coated particles (300 μm-132 μm).

[Preparation of Organic Acid Coating Liquid]

In purified water (84.630 kg) and anhydrous ethanol (46.270 kg) were dissolved ammonioalkylmethacrylate copolymer (Eudragit RLPO, manufactured by Evonik) (0.484 kg) and succinic acid (8.060 kg). Successively, monosodium fumarate (MONOFUMAR, manufactured by NIPPON SHOKUBAI CO., LTD.) (16.120 kg) jet milled in advance was uniformly dispersed to give an organic acid coating liquid.

[Preparation of Organic Acid-Coated Particles]

The compound A-coated particles (300 μm-132 μm) (33.170 kg) were placed and fluidized in a fine particle coater granulator/Wurster, the organic acid coating liquid was sprayed at spray air flow rate 550-700 NL/min, inlet air temperature 71-73° C., inlet air flow rate 14-17 m$^3$/min, spray liquid feed rate 160-240 g/min and the particles were dried to give particles after drying. The total amount of the particles after drying was sieved to give organic acid-coated particles (355 μm-132 μm).

[Preparation of Water-Insoluble Polymer Coating Liquid]

In purified water (3.884 kg) and anhydrous ethanol (34.956 kg) were suspended triacetin (0.259 kg), titanium oxide (0.269 kg) and talc (1.295 kg), further, ammonioalkylmethacrylate copolymer (Eudragit RSPO, manufactured by Evonik) (2.071 kg) and ammonioalkylmethacrylate copolymer (Eudragit RLPO, manufactured by Evonik) (0.518 kg) were dissolved to give a water-insoluble polymer coating liquid.

[Preparation of Coagulation Inhibiting Substance Coating Liquid]

In purified water (3.124 kg) was dispersed light anhydrous silicic acid (0.164 kg) to give a coagulation inhibiting substance coating liquid.

[Preparation of Coagulation Inhibiting Substance-Coated Particles]

The organic acid-coated particles (355 μm-132 μm) (46.087 kg) were placed and fluidized in a fine particle coater granulator/Wurster, the water-insoluble polymer coating liquid was sprayed at spray air flow rate 400-500 NL/min, inlet air temperature 31° C., inlet air flow rate 17 m$^3$/min, spray liquid feed rate 80-100 g/min to give water-insoluble polymer-coated particles. Successively, the coagulation inhibiting substance coating liquid was sprayed at spray air flow rate 500 NL/min, inlet air temperature 31-68° C., inlet air flow rate 17 m$^3$/min, spray liquid feed rate 130 g/min and the particles were dried to give particles after drying. The total amount of the particles after drying was sieved to give coagulation inhibiting substance-coated particles (355 μm-132 μm).

[Preparation of Outer Layer Granules]

In purified water (27.000 kg) were dissolved and suspended D-mannitol (PEARLITOL 50C, manufactured by ROQUETTE Japan) (1.350 kg), citric anhydride (1.350 kg) and crospovidone CL-SF (Kollidon CL-SF, manufactured by BASF) (1.350 kg) to give a spray liquid. D-mannitol (PEARLITOL 100SD, manufactured by ROQUETTE Japan) (35.910 kg), crystalline cellulose (CEOLUS KG-802, manufactured by Asahi Kasei Corporation) (5.400 kg), low-substituted hydroxypropylcellulose (L-HPC LH-33, manufactured by Shin-Etsu Chemical Co., Ltd.) (5.400 kg) and crospovidone (Kollidon CL-F, manufactured by BASF) (2.700 kg) were placed and fluidized in a fluid bed dryer granulator (FD-WSG-60TW, manufactured by POWREX), the spray liquid was sprayed at spray air flow rate 750-850 NL/min, inlet air temperature 73-78° C., inlet air flow rate 17-19 m$^3$/min, spray liquid feed rate 350-400 g/min and the granules were dried to give outer layer granules.

[Preparation of Orally Disintegrating Tablet Containing Coagulation Inhibiting Substance-Coated Particles]

The coagulation inhibiting substance-coated particles (13.70 g), the outer layer granules (14.85 g), crystalline cellulose (CEOLUS KG-802, manufactured by Asahi Kasei Corporation) (1.65 g), crospovidone (Kollidon CL-F, manufactured by BASF) (1.65 g), magnesium alumino metasilicate (Neusilin FL2, manufactured by Fuji Chemical Industries Co., Ltd.) (0.165 g), acesulfame potassium (0.3 g), aspartame (0.3 g), strawberry flavor (0.06 g) and sodium stearyl fumarate (0.33 g) were placed in a glass bottle and mixed 100 times by hand mixing to give a blended product. The blended product was tableted using a single punch tableting machine to give an orally disintegrating tablet (weight 440 mg and diameter 10.0 mm) containing 20 mg of a free form of compound A.

Example 26

The blended product obtained in Example 25 was tableted using a single punch tableting machine to give an orally disintegrating tablet (weight 220 mg and diameter 8.0 mm) containing 10 mg of a free form of compound A.

The formulation (Calculated) of Examples 21-26 are shown in Table 1-6.

TABLE 1-6

| | | Example 21 | Example 22 | Example 23 | Example 24 | Example 25 | Example 26 |
|---|---|---|---|---|---|---|---|
| compound A-containing particles | NONPAREIL 105T | 77 | 77 | 77 | 77 | 77 | 38.5 |
| | compound A | 26.72 | 26.72 | 26.72 | 26.72 | 26.72 | 13.36 |
| | HPMC TC-5E | 3.28 | 3.28 | 3.28 | 3.28 | 3.28 | 1.64 |

TABLE 1-6-continued

|  |  | Example 21 | Example 22 | Example 23 | Example 24 | Example 25 | Example 26 |
|---|---|---|---|---|---|---|---|
| organic acid coating layer (intermediate layer) | monosodium fumarate | 40 | 40 | 40 | 40 | 40 | 20 |
|  | succinic acid | 20 | 20 | 20 | 20 | 20 | 10 |
|  | Eudragit RLPO | 1.2 | 1.2 | 1.2 | 1.2 | 1.2 | 0.6 |
| water-insoluble polymer coating layer | Eudragit RSPO | 6.48 | 6.48 | 10.8 | 8.64 | 6.48 | 3.24 |
|  | Eudragit RLPO | 1.62 | 1.62 | — | 2.16 | 1.62 | 0.81 |
|  | triacetin | 0.81 | 0.81 | 1.08 | 1.08 | 0.81 | 0.405 |
|  | talc | 4.05 | 4.05 | 5.4 | 5.4 | 4.05 | 2.025 |
|  | titanium oxide | 0.84 | 0.84 | 1.12 | 1.12 | 0.84 | 0.42 |
| coagulation inhibiting substance coating layer | light anhydrous silicic acid | 0.6 | 0.6 | 0.6 | 0.6 | 0.6 | 0.3 |
| outer layer granule component | D-mannitol | 146.5 | 146.5 | 143.6 | 143.6 | 138 | 69 |
|  | citric anhydride | 3 | 3 | 5 | 5 | 5 | 2.5 |
|  | crystalline cellulose KG-802 | 20 | 20 | 20 | 20 | 20 | 10 |
|  | crospovidone | 15 | 15 | 15 | 15 | 15 | 7.5 |
|  | L-HPC LH-33 | 20 | 20 | 20 | 20 | 20 | 10 |
| blended product component | crystalline cellulose KG-802 | 22 | 22 | 22 | 22 | 22 | 11 |
|  | crospovidone | 17.6 | 17.6 | 22 | 22 | 22 | 11 |
|  | Neusilin | 2.2 | 2.2 | 2.2 | 2.2 | 2.2 | 1.1 |
|  | acesulfame potassium | 3 | 3 | 4 | 4 | 4 | 2 |
|  | aspartame | 3 | 3 | 4 | 4 | 4 | 2 |
|  | flavor | 0.7 | 0.7 | 0.8 | 0.8 | 0.8 | 0.4 |
|  | sodium stearyl fumarate | 4.4 | 4.4 | 4.4 | 4.4 | 4.4 | 2.2 |
| total (mg/tablet) |  | 440 | 440 | 450.2 | 450.2 | 440 | 220 |

Experimental Example 1 (Dissolution Test of Preparation)

A dissolution test was performed according to the Paddle Method (50 rpm) of the Japanese Pharmacopoeia General Test Method 6.10 Dissolution Test Method or Rotating Basket Method (100 rpm) of the Japanese Pharmacopoeia General Test Method 6.10 Dissolution Test Method. That is, a dissolution test solution (900 mL) heated to 37° C. was added to disperse the preparation. Sampling was performed at each predetermined time while rotating the paddle or basket at the predetermined rotating speed, and the dissolution amount of the object compound in the filtrate obtained using a membrane filter was quantified by HPLC.

The results are shown in FIG. 1-FIG. 10.

All preparations showed a lag time of not less than 2 min and showed that they can significantly reduce the bitter taste derived from compound A.

Experimental Example 2 (Dissolution Amount of Compound a in Saturated Organic Acid)

Citric acid, succinic acid, fumaric acid or malic acid was dissolved and saturated in the Japanese Pharmacopoeia dissolution test 2nd fluid (JP2), and filtered. Successively, compound A (0.4 g) was added to a filtrate (10 mL) saturated with an organic acid and the mixture was shaken at room temperature for 1 hr. The solution after shaking was filtered, diluted 50-fold with the Japanese Pharmacopoeia dissolution test 2nd fluid, and the diluted solution was diluted 20-fold with the Japanese Pharmacopoeia dissolution test 2nd fluid. The solution obtained by diluting twice was subjected to HPLC measurement and the dissolution amount of compound A was measured.

The results are shown in Table 2. Compound A in the form of fumarate showed a low concentration only when a high concentration of fumaric acid was present. It was also shown that succinic acid hardly influence the dissolution amount of compound A.

TABLE 2

|  | saturated organic acid | | | | |
|---|---|---|---|---|---|
|  | none | succinic acid | fumaric acid | citric acid | malic acid |
| concentration ($\mu g \cdot mL$) | 5.22 | 5.76 | 0.67 | 26.30 | 26.64 |

Experimental Example 3 (Influence of Concentration of Organic Acid Same as Organic Acid Forming a Salt with a Pharmaceutically Active Ingredient, or a Salt Thereof, on Dissolution Amount of the Pharmaceutically Active Ingredient Forming Salt with Organic Acid (Confirmation of Common Ion Effect))

Figure 11:
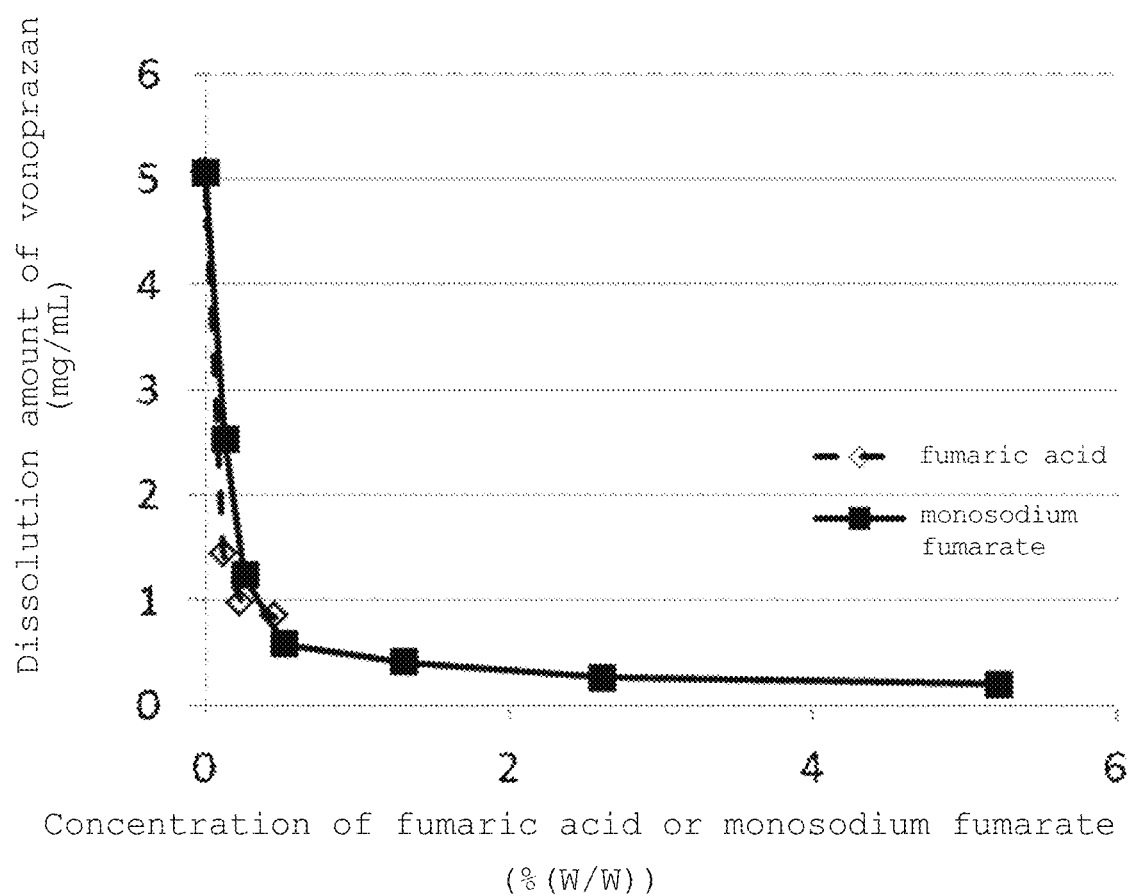
FIG. 11 is a graph showing the results of Experimental Example 3.

Solutions containing various concentrations of fumaric acid or monosodium fumarate dissolved in the Japanese Pharmacopoeia dissolution test 2nd fluid were prepared. Then, 50 mg of compound A was measured and charged in a 10 mL plastic tube and each of the above-mentioned solution (5 mL) was added and the mixture was vigorously shaken at room temperature for 1 hr. The suspension after shaking was filtered, diluted 100-fold and subjected to HPLC measurement. The dissolution amount of compound A was measured. The results are shown in FIG. 11. The dissolution amount of compound A in the form of fumarate was shown to be influenced by the concentration of fumaric acid or monosodium fumarate in the solvent.

Experimental Example 4 (Measurement of Dissolution Profile of Compound a, Fumaric Acid, Succinic Acid)

The water-insoluble polymer coated particle of Example 1 or the coagulation inhibiting substance coated particle of Reference Example 3, each of which contained 60 mg of compound A, was subjected to a dissolution test using Rotating Basket at 100 rpm and in the same manner as in Experimental Example 1. The dissolution amounts of fumaric acid or succinic acid as well as compound A were also measured. As for fumaric acid and succinic acid, the residual rate of each organic acid in the particles were inversely calculated from the dissolution rate, and the value of the maximum dissolution amount was normalized assuming 0% of the residual rate.

Figure 12:
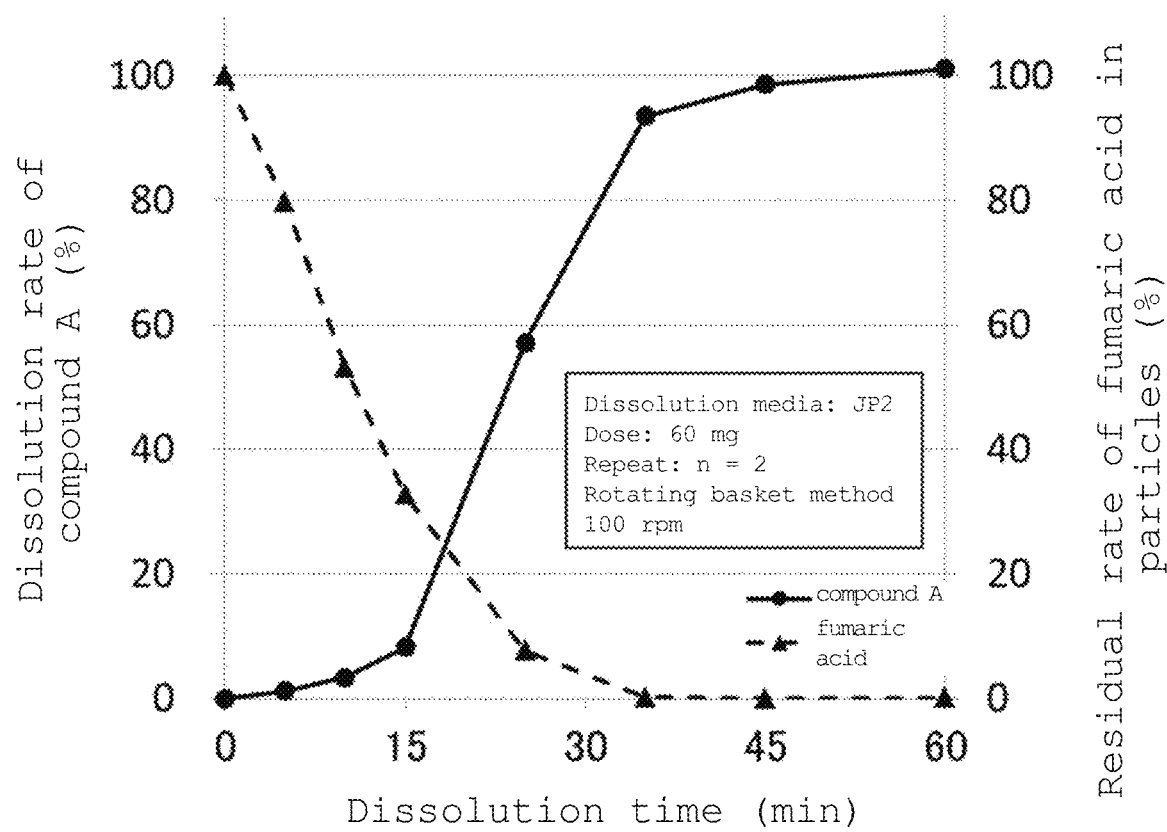
FIG. 12 is a graph showing the results of the dissolution test of Experimental Example 4 performed using the water-insoluble polymer-coated particles obtained in Example 1.
Figure 13:
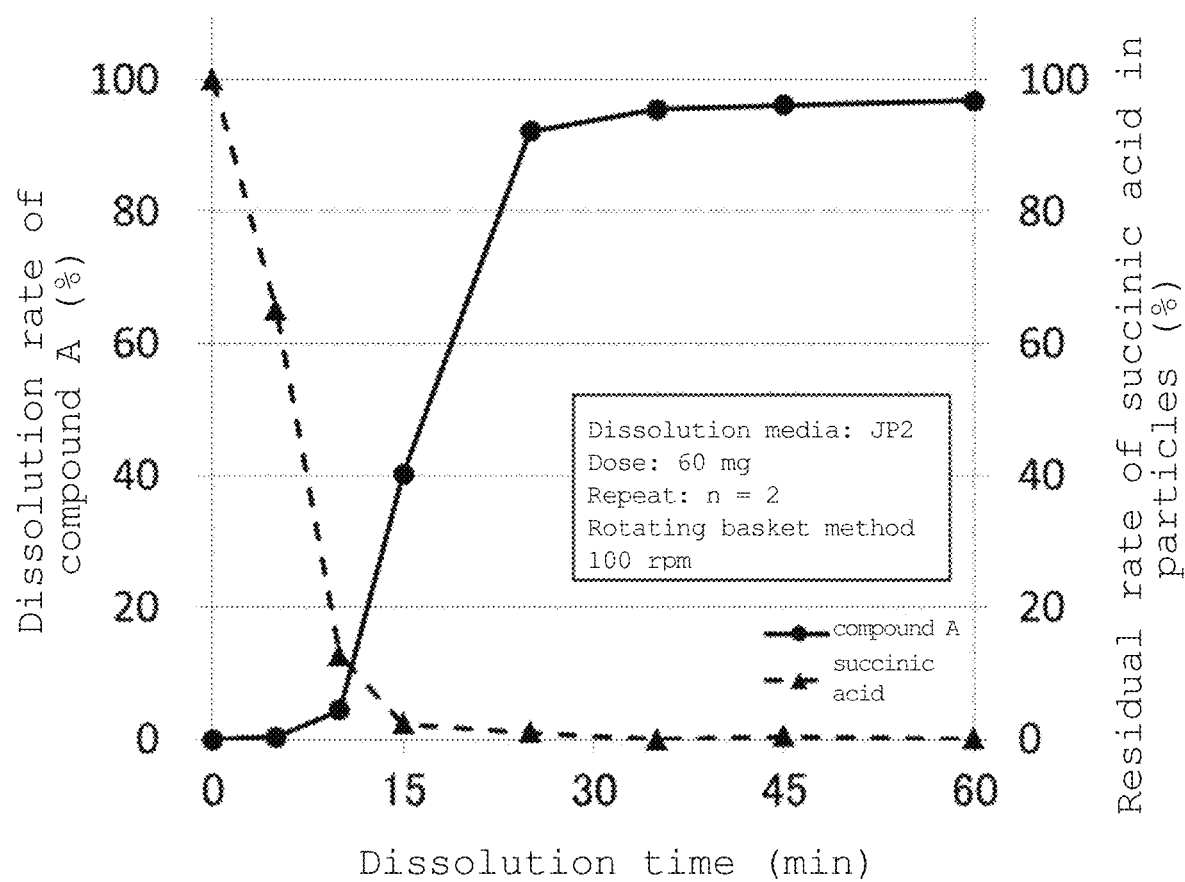
FIG. 13 is a graph showing the results of the dissolution test of Experimental Example 4 performed using the coagulation inhibiting substance-coated particles obtained in Reference Example 3.

The results are shown in FIG. 12-FIG. 13. It was observed that dissolution of compound A started after dissolution of fumaric acid or succinic acid from the granules.

Experimental Example 5 (Confirmation of Dissolution Control Mechanism-1)

The water-soluble polymer coated particle 3 obtained in Reference Example 2 and containing 60 mg of compound A was subjected to a dissolution test using paddle at 100 rpm and in the same manner as in Experimental Example 1. The dissolution media was the Japanese Pharmacopoeia dissolution test 2nd fluid, the Japanese Pharmacopoeia dissolution test 2nd fluid added with 10% (W/W) sodium carbonate, the Japanese Pharmacopoeia dissolution test 2nd fluid added with 13% (W/W) succinic acid, or the Japanese Pharmacopoeia dissolution test 2nd fluid added with 0.6% (W/W) fumaric acid.

Figure 14:
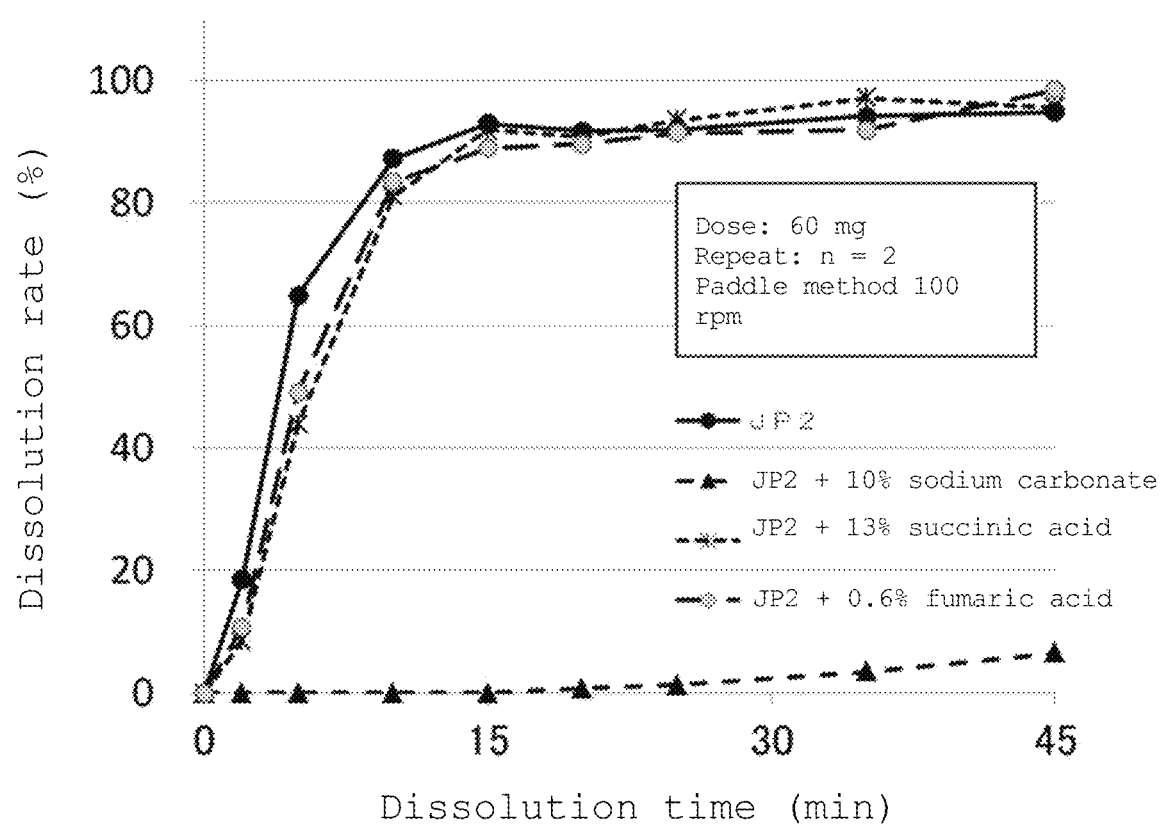
FIG. 14 is a graph showing the results of the dissolution test of Experimental Example 5 performed using the water-insoluble polymer-coated particles 3 obtained in Reference Example 2.

The results are shown in FIG. 14. Sodium carbonate having a salting out action on water-soluble polymers suppressed dissolution of compound A, whereas fumaric acid and succinic acid did not show a dissolution suppressive action. From the results, it was shown that fumaric acid and succinic acid does not show a water-soluble polymer salting out action.

Experimental Example 6 (Confirmation of Dissolution Control Mechanism-2)

The water-insoluble polymer-coated particle obtained in Reference Example 1 and containing 60 mg of compound A was subjected to a dissolution test using paddle at 100 rpm and in the same manner as in Experimental Example 1. The dissolution media was the Japanese Pharmacopoeia dissolution test 2nd fluid, the Japanese Pharmacopoeia dissolution test 2nd fluid added with 13% (W/W) succinic acid, the Japanese Pharmacopoeia dissolution test 2nd fluid added with 0.6% (W/W) monosodium fumarate, or the Japanese Pharmacopoeia dissolution test 2nd fluid added with 0.6% (W/W) fumaric acid.

The compound A-coated particle obtained in Reference Example 1 and containing 60 mg of compound A was subjected to a dissolution test using paddle at 100 rpm and in the same manner as in Experimental Example 1. The dissolution media was the Japanese Pharmacopoeia dissolution test 2nd fluid, the Japanese Pharmacopoeia dissolution test 2nd fluid added with 0.6% (W/W) monosodium fumarate, or the Japanese Pharmacopoeia dissolution test 2nd fluid added with 0.6% (W/W) fumaric acid.

Figure 15:
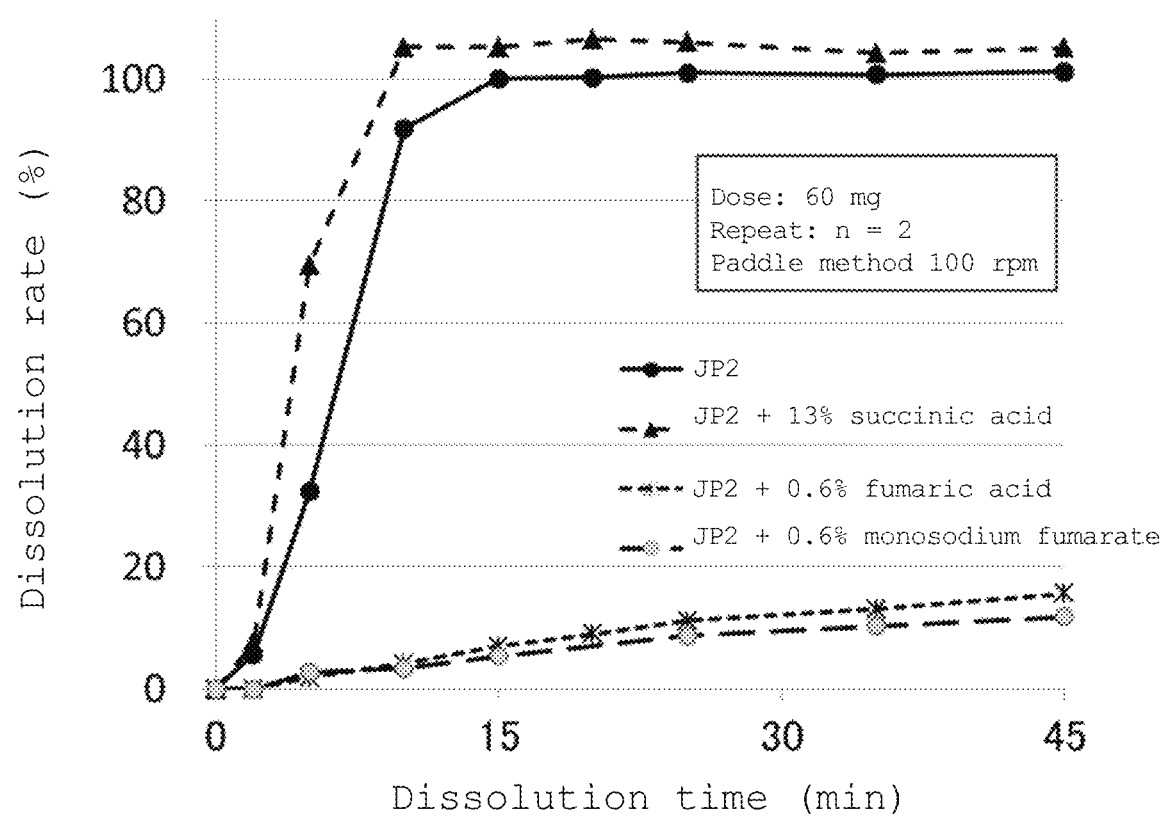
FIG. 15 is a graph showing the results of the dissolution test of Experimental Example 6 performed using the water-insoluble polymer-coated particles obtained in Reference Example 1.
Figure 16:
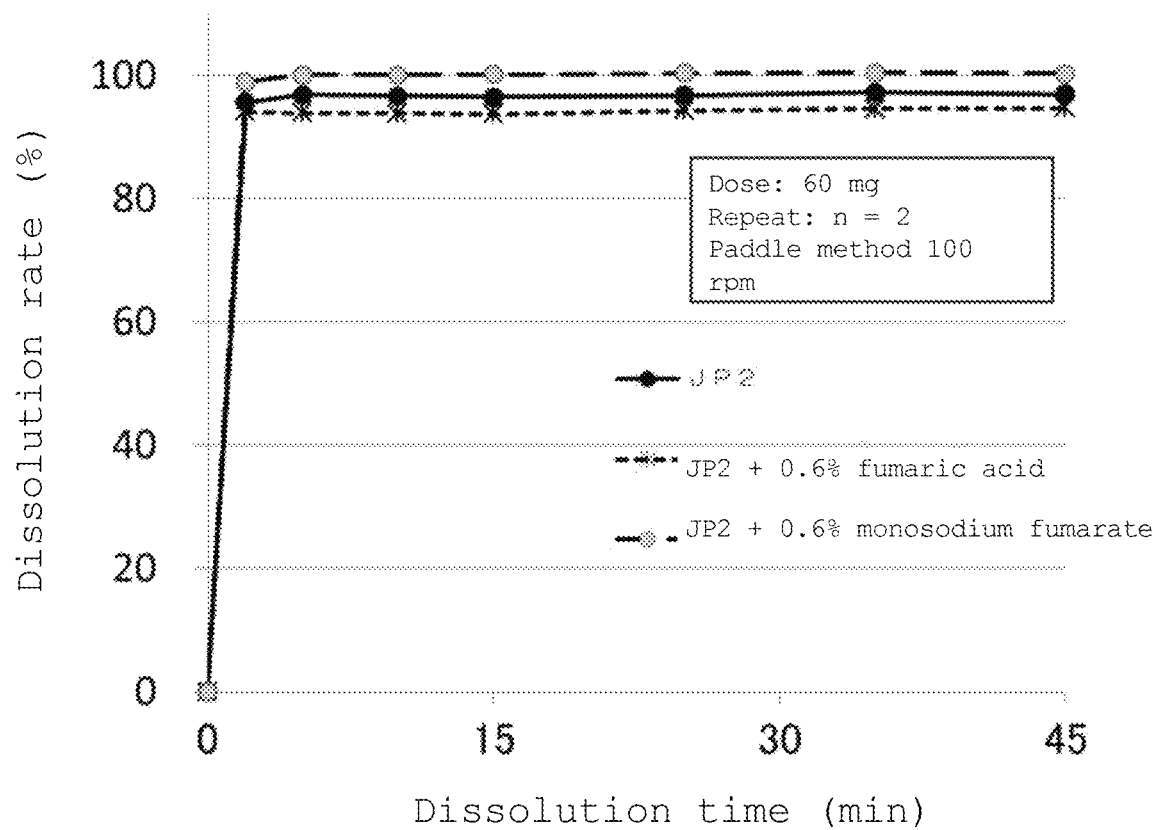
FIG. 16 is a graph showing the results of the dissolution test of Experimental Example 6 performed using the compound A-coated particles obtained in Reference Example 1.

The results are shown in FIG. 15-FIG. 16. Dissolution of the water-insoluble polymer-coated particles was suppressed by fumaric acid or monosodium fumarate present in the dissolution media, whereas dissolution of the compound A-coated particles without coating with a water-insoluble polymer was not suppressed by the two compounds. The results show the dissolution suppressive action on compound A by the common ion effect of fumaric acid or monosodium fumarate requires coating of particles containing compound A with a water-insoluble polymer. It was also shown that fumaric acid or monosodium fumarate needs to be dissolved at a high concentration near the water-insoluble polymer-coated particles containing compound A so that the common ion effect thereof can induce the dissolution suppressive action of compound A. It was further assumed from the results that fumaric acid or monosodium fumarate dissolved from the preparation can be present at a high concentration in the oral cavity having a low water content, and dissolution of compound A is effectively suppressed (bitter taste masking), and that the dissolution suppressive action on compound A by the common ion effect of fumaric acid or monosodium fumarate no longer occurs in the gastrointestinal tract having comparatively high water content, and compound A can be rapidly dissolved.

Experimental Example 7 (Sensory Evaluation-1)

The orally disintegrating tablets obtained in Examples 15-20 were subjected to sensory evaluation. The preparations were put in the mouth, disintegrated and spit out. The bitter taste was evaluated in 5 stages (Table 3). Surprisingly, the bitter taste was remarkably suppressed in all preparations.

The compound A-coated particles, organic acid-coated particles and coagulation inhibiting substance-coated particles obtained in Example 18 were subjected to sensory evaluation. The preparations were put in the mouth and spit out. The bitter taste was evaluated in 5 stages (Table 3). As a result, the bitter taste was remarkably suppressed only in the coagulation inhibiting substance-coated particles.

TABLE 3

| | |
|---|---|
| Example 15 | − |
| Example 16 | − |
| Example 17 | ± |
| Example 18 | − |
| compound A-coated particles of Example 18 | +++ |
| organic acid-coated particles of Example 18 | ++ |
| coagulation inhibiting substance-coated particles of Example 18 | − |
| Example 19 | − |
| Example 20 | − |

+++: very strong bitter taste was felt
++: strong bitter taste was felt
+: rather strong bitter taste was felt
±: slight bitter taste was felt
−: bitter taste was hardly felt Experimental Example 8 (Sensory Evaluation-2)

The orally disintegrating tablets obtained in Examples 21-26 were subjected to sensory evaluation. The preparations were put in the mouth, disintegrated and spit out. The bitter taste was evaluated in 5 stages (Table 4). Surprisingly, the bitter taste was remarkably suppressed in all preparations.

TABLE 4

| | |
|---|---|
| Example 21 | – |
| Example 22 | – |
| Example 23 | – |
| Example 24 | – |
| Example 25 | – |
| Example 26 | – |

+++: very strong bitter taste was felt
++: strong bitter taste was felt
+: rather strong bitter taste was felt
±: slight bitter taste was felt
–: bitter taste was hardly felt This application is based on patent application No. 2017-135046 filed in Japan, the contents of which are incorporated in full herein by this reference.

The invention claimed is:

1. A preparation comprising fine granules or granules comprising
   (1) a core granule containing an organic acid salt of vonoprazan,
   (2) an intermediate layer containing the same organic acid as the organic acid forming the salt of vonoprazan in (1), or a salt thereof, and
   (3) a coating layer containing a water-insoluble polymer, wherein the organic acid salt of vonoprazan is vonoprazan fumarate, the organic acid or a salt thereof in said (2) is fumaric acid or a salt of fumaric acid.

2. The preparation according to claim 1, wherein the water-insoluble polymer is a pH-independent water-insoluble polymer.

3. The preparation according to claim 2, wherein the pH-independent water-insoluble polymer is an ammonioalkylmethacrylate copolymer.

4. The preparation according to claim 1, wherein the organic acid or a salt thereof in said (2) is not less than about 0.5 parts by weight per 100 parts by weight of vonoprazan in said (1).

5. The preparation according to claim 1, wherein the water-insoluble polymer (solid content) in the coating layer in said (3) is about 0.5 parts by weight-about 15 parts by weight per 100 parts by weight of the particles comprising the core granule in said (1) and the intermediate layer in said (2).

6. The preparation according to claim 1, wherein the fine granules or granules have an average particle size of about 75 μm-about 750 μm.

7. The preparation according to claim 1, wherein the intermediate layer of (2) contains the same organic acid as the organic acid forming the salt of vonoprazan in (1), or a salt thereof, and a dissolution controlling substance in a single layer or separate layers.

8. The preparation according to claim 7, wherein the dissolution controlling substance has solubility in water (100 g) at 20° C. of 0.01-500.

9. The preparation according to claim 7, wherein the dissolution controlling substance has pH 2-4 when dissolved in water.

10. The preparation according to claim 7, wherein the dissolution controlling substance is a salt of an organic acid or organic acid.

11. The preparation according to claim 7, wherein the dissolution controlling substance is a divalent carboxylic acid or a salt thereof.

12. The preparation according to claim 7, wherein the dissolution controlling substance is succinic acid or a salt of succinic acid.

13. The preparation according to claim 1, wherein the fine granules or granules are further coated with a coagulation inhibiting substance.

14. The preparation according to claim 13, wherein the coagulation inhibiting substance is an inorganic substance, sugar alcohol or saccharide.

15. The preparation according to claim 1, further comprising a polymer binder.

16. The preparation according to claim 1 as an orally disintegrating tablet.

* * * * *